(12) United States Patent
Tagmose et al.

(10) Patent No.: US 9,242,011 B2
(45) Date of Patent: Jan. 26, 2016

(54) INSULIN ALBUMIN CONJUGATES

(75) Inventors: Tina Møller Tagmose, Ballerup (DK); Peter Madsen, Bagsværd (DK); Thomas Børglum Kjeldsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 705 days.

(21) Appl. No.: 12/935,438

(22) PCT Filed: Mar. 31, 2009

(86) PCT No.: PCT/EP2009/053819
§ 371 (c)(1),
(2), (4) Date: Oct. 8, 2010

(87) PCT Pub. No.: WO2009/121884
PCT Pub. Date: Oct. 8, 2009

(65) Prior Publication Data
US 2011/0039769 A1    Feb. 17, 2011

Related U.S. Application Data

(60) Provisional application No. 61/042,454, filed on Apr. 4, 2008.

(30) Foreign Application Priority Data

Apr. 1, 2008 (EP) .................................. 08103284

(51) Int. Cl.
*C07K 14/62* (2006.01)
*A61K 47/48* (2006.01)

(52) U.S. Cl.
CPC ........... *A61K 47/48284* (2013.01); *C07K 14/62* (2013.01)

(58) Field of Classification Search
None
See application file for complete search history.

(56) References Cited

FOREIGN PATENT DOCUMENTS

| CA | WO 2005/012346 | * | 10/2005 |
|----|----|----|----|
| WO | WO 00/69900 | | 11/2000 |
| WO | WO 01/77137 | | 10/2001 |
| WO | WO 2005/012346 | * | 2/2005 |
| WO | WO 2005/058958 | | 6/2005 |
| WO | WO 2005/103087 | | 11/2005 |
| WO | WO 2007/071068 | | 6/2007 |
| WO | WO 2008/015099 | * | 2/2008 |

OTHER PUBLICATIONS

Thibaudeau et al., Bioconjugate Chemistry, 2005, vol. 16, No. 4, pp. 1000-1008.*
Duttaroy et al., Diabetes, 2005, vol. 54, pp. 251-258.
Shechter Eet Al., Bioconjugate Chemistry, 2005, vol. 16, No. 4, pp. 913-920.
Meloun, B et al. Complete Amino Acid Sequence of Human Serum Albumin. FEBS Letters. 1975. vol. 58(1). pp. 134-137.

* cited by examiner

*Primary Examiner* — Karlheinz R Skowronek
*Assistant Examiner* — Roy Teller
(74) *Attorney, Agent, or Firm* — Rosemarie R. Wilk-Orescan

(57) ABSTRACT

Insulin albumin conjugates consisting of an insulin analogue, a bifunctional linker and albumin can efficiently be used to treat diabetic patients.

12 Claims, 2 Drawing Sheets

INSULIN ALBUMIN CONJUGATES

CROSS-REFERENCE TO RELATED APPLICATIONS

This application is a 35 U.S.C. §371 national stage application of International Patent Application PCT/EP2009/053819 (published as WO 2009/121884 A1), filed Mar. 31, 2009, which claimed priority of European Patent Application 08103284.9, filed Apr. 1, 2008; this application further claims priority under 35 U.S.C. §119 of U.S. Provisional Application 61/042,454, filed Apr. 4, 2008.

FIELD OF THIS INVENTION

The present invention relates to novel insulin albumin conjugates, a method for the preparation of such insulin albumin conjugates, insulin preparations containing the insulin albumin conjugates and a method of treating diabetes mellitus using these insulin albumin conjugates.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 2, 2010. The Sequence Listing is made up of 43 bytes, and the information contained in the attached "SEQUENCE LISTING" is identical to the information in the specification as originally filed. No new matter is added.

BACKGROUND OF THIS INVENTION

Diabetes mellitus (type 1 and type 2 diabetes) is a metabolic disorder in which the ability to utilize glucose is partly or completely lost. About 5% of all people suffer from diabetes and the disorder approaches epidemic proportions. Since the discovery of insulin in the 1920's, continuous efforts have been made to improve the treatment of diabetes mellitus. Since people suffering from diabetes are subject to chronic treatment over several decades, there is a major need for safe, convenient and life quality improving insulin based therapeutics.

Human insulin consists of two polypeptide chains, the so-called A and B chains which contain 21 and 30 amino acid residues. An insulin analogue is human insulin wherein one or more of the amino acids have been exchanged with other amino acids. Some of the commercial available insulin formulations are characterized by a fast onset of action and other formulations have a relatively slow onset but show a more or less prolonged action.

Treatment of type 1 and type 2 diabetes typically includes treatment with a long acting basal insulin for between meal and nocturnal glycemic control together with treatment with a short-acting preprandial bolus insulin for meal stimulated hyperglycemia. The goal for the treatment is maintenance of long-term near normoglycemic control.

Conjugation of a therapeutic peptide or protein such as insulin to human serum albumin or derivatives thereof results in protection of the therapeutic peptide or protein against proteases. The increased size of the therapeutic results in reduced clearance. Conjugation thereby results in a prolonged residence time of the conjugate (see WO 01/77137 and WO 2006/012346). Conjugation of insulin to albumin results in a prolonged action profile and thereby a reduction in injection frequency. The maintenance of near normo-glycemia results in a lower risk of hypo-glycemia (vide Diabetes 2005, vol 54, 251-258, and Bioconjugate Chem. 2005, vol 16, 1000-1008).

Claim 7 in WO 00/69900 relates to a method for protecting a therapeutic peptide from peptidase activity comprising, e.g., forming a peptide-blood component conjugate where the blood component according to claim 14 is albumin. None of the specific examples in WO 00/69900 deals with insulin.

Claim 1 in WO 2005/012346 relates to an insulin derivative comprising an insulin molecule and a reactive group for covalently bonding a blood component. According to claim 2 therein, the reactive group is coupled to an amino acid of the insulin molecule, i.e., human insulin, at a position selected from the positions Gly A1, Phe B1 and Lys B29.

Claim 1 in WO 2005/103087 relates to a method for separating albumin conjugate from unconjugated albumin. The insulins exemplified in WO 2005/103087 are human insulin and insulins having extensions on A1, B1 or B29, all containing A21Asn (A21N).

Claim 1 in WO 2007/071068 relates to a process for preparation of a conjugate comprising albumin covalently linked to a compound. Insulin is mentioned at page 9, line 16, therein. No specific examples are given in WO 2007/071068.

Normally, insulin formulations are administered by subcutaneous injection.

ASPECTS OF THIS INVENTION

An aspect of this invention relates to the furnishing of insulin derivatives which, when administered subcutaneously, provides near normo-glycemia for at least about 6 hours.

An aspect of this invention relates to the furnishing of insulin derivatives which, when administered subcutaneously, provides near normo-glycemia for at least about 12 hours.

An aspect of this invention relates to the furnishing of insulin derivatives which, when administered subcutaneously, provides near normo-glycemia for at least about 18 hours.

An aspect of this invention relates to the furnishing of insulin derivatives which, when administered subcutaneously, provides near normo-glycemia for at least about 24 hours.

An aspect of this invention relates to the furnishing of insulin derivatives which, when administered subcutaneously, provides near normo-glycemia for at least about 36 hours.

An aspect of this invention relates to the furnishing of insulin derivatives which, when administered subcutaneously, provides near normo-glycemia for at least about 48 hours.

An aspect of this invention relates to the furnishing of insulin derivatives which, when administered pulmonary, provides near normo-glycemia for at least about 6 hours.

An aspect of this invention relates to the furnishing of insulin derivatives which, when administered pulmonary, provides near normo-glycemia for at least about 12 hours.

An aspect of this invention relates to the furnishing of insulin derivatives which, when administered pulmonary, provides near normo-glycemia for at least about 18 hours.

An aspect of this invention relates to the furnishing of insulin derivatives which, when administered pulmonary, provides near normo-glycemia for at least about 24 hours.

An aspect of this invention relates to the furnishing of insulin derivatives which, when administered pulmonary, provides near normo-glycemia for at least about 36 hours.

An aspect of this invention relates to the furnishing of insulin derivatives which, when administered pulmonary, provides near normo-glycemia for at least about 48 hours.

An aspect of this invention relates to the furnishing of insulin derivatives which, when administered orally, provides near normo-glycemia for at least about 24 hours.

An aspect of this invention relates to the furnishing of insulin derivatives which, when administered orally, provides near normo-glycemia for at least about 36 hours.

An aspect of this invention relates to the furnishing of insulin derivatives which, when administered orally, provides near normo-glycemia for at least about 48 hours.

Another aspect of this invention relates to the furnishing of insulin derivative which is only to be administered once daily in order to give a satisfactory basal control of the blood glucose level.

Another aspect of this invention relates to the furnishing of insulin derivatives which does not or only to a low degree give rise to weight increase during the treatment.

Another aspect of this invention relates to the furnishing of insulin derivatives which give rise to weight loss during the treatment.

Another aspect of this invention relates to the furnishing of insulin derivatives which do not or only to a low degree give rise to hypo-glycaemic events.

Another aspect of this invention relates to the furnishing of insulin derivatives which are hepato-selective.

The object of this invention is to overcome or ameliorate at least one of the disadvantages of the prior art, or to provide a useful alternative.

DEFINITIONS

Herein, the term insulin covers natural occurring insulins, e.g., human insulin, as well as insulin analogues thereof.

Herein, the term amino acid residue covers an amino acid from which a hydrogen atom has been removed from an amino group and/or a hydroxy group has been removed from a carboxy group and/or a hydrogen atom has been removed from a mercapto group. Imprecise, an amino acid residue may be designated an amino acid.

Herein, the term peptide residue covers a peptide from which a hydrogen atom has been removed from an amino group and/or a hydroxy group has been removed from a carboxy group and/or a hydrogen atom has been removed from a mercapto group. Imprecise, a peptide residue may be designated a peptide.

Herein, the term insulin analogue (or analogue of insulin) covers a polypeptide which has a molecular structure which formally can be derived from the structure of a naturally occurring insulin, e.g., human insulin, by deleting and/or substituting (replacing) one or more amino acid residue occurring in the natural insulin and by, optionally, adding one or more amino acid residues to the A21 amino acid residue. Preferably, the added and/or substituted amino acid residues are codable amino acid residues. For example, the A chain may be extended at its C-terminal end, e.g., by 1, 2, 3 or 4 amino acid residues (compared with human insulin) the positions of which are denoted A22, A23, A24 and A25, respectively. Even though the insulin analogue has an extension at the A21/A22 position, there may be deletions at other positions in said insulin analogue. Similarly as in human insulin, in the insulin analogue present in the compounds of this invention, the A21 amino acid residue is connected N terminally to a Cys residue in the 20 position which Cys residue participates in the forming of an interchain disulphide bridge. Herein, also the term parent insulin or parent insulin analogue is used for the insulin analogue. Mainly, the term parent is used when differentiating from an insulin analogue carrying a side chain which, for example, can be introduced chemically by acylation.

Herein, the term mutation covers any change in amino acid sequence (substitutions and insertions with codable amino acids as well as deletions).

Herein terms like A1, A2, A3 etc. indicate the position 1, 2 and 3, respectively, in the A chain of insulin (counted from the N-terminal end). Similarly, terms like B1, B2, B3 etc. indicates the position 1, 2 and 3, respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are AlaA21, GlyA21 and GlnA21, respectively.

Herein terms like desB29 and desB30 indicate an insulin analogue lacking the B29 or B30 amino acid residue, respectively.

The numbering of the positions in insulin analogues and A and B chains is done so that the parent compound is human insulin with the numbering used for it.

Herein, the expression "codable" in connection with terms like amino acid, amino acid residue, peptide or peptide residue is used to indicate an amino acid, amino acid residue, peptide or peptide residue which can be coded for by a triplet ("codon") of nucleotides, vide genetic engineering.

Herein, the term albumin covers serum albumin from a variety of species e.g. human (HSA, human serum albumin), rat (RSA, rat serum albumin), mouse (MSA, mouse serum albumin), pig (PSA. pig serum albumine), bovine (BSA, bovine serum albumin), dog (CSA, canine seurum albumin) and rabbit (RaSA, rabbit serum albumin), recombinant albumin e.g. Albagen which is recombinant human serum albumin with deletion of the N-terminal residue (Asp) and albumin from a genomic source.

The numbering of the positions in albumin is done so that the parent compound is human serum albumin. The term like Cys34, indicate a Cys in position 34. In Albagen, which is recombinant human serum albumin lacking the first amino acid, the free Cys is referred to as Cys34.

Herein, the term Michael acceptors covers but is not limited to α,β-unsaturated carbonyl moieties, maleimido groups and vinyl sulfone groups.

Herein, the term thiol reactive groups covers but is not limited to iodoacetamide groups, unsymmetric disulfides wherein the bifunctional linker (as defined herein) provides one of the mercapto functions in the unsymmetric disulfide and the other functions as a leaving group. Examples of such unsymmetrical disulfides are pyridyldisulfides, (methoxy- or ethoxycarbonyl)disulfides, and (o-nitro-phenyl)disulfides.

By insulin albumin conjugate having insulin activity is meant an insulin albumin conjugate with either the ability to lower the blood glucose in mammalians as measured in a suitable animal model, which may, e.g., be a rat, rabbit, dog or pig model, after suitable administration, e.g., by intravenous, subcutaneous or pulmonary administration, or an insulin receptor binding affinity.

Herein, the term hepato-selective covers selectivity for insulin action on the liver over insulin action on peripheral tissues such as muscle and/or fat. The action on the liver is preferably more than 5%, 10%, 15%, 20%, 25%, 30%, 35%, 40%, 45%, 50%, 55%, 60%, 65%, 70%, 75%, 80%, 85%, 90%, 95% stronger relative to insulin action on peripheral tissues such as muscle and/or fat. The selectivity of action can eg. be measured by measuring insulin receptor phosphorylation (i.e., activation) time courses in the various tissues after dosing of the insulin albumin conjugate. Alternatively, hepatoselectivity can be measured by clamp techniques by measurement of Ra (rate of glucose appearance, i.e., hepatic glucose production) and Rd(rate of glucose disposal, i.e., glucose uptake in muscle and fat).

A polypeptide with insulin receptor affinity and IGF-1 receptor affinity is a polypeptide which is capable of interacting with an insulin receptor and a human IGF-1 receptor in a suitable binding assay. Such receptor assays are well-know within the field and are further described in the examples. The present insulin albumin conjugate will not bind to the IGF-1 receptor or will have a rather low affinity to said receptor. More precisely, the insulin albumin conjugates of this invention will have an affinity towards the IGF-1 receptor of substantially the same magnitude or less as that of human insulin.

The terms treatment and treating as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The term treatment of a disease as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term prevention of a disease as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term effective amount as used herein means a dosage which is sufficient in order for the treatment of the patient to be effective compared with no treatment.

Unless indicated explicitly, the amino acids mentioned herein are L-amino acids. Further, the left and right ends of an amino acid sequence of a peptide are, respectively, the N- and C-termini, unless otherwise specified.

For the sake of convenience, here follows the names of codable, natural amino acids with the usual three letter codes & one letter codes in parenthesis: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gln & Q), asparagine (Asn & N), glutamic acid (Glu & E), aspartic acid (Asp & D), serine (Ser & S) and threonine (Thr & T). If, due to typing errors, there are deviations from the commonly used codes, the commonly used codes apply. The amino acids present in the insulins of this invention are, preferably, amino acids which can be coded for by a nucleic acid.

The abbreviations used herein are as follows: h is hour, AcCN is acetonitrile, DCM is dichloromethane, DIPEA is diisopropylethylamine, DMF is dimethylformamide, DMSO is dimethylsulfoxide, EtOAc is ethyl acetate, TFA is trifluoroacetic acid, THF is tetrahydrofurane and TSTU is O—(N-succinimidyl)-N,N,N', N'-tetramethyluronium tetrafluoroborate, HOSu is N-hydroxysuccinimide, HOAt is 1-hydroxy-7-aza-benzotriazole, HOBt is 1-hydroxybenzotriazole, MWCO is molecular weight cut of, CV is column volume.

SUMMARY OF THE INVENTION

It has, surprisingly, been found that conjugation of albumin to insulin at a lysine residue at the C-terminal end of the insulin A-chain results in an insulin albumin conjugate with a higher relative affinity for the human insulin receptor than the relative affinity of a similar insulin albumin conjugate conventionally coupled via the B29 lysine. The invention requires synthesis of a bifunctional linker. One function conjugates one end of the linker to the insulin molecule and the other function conjugates the other end of the linker to albumin.

DETAILED DESCRIPTION OF THIS INVENTION

Figure 1:
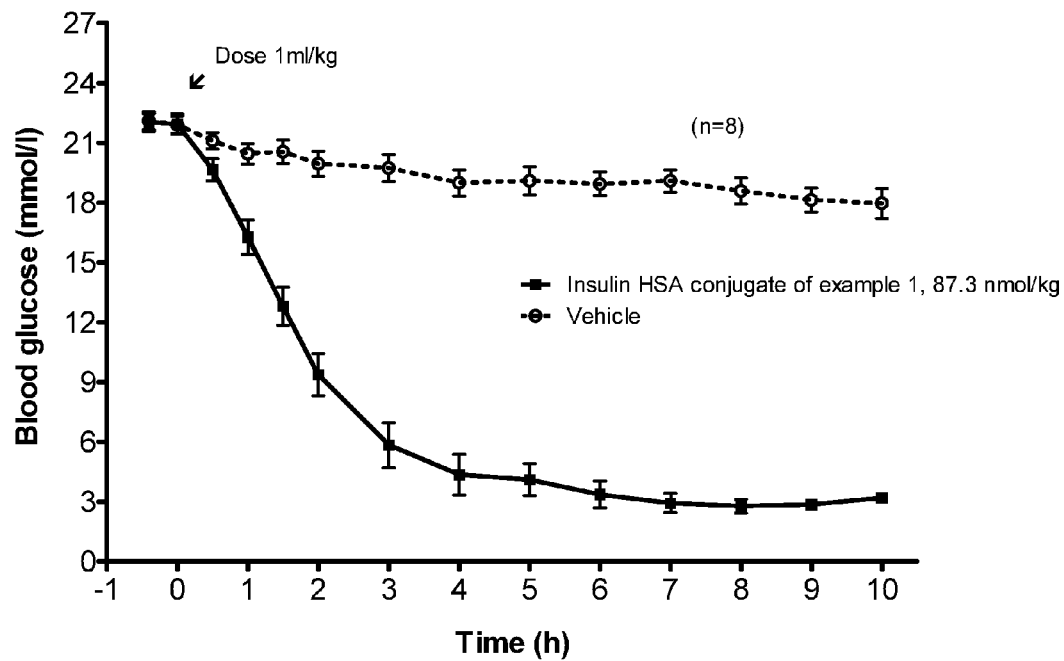
FIG. 1 shows the dependency of blood glucose (mmol/l) on the time (hours) after subcutaneous administration of the insulin albumin conjugate of example 1 (87.3 nmol/kg) as well as of the vehicle to 16 weeks old conscious fed ZDF rats. The result was that the glucose clearance by the insulin albumin conjugate of example 1 is fast, efficient and prolonged.
Figure 2A:
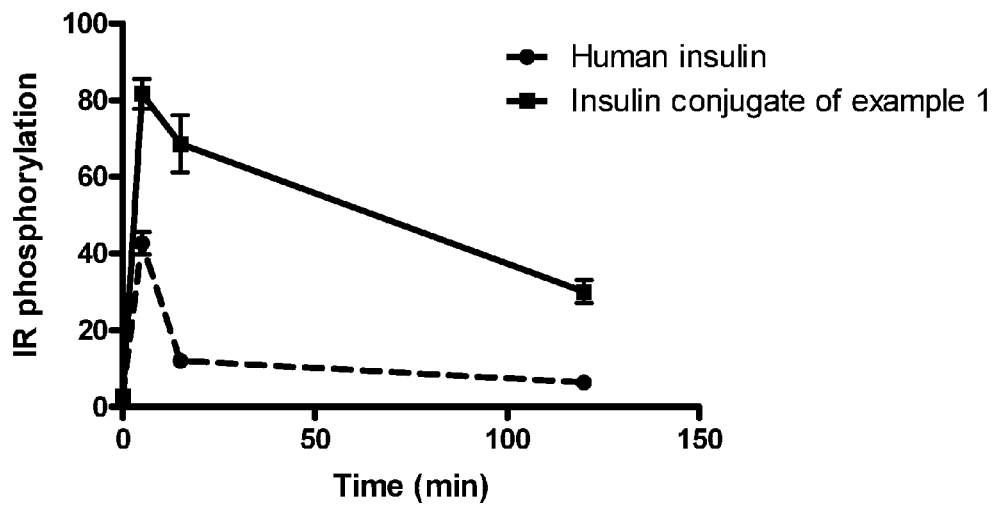
FIGS. 2a, 2b, and 2c shows phosphorylation of insulin receptors of liver (FIG. 2a), and peripheral tissues represented as muscle and fat (FIGS. 2b & 2c, respectively) by the insulin albumin conjugate of example 1. The result of the test was that this conjugate shows hepato-selectivity represented by increased activation of hepatic insulin receptors and decreased activation of insulin receptors in muscle and fat tissue.
Figure 2B:
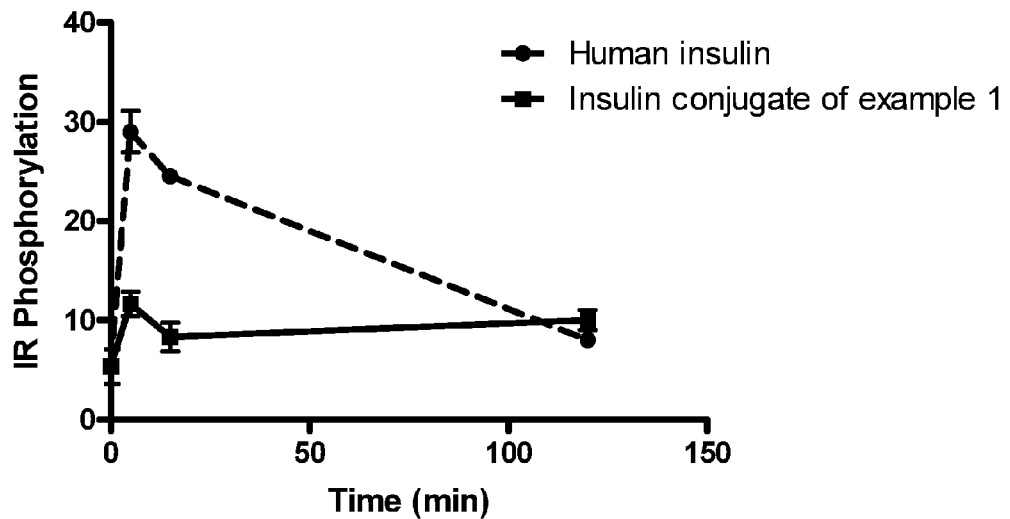
Figure 2C:
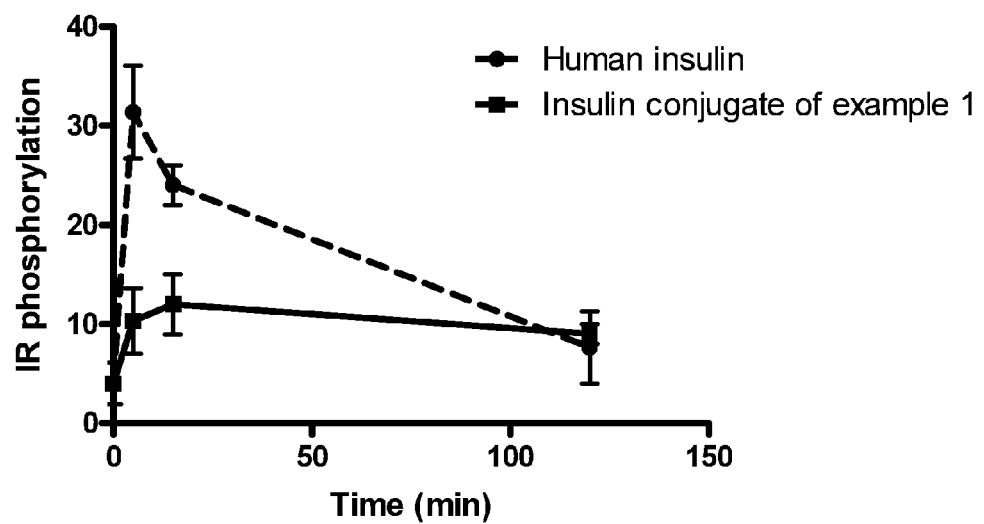

Formally, the insulin albumin conjugates of this invention consist of an insulin analogue, a linker and albumin. In one embodiment, the insulin analogue is A22K, B29R, desB30 human insulin, the linker is 8-[3-(2,5-dioxopyrrolidin-1-yl) propionylamino}octanoyl and the albumin is Albagen, vide example 1 below.

The insulin analogue which is a part of the insulin albumin conjugates of this invention can formally be illustrated as human insulin which has a lysine residue at the C-terminal end of the A-chain, including the C terminal end of an extension of the A-chain which extension, compared with the A21 amino acid residue, consists of a single amino acid residue, i.e., a lysine residue, or a peptide residue, preferably consisting of 2-5 amino acid residues, and, optionally, wherein one or more of the amino acid residues in positions A1-A21 and B1-B30 of insulin has been deleted or substituted by another amino acid residue. As to nomenclature, an amino acid residue connected C terminally to the amino acid residue in position A21 is in the A22 position. Similarly, an amino acid residues present in the peptide residue connected C terminally to the amino acid residue in position A21 is in the positions A22, A23, A24, A25 etc. The insulin analogue has a lysine residue in the C-terminal end of the A-chain (A21K) or the lysine residue is at the C-terminal end of an amino acid extension in the A-chain, compared with the A-chain of human insulin said extension of the A-chain being in the C-terminal end thereof.

One end of the bifunctional linker shall be attached to the C-terminal lysine in the A-chain. The other end of the bifunctional linker shall be attached to albumin.

The attachment from the bifunctional linker to albumin shall preferably be to the free Cys at position 34.

The bifunctional linker can be represented by the general formula (I):

wherein M contains a Michael acceptor represented by a malimido group, a vinylsulfone or the like, a thiol reactive group represented by iodide, pyridyldisulfide, methoxy- or ethoxycarbonyldisulfide and o-nitrophenyldisulphide;

Z is a covalent bond or is chosen from the moieties of the following formulae (wherein the N terminal end thereof is connected to the moiety designated Z (or Y, if present):

$$-NH-(CH_2-CH_2-O)_p-CH_2-CO-;$$

$$-NH-(CH_2)_q-CH_2-CO-;$$

$$-NH-(CH_2-CH_2-O)_r-CH_2-CH_2-CO-;$$

$$-HN-CH_2-CH_2-NH-CO;$$

$$-NH-CH_2-CH_2-O-CH_2-CH_2-NH-CO-CH_2-CH_2-CO-; \text{ or}$$

$$-NH-C_6H_4-CO-;$$

p is 0 or an integer in the range from 1 to 24;
q is 0 or an integer in the range from 1 to 24;
r is 0 or an integer in the range from 1 to 24;
$-C_6H_4-$ is para-phenylene;
n is an integer in the range from 1 to 10 or more preferably 1 or 2;
Y is defined as Z or a covalent bond;
o is 0 or an integer in the range from 1 to 10 or more preferably 0 or 1; and
W is the leaving group of commonly used active esters. Non-limiting examples of such active ester leaving groups are HOSu (N-hydroxysuccimidyl), HOAt, HOBt, benzotriazole and the like.

In one embodiment, the bifunctional linker of formulae I (M-$Z_n$—$Y_o$—W) has one of the following six, general formulae:

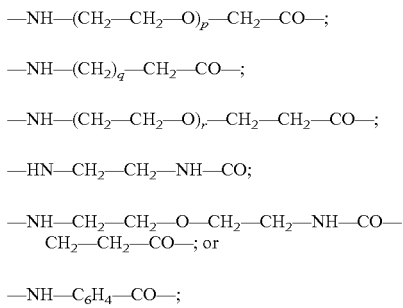

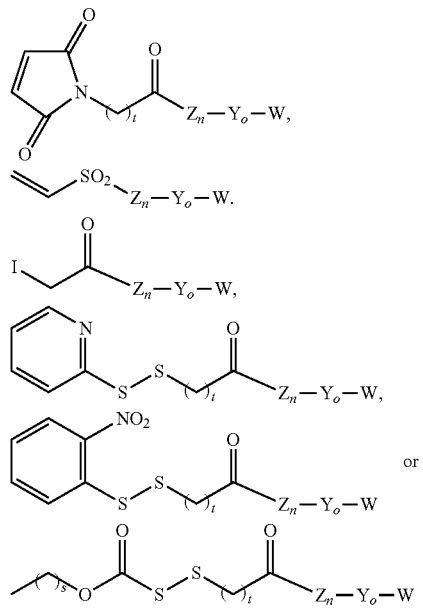

wherein the group $-Z_n-Y_o-W$ is as defined above, and s is an integer in the range from 1 to 5 or zero (0), and t is an integer in the range from 1 to 5.

In another embodiment, the bifunctional linker has the general formula Ia:

wherein M is a Michael acceptor represented by a malimido group, a vinylsulfone or the like, a thiol reactive group represented by iodide, pyridyldisulfide, methoxy- or ethoxycarbonyldisulfide and o-nitro-phenyldisulphide;
m is an integer in the range from 1 to 5,
Z is chosen from the moieties of the following formulae:

$$-NH-(CH_2-CH_2-X)_p-CH_2-CO-;$$

$$-NH-CH_2-CH_2-O-CH_2-CO-;$$

$$-HN-CH_2-CH_2-NH-;$$

$$-NH-CH_2-CH_2-O-CH_2-CH_2-NH-CO-CH_2-CH_2-CO-;$$

$$-NH-CH_2-CH_2-O-CH_2-CH_2-O-CH_2-CO-; \text{ or}$$

$$-NH-C_6H_4-CO-;$$

X is $-O-$ or $-CH_2-$;
p is 0 or an integer in the range from 1 to 24;
$-C_6H_4-$ is para-phenylene;
n is an integer in the range from 1 to 10 or more preferably 1 or 2;
Y is defined as Z or a covalent bond;
o is 0 or an integer in the range from 1 to 10 or more preferably 0 or 1; and
W is the leaving group of commonly used active esters. Non-limiting examples of such active ester leaving groups are HOSu (N-succimidyloxy), HOAt, HOBt, benzotriazole and the like.

One way of preparing the compounds claimed herein is as follows:

An active ester of the bifunctional linker of formula (I) is reacted with the ε amino group [N$^\varepsilon$] of the lysine in the A-chain C-terminal of the insulin to give an insulin derivative of the general formula (II):

wherein Ins represents insulin or an insulin analogue from which, formally, a hydrogen atom has been removed from the amino group present in the C-terminal lysine residue in the A-chain;
and M, m, Z, n, Y and o are as herein defined.

The insulin with the linker attached (insulin of formula II) can then, if desired, be reacted with albumin. This reaction can either be performed ex-vivo (i.e., in vitro) or in vivo. The free thiol of a cysteine residue in albumin reacts with the thiol-reactive functional group M of the linker attached to insulin (e.g. in a Michael reaction or in a substitution reaction) to form the insulin albumin conjugate represented by the general formula (III):

wherein M' is the thiol-reactive group (M) after reaction with a thiol-group of albumin (preferably Cys-34), p, q, r, t, Z, p, $-C_6H_4-$, n, Y and o are as defined herein, and
Alb is albumin as defined herein linked through a free thiol group of a Cys residue, preferably the Cys-34 residue.

In one embodiment, M' is one of the four groups of the following general formulae:

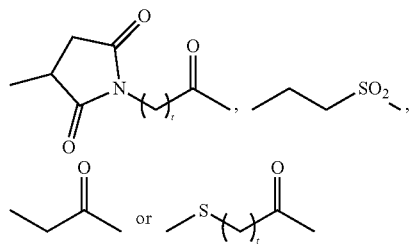

wherein t is as defined above.

The group illustrated by the symbol Ins originates from a compound of the general formula Ins-H wherein Ins is as defined above. Compounds of the general formula Ins-H wherein Ins is as defined above, are either known compounds or compounds which can be prepared analogously with the preparation of known compounds.

Non-limiting, specific examples of the insulin albumin conjugate according to this invention of the general formula III, wherein Alb and Ins each are as defined above, are the following which constitutes one embodiment of this invention:

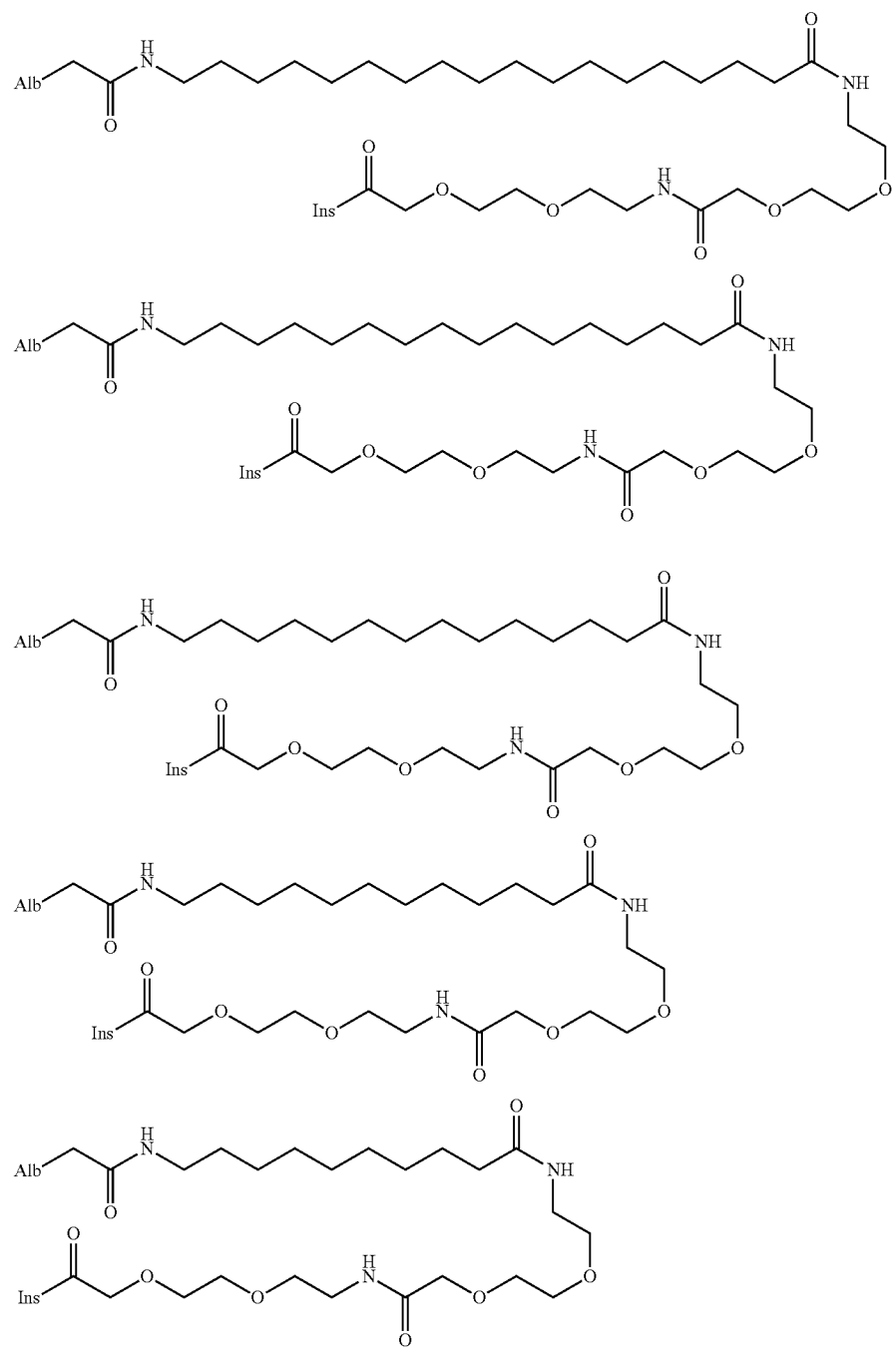

-continued
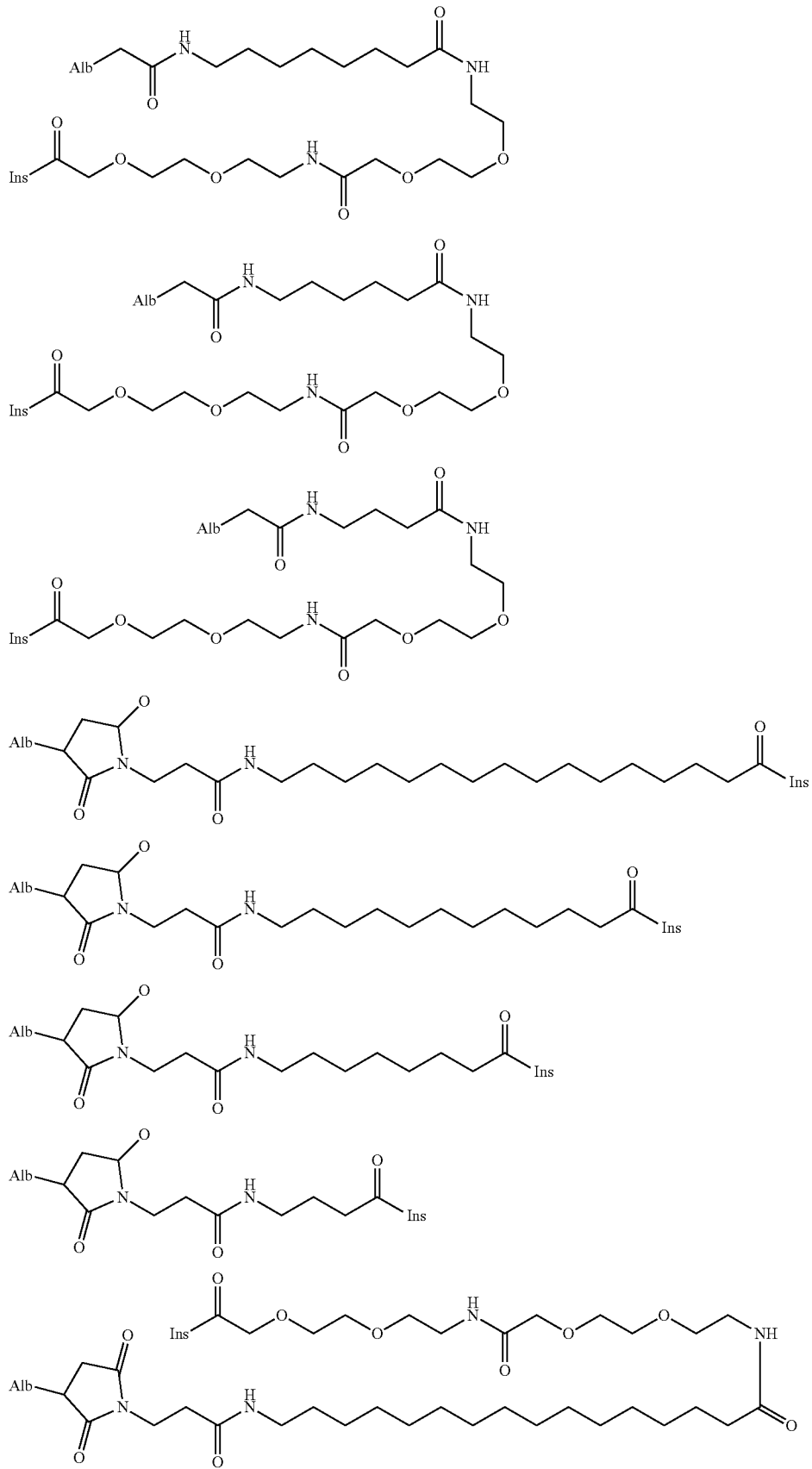

-continued
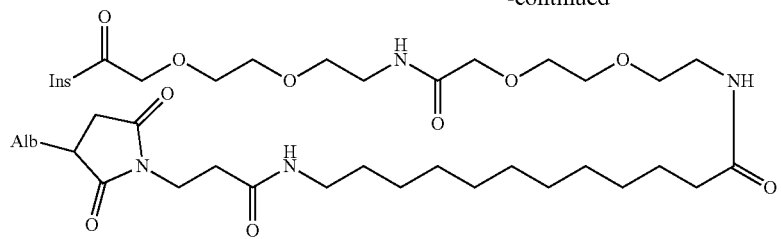
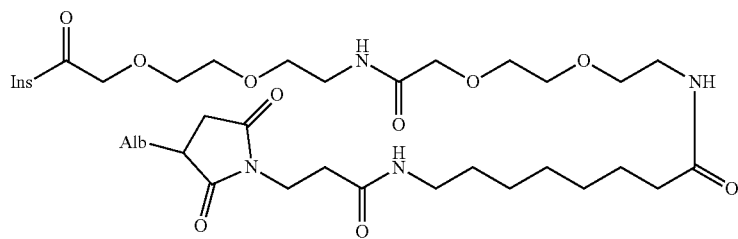
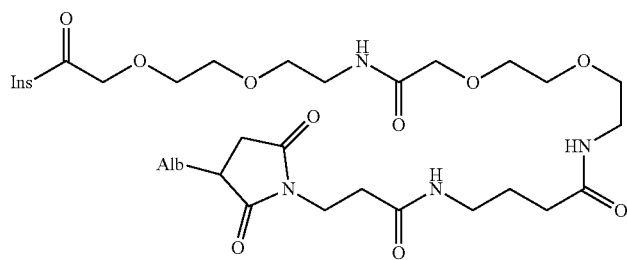
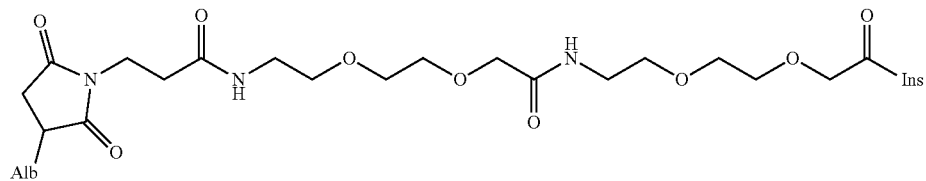
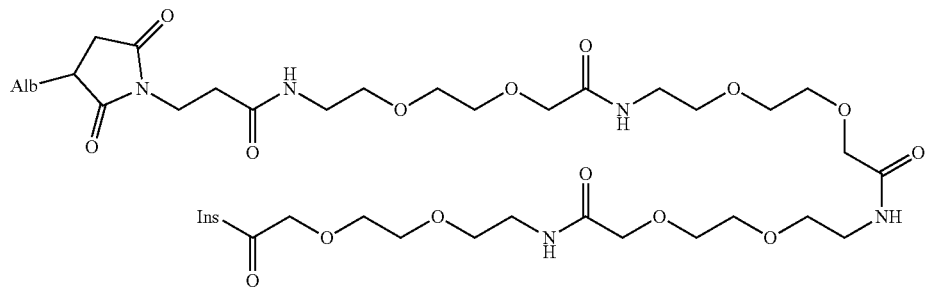
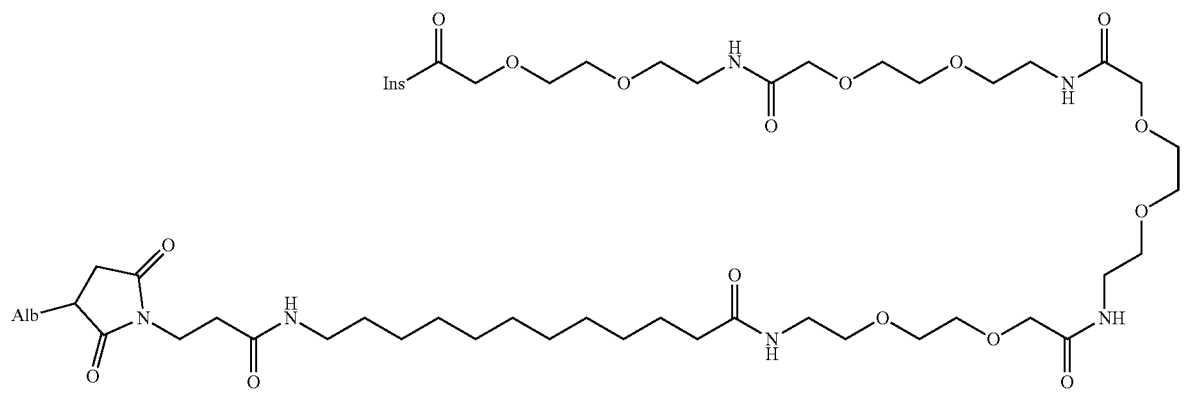

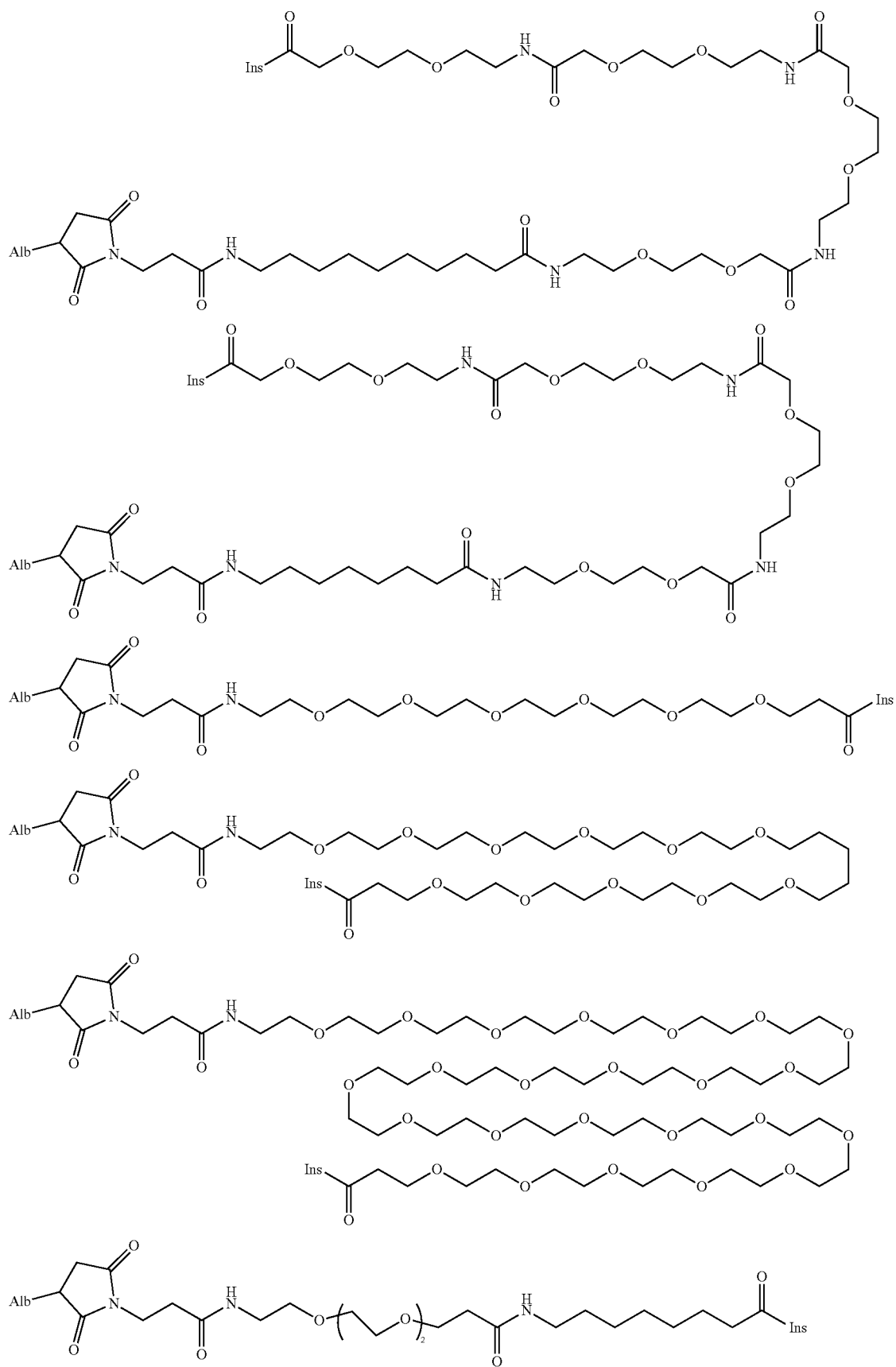

-continued
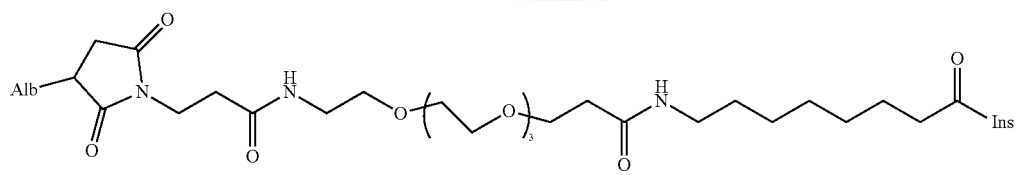
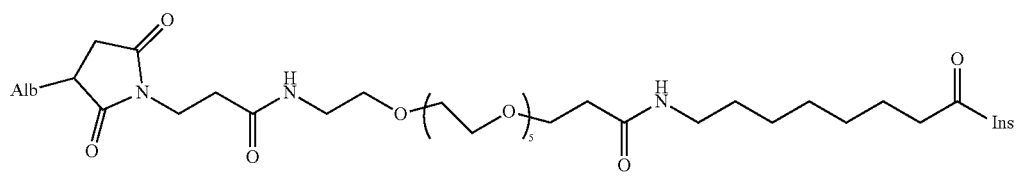
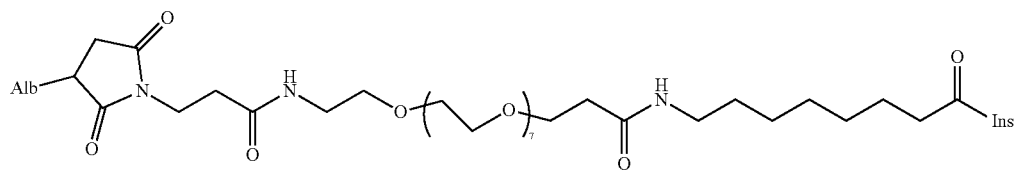
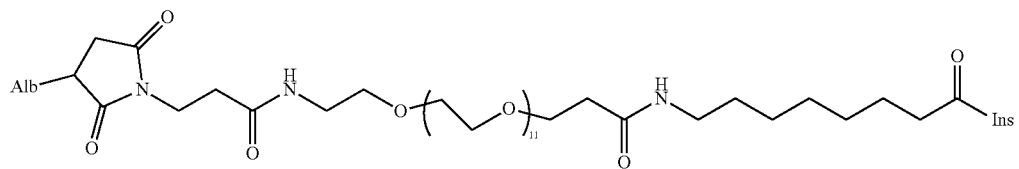
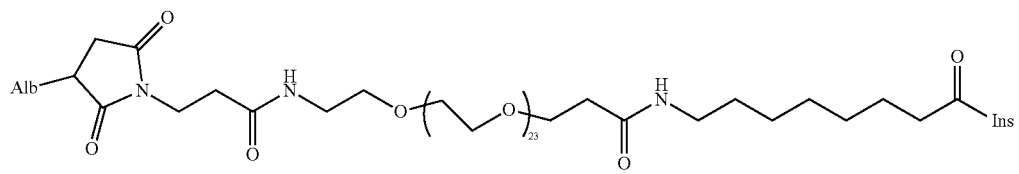
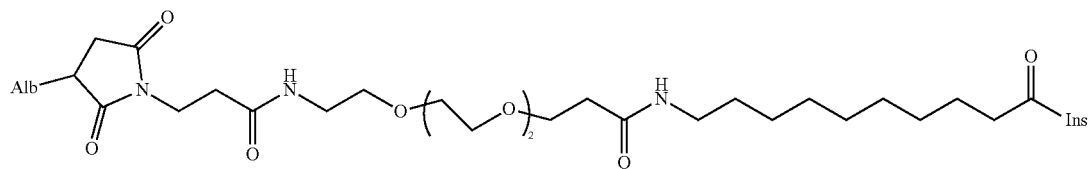
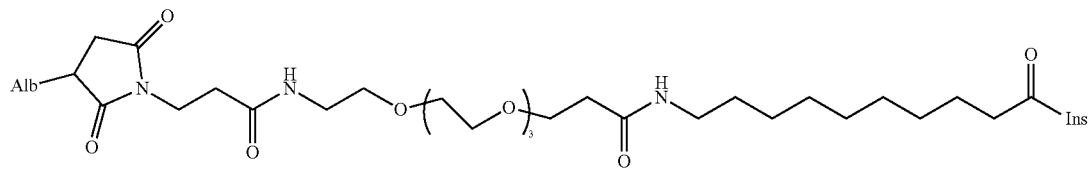
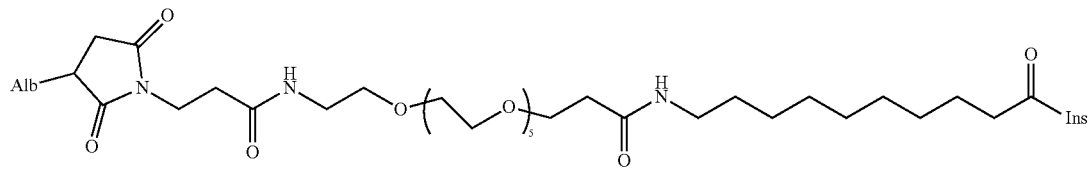
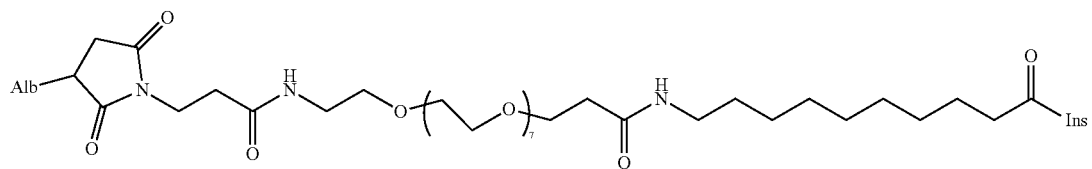
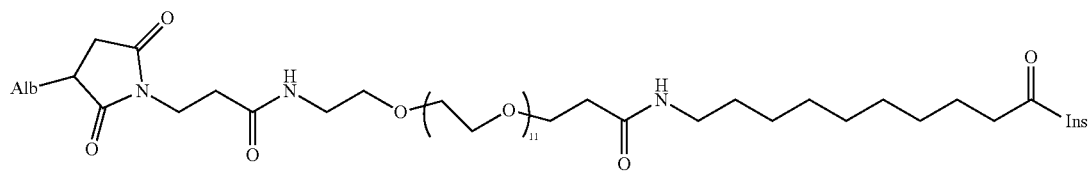

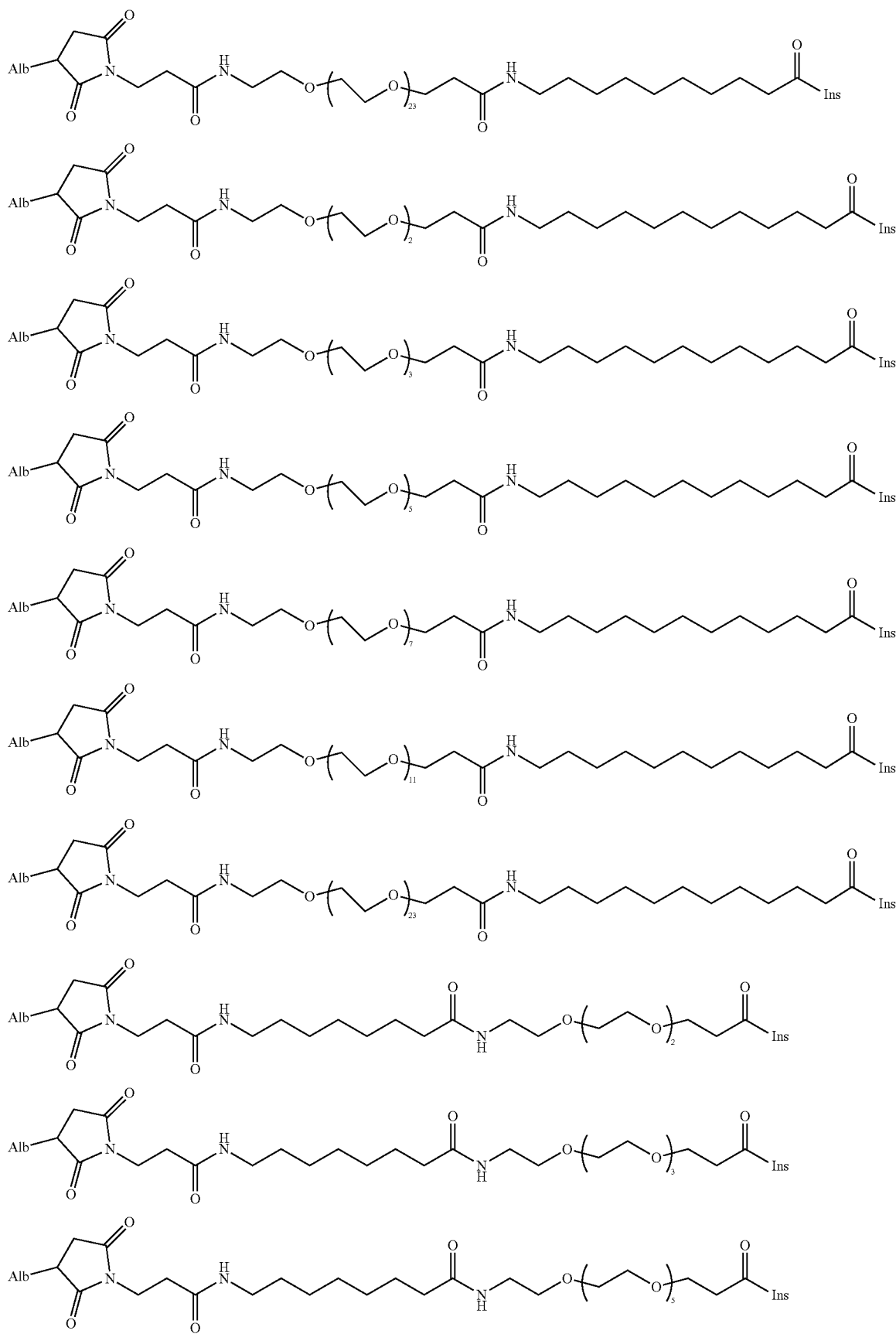

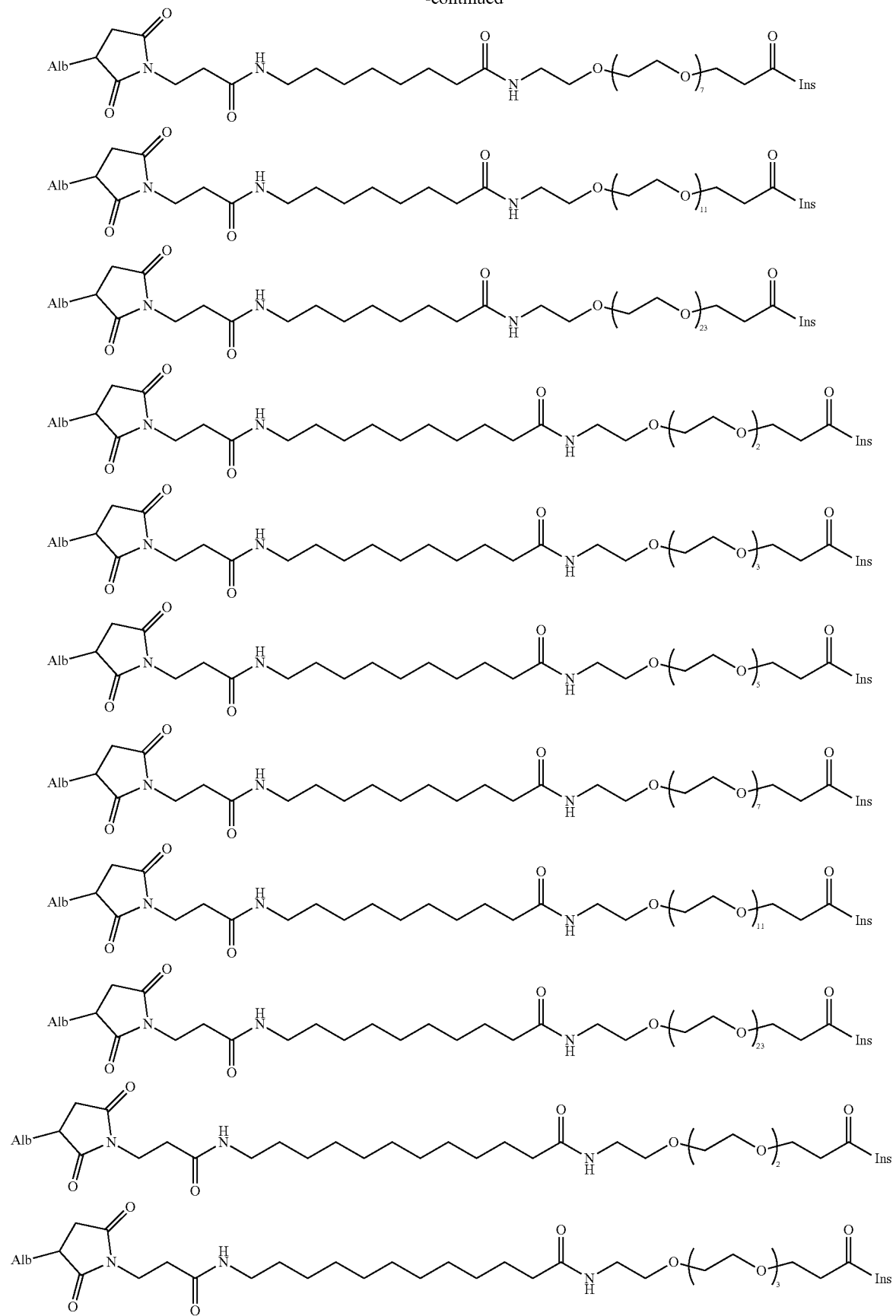

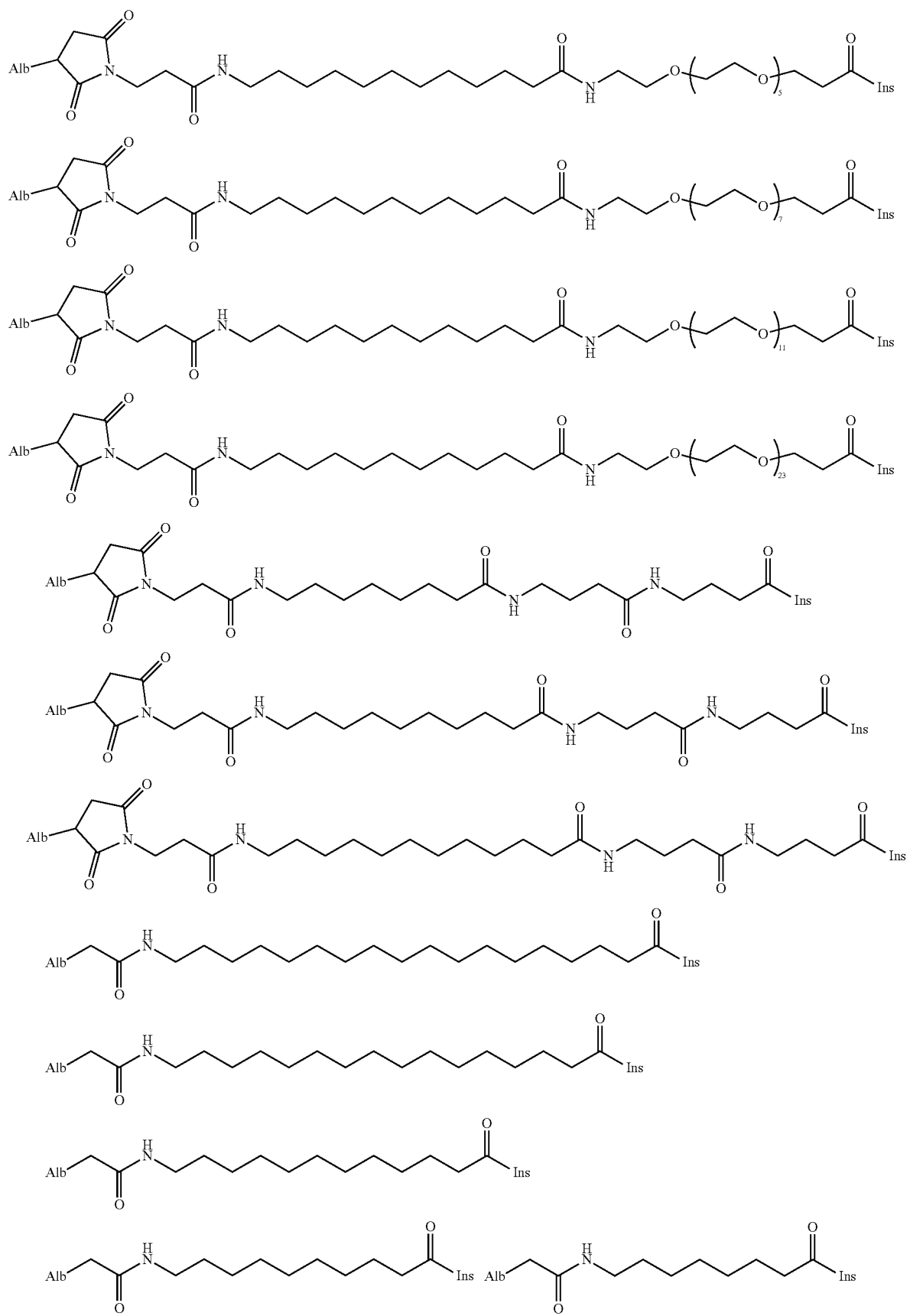

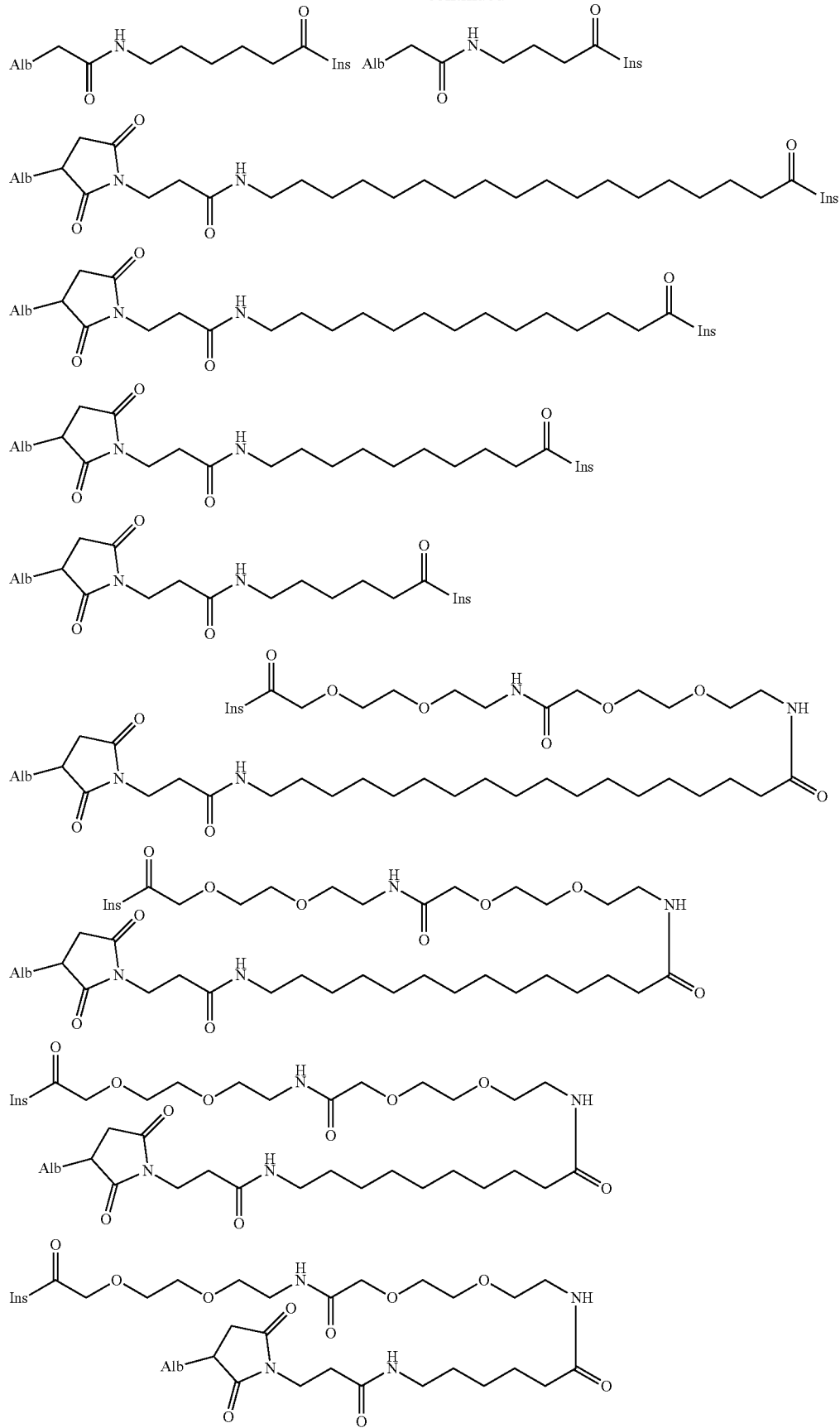

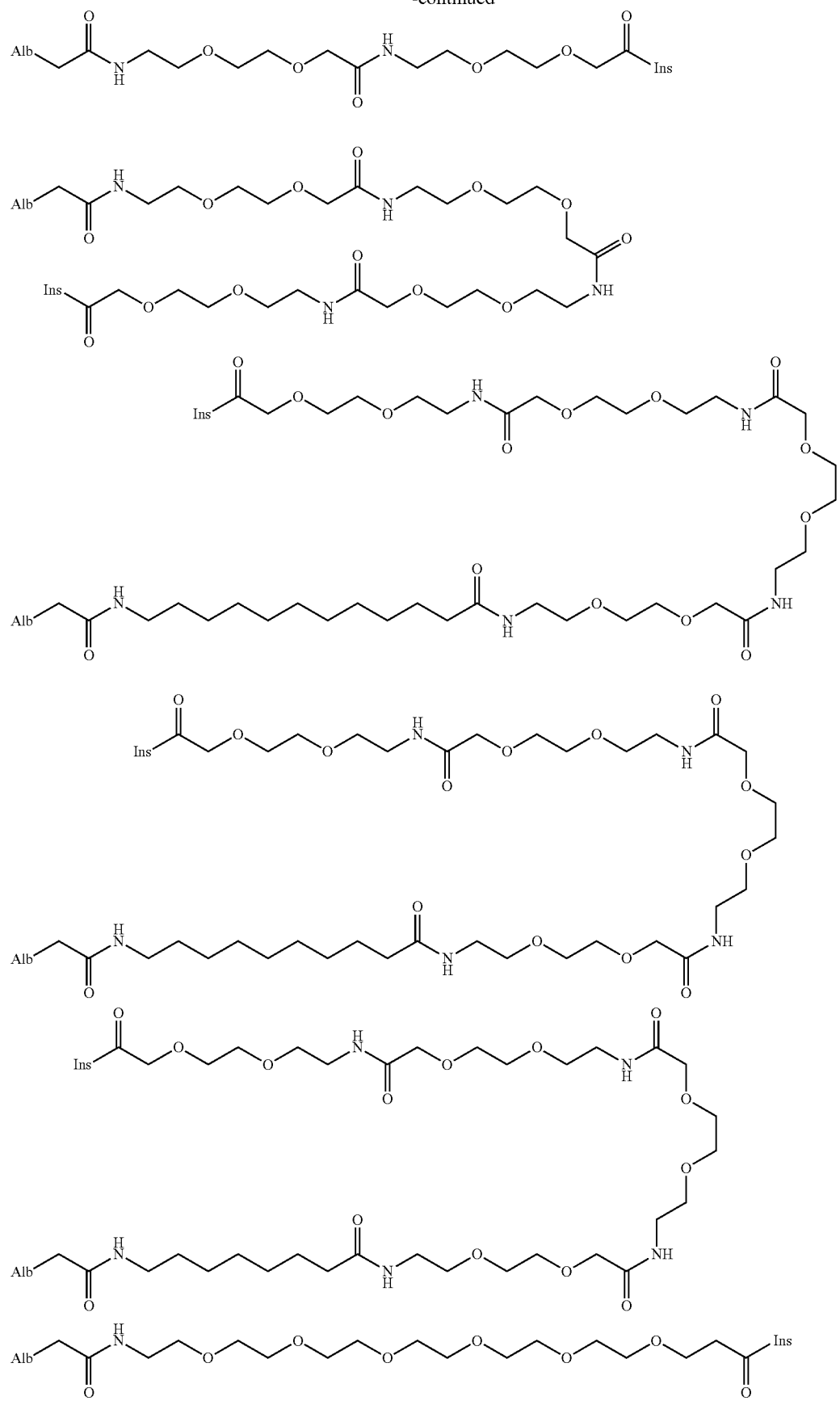

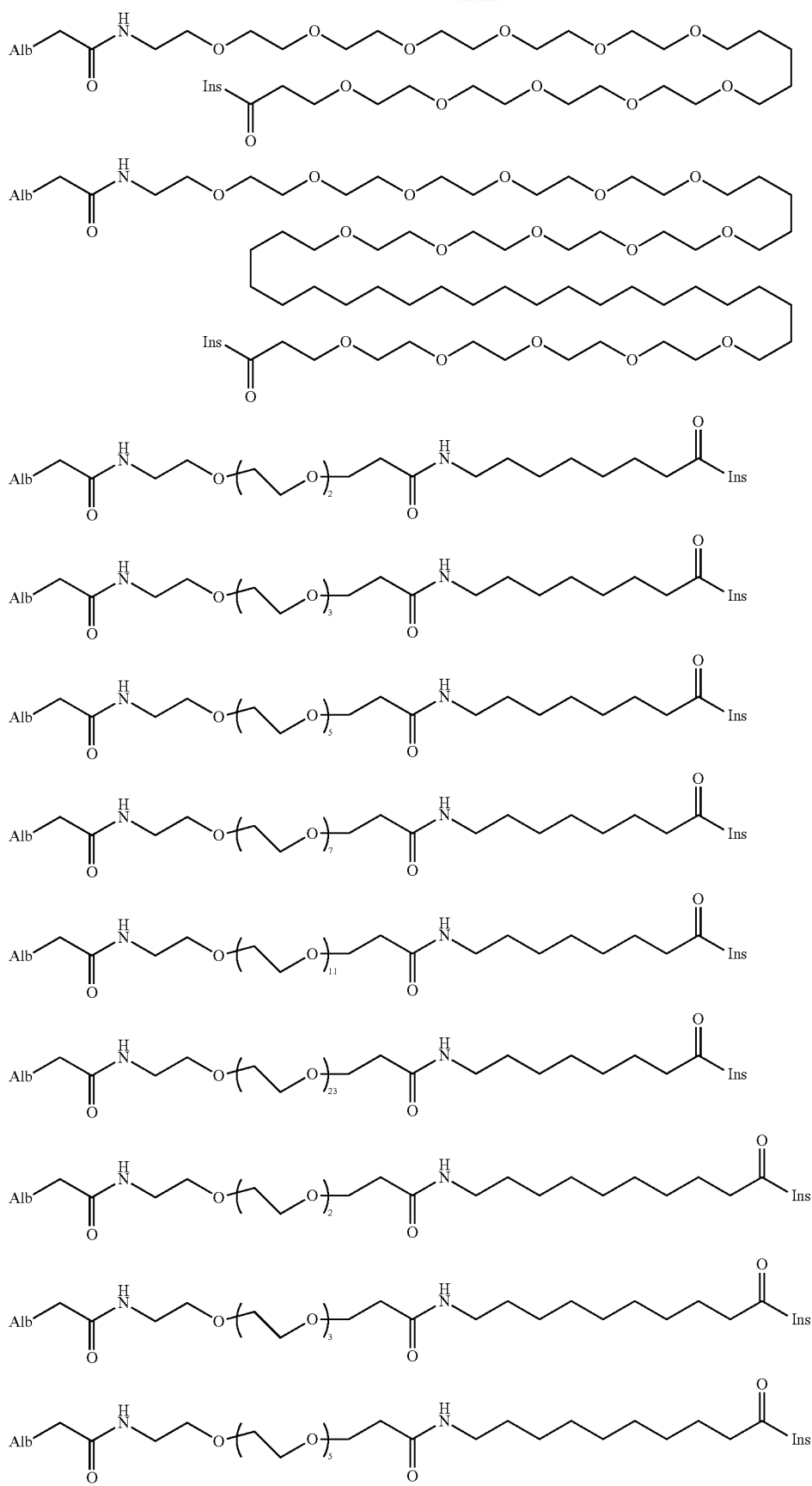

-continued
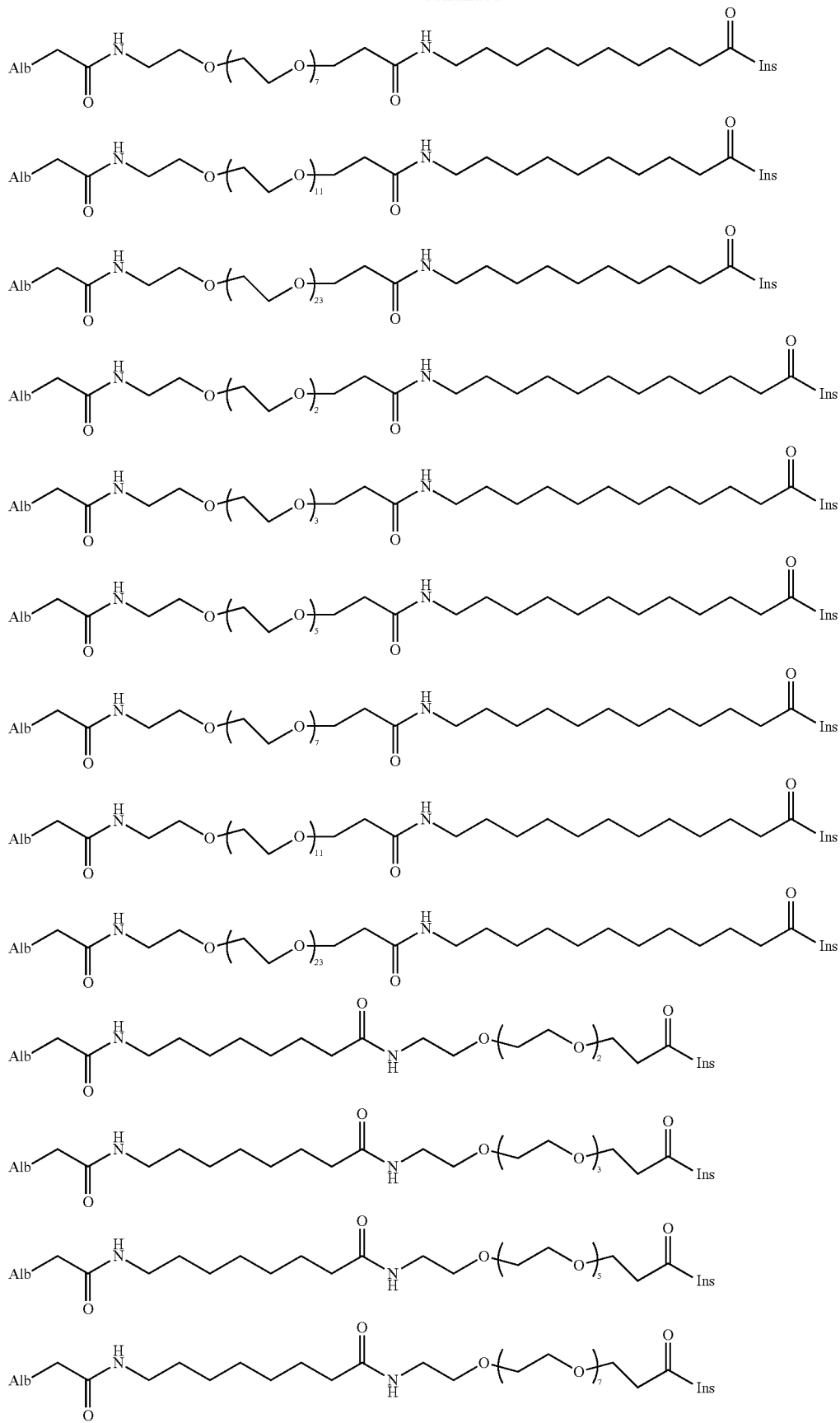

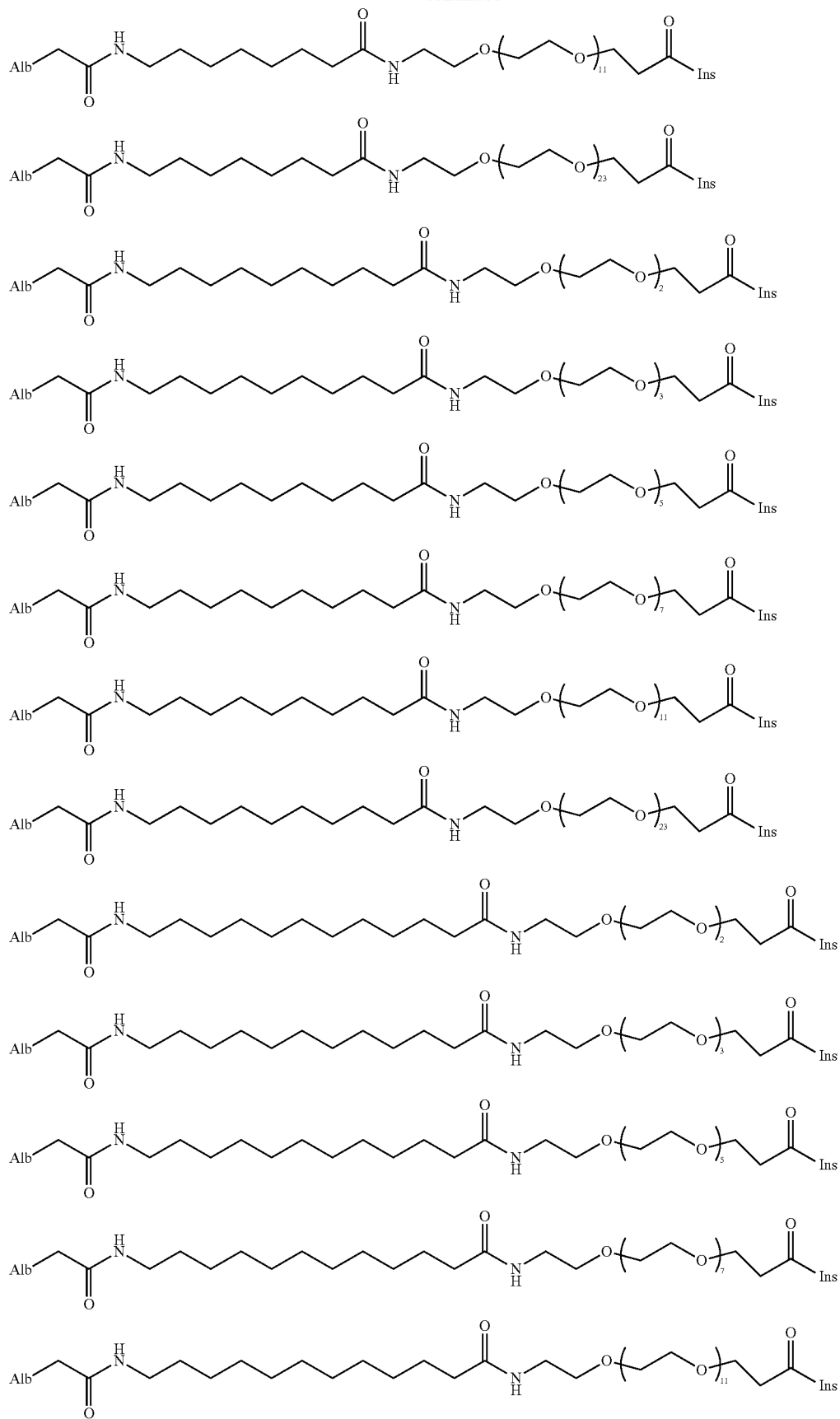

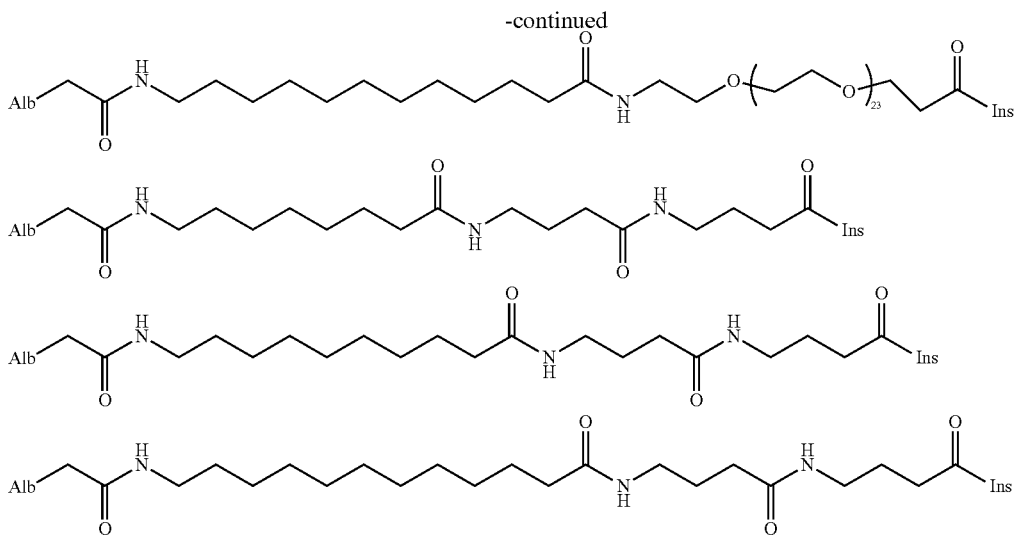

In one embodiment, the moiety of the general formula -M'-$Z_n$—$Y_o$— is selected from the group consisting of the moieties present in the above 126 non-limiting, specific examples of the insulin albumin conjugate according to this invention of the general formula III.

In another embodiment, the parent insulin present in the compounds of this invention can, apart from any lysine in position A22 and apart from any peptide residue connected C terminally to the A21 amino acid residue and apart from the B29R, and/or desB30 mutations, comprise one or more of the following mutations. Here, first the position in the A or B chain is given and, thereafter, the possible amino acid residue(s) is given as the one letter codes. In one embodiment, there are 6 mutations, in another embodiment, there are 5 mutations, in another embodiment, there are 4 mutations, in another embodiment, there are 3 mutations, in another embodiment, there are 2 mutations, in another embodiment, there is 1 mutation and in another embodiment, there is no mutation, apart from any lysine in position A22 and apart from any peptide residue connected C terminally to the A21 amino acid residue and apart from any B29R, and/or desB30 mutations:
A4: A or Q.
A5: L.
A8: R, N, Q, E, H, L or W.
A9: R or L.
A14: E or D.
A15: A or T.
A16: M.
A17: D or F.
A18: R, L, or V.
A21: G, A or K.
B3: A, R, H, I, L, M, F, W, Y, S or T.
B10: D or E.
B25: Y, H or desB25.
B26: Q, E, S or desB26.
B27: H, L, M, W or Y.
B28: D or E.

In another preferred embodiment the parent insulin of the invention comprise the A4A or A4Q mutations.

In another preferred embodiment the parent insulin of the invention comprises the A5L mutation.

In another preferred embodiment the parent insulin of the invention comprises the A8L, A8N, A8Q, A8E, A8H, A8L, or A8W mutation. In another preferred embodiment the parent insulin of the invention comprises the A8H mutation.

In another preferred embodiment the parent insulin of the invention comprises the A9R or A9L mutation. In another preferred embodiment the parent insulin of the invention comprises the A9L mutation.

In another preferred embodiment the parent insulin of the invention comprises the A14E or A14D mutation.

In another preferred embodiment the parent insulin of the invention comprises the A15A or A15T mutation.

In another preferred embodiment the parent insulin of the invention comprises the A16M mutation.

In another preferred embodiment the parent insulin of the invention comprises the A17D or A17F mutation.

In another preferred embodiment the parent insulin of the invention comprises the A18R, A18L, or A18V mutation. In another preferred embodiment the parent insulin of the invention comprises the A18L or A18V mutation.

In another preferred embodiment the parent insulin of the invention comprises the A21G or A21A mutation.

In another preferred embodiment the parent insulin of the invention comprises the B3A, B3R, B3H, B3I, B3L, B3M, B3F, B3W, B3Y, B3S or B3T mutation.

In another preferred embodiment the parent insulin of the invention comprises the B10D or B10E mutation.

In another preferred embodiment the parent insulin of the invention comprises the B25Y, B25H, or desB25 mutation.

In another preferred embodiment the parent insulin of the invention comprises the B26Q, B26E, B26S, or desB26 mutation.

In another preferred embodiment the parent insulin of the invention comprises the B27H, B27L, B27M, B27W, or B27Y mutation. In another preferred embodiment the parent insulin of the invention comprises the B27W or B27Y mutation.

In another preferred embodiment the parent insulin of the invention comprises the B28D or B28E mutation.

In another preferred embodiment the parent insulin of the invention comprises the A21Q, B1Q, desB1, B3Q, B3S, B3T, B13Q, or desB27 mutation.

Non-limiting specific examples of parent insulin analogues which may be present in the insulin albumin conjugates of this invention and which are one aspect of this invention comprise the following:

A21K, B29R, desB30 human insulin
A22K, B29R, desB30 human insulin
A14E, A22K, B25H, B29R, desB30 human insulin
A8H, A22K, B29R, desB30 human insulin
A18L, A22K, B29R, desB30 human insulin
A5L, A22K, B29R, desB30 human insulin
A8H, A18L, A22K, B29R, desB30 human insulin
A8H, A18L, A22K, B10E, B29R, desB30 human insulin
A5L, A8H, A17D, A18L, A22K, B10E, B29R, desB30 human insulin
A8H, A22K, B10E, B29R, desB30 human insulin
A5L, A8H, A17D, A22K, B10E, B29R, desB30 human insulin
A22K, B27Y, B29R, desB30 human insulin
A9L, A22K, B29R, desB30 human insulin
A4A, A22K, B29R, desB30 human insulin
A4Q, A22K, B29R, desB30 human insulin
A16L, A22K, B29R, desB30 human insulin
A17F, A22K, B29R, desB30 human insulin
A17D, A22K, B29R, desB30 human insulin
A18V, A22K, B29R, desB30 human insulin
A22K, B10D, B29R, desB30 human insulin
A22K, B10E, B29R, desB30 human insulin
A22K, B27W, B29R, desB30 human insulin
A22K, B27Y, B29R, desB30 human insulin
A22K, B28E, B29R, desB30 human insulin
A22K, B27Y, B28E, B29R, desB30 human insulin
A8H, A22K, B28E, B29R, desB30 human insulin
A22K, desB26, B28E, B29R, desB30 human insulin
A22K, desB25, B29R, desB30 human insulin
A22K, desB26, B29R, desB30 human insulin
A22K, B28E, B29R, desB30 human insulin
A22K, B28D, B29R, desB30 human insulin
A9L, A22K, B28E, B29R, desB30 human insulin
A4A, A22K, B28E, B29R, desB30 human insulin
A4Q, A22K, B28E, B29R, desB30 human insulin
A5L, A22K, B28E, B29R, desB30 human insulin
A16L, A22K, B28E, B29R, desB30 human insulin
A17F, A22K, B28E, B29R, desB30 human insulin
A17D, A22K, B28E, B29R, desB30 human insulin
A18V, A22K, B28E, B29R, desB30 human insulin
A22K, B10D, B28E, B29R, desB30 human insulin
A22K, B10E, B28E, B29R, desB30 human insulin
A22K, B27W, B28E, B29R, desB30 human insulin
A22G, A23K, B29R, desB30 human insulin
A22G, A23G, A24K, B29R, desB30 human insulin
A22G, A23G, A24G, A25K, B29R, desB30 human insulin
A21Q, A22G, A23G, A24K, B29R, desB30 human insulin
A21G, A22G, A23G, A24K, B29R, desB30 human insulin
A21Q, A22G, A23G, A24G, A25K, B29R, desB30 human insulin
A21G, A22G, A23G, A24G, A25K, B29R, desB30 human insulin
A21G, A22K, B29R, desB30 human insulin
A21G, A22G, A23K, B29R, desB30 human insulin
A21G, A22G, A23G, A24K, B29R, desB30 human insulin
A21G, A22G, A23G, A24G, A25K, B29R, desB30 human insulin
A21Q, A22K, B29R, desB30 human insulin
A21Q, A22G, A23K, B29R, desB30 human insulin
A21Q, A22G, A23G, A24K, B29R, desB30 human insulin
A21Q, A22G, A23G, A24G, A25K, B29R, desB30 human insulin
A14E, A21Q, A22K, B25H, B29R, desB30 human insulin
A14E, A21G, A22K, B25H, B29R, desB30 human insulin
A14E, A21Q, A22G, A23K, B25H, B29R, desB30 human insulin
A14E, A21G, A22G, A23K, B25H, B29R, desB30 human insulin
A14E, A21Q, A22G, A23G, A24K, B25H, B29R, desB30 human insulin
A14E, A21G, A22G, A23G, A24K, B25H, B29R, desB30 human insulin
A14E, A21Q, A22G, A23G, A24G, A25K, B25H, B29R, desB30 human insulin
A14E, A21G, A22G, A23G, A24G, A25K, B25H, B29R, desB30 human insulin
A22K, B3Q, B29R, desB30 human insulin
A22K, B3S, B29R, desB30 human insulin
A22K, B3T, B29R, desB30 human insulin
A22K, B1Q, B29R, desB30 human insulin
A18Q, A22K, B29R, desB30 human insulin
A22K, desB1, B3Q, B29R, desB30 human insulin
A22K, B28D, B29R, desB30 human insulin
A22K, desB27, B28E, B29R, desB30 human insulin
A22K, B28R, desB29, desB30 human insulin
A22K, B3Q, B28E, B29R, desB30 human insulin
A22K, B13Q, B29R, desB30 human insulin
A22K, desB1, B29R, desB30 human insulin
A21Q, A22G, A23K, B29R, desB30 human insulin
A21Q, A22G, A23G, A24K, B29R, desB30 human insulin
A21Q, A22G, A23G, A24G, A25K, B29R, desB30 human insulin
A21A, A22K, B29R, desB30 human insulin
A21A, A22G, A23K, B29R, desB30 human insulin
A21G, A22G, A23K, B29R, desB30 human insulin
A21A, A22G, A23G, A24K, B29R, desB30 human insulin
A21G, A22G, A23G, A24K, B29R, desB30 human insulin
A21G, A22G, A23G, A24G, A25K, B29R, desB30 human insulin
A21A, A22G, A23G, A24G, A25K, B29R, desB30 human insulin
A21Q, A22K, B3Q, B29R, desB30 human insulin
A21A, A22K, B3Q, B29R, desB30 human insulin
A21G, A22K, B3Q, B29R, desB30 human insulin The parent insulins can be prepared in a manner known per se. For example, they can be produced by expressing a DNA sequence encoding the single-chain insulin in question in a suitable host cell by well known technique as disclosed in e.g., EP 1,246,845. The insulin is expressed in a transformed host cell as a precursor molecule which is converted into the desired insulin molecule by enzymatic and chemical in vitro processes as disclosed in, e.g., EP 163,529 and EP 214,826. The precursor molecule may be expressed with an N-terminal extension which is later cleaved of as disclosed in, e.g., EP 1246,845. Examples of N-terminal extensions of the type suitable in the present invention are, e.g., disclosed in U.S. Pat. No. 5,395,922 and EP patent No. 765,395. More specifically, reference can be made to WO 2006/082205, from page 37, line 31, to page 39, line 29.

When a compound of the above general formula II is administered to a human, it conjugates with human serum albumin forming a compound of the above general formula III. Hence, both compounds of the above general formula II and compounds of the above general formula III can be used as a medicament, for example in the treatment of diabetes. Compounds of the general formula II and compounds of the general formula III can, collectively, be illustrate by the general formula IV:

$$A\text{-}Z_n\text{—}Y_o\text{-}Ins \qquad (IV)$$

wherein A has the same meaning as M and Alb-M'- collectively, and Z, n, Y, o, Ins, M, Alb and M' each are as defined herein.

Pharmaceutical Compositions

The compounds of this invention may be administered subcutaneously, nasally, orally, or pulmonary.

For subcutaneous administration, the compounds of this invention are formulated analogously with the formulation of known insulins. Furthermore, for subcutaneous administration, the compounds of this invention are administered analogously with the administration of known insulins and, generally, the physicians are familiar with this procedure.

The compounds of this invention may be administered by inhalation in a dose effective to increase circulating insulin levels and/or to lower circulating glucose levels. Such administration can be effective for treating disorders such as diabetes or hyperglycemia. Achieving effective doses of insulin requires administration of an inhaled dose of more than about 5 μg/kg to about 500 μg/kg of compounds of this invention. A therapeutically effective amount can be determined by a knowledgeable practitioner, who will take into account factors including insulin level, blood glucose levels, the physical condition of the patient, the patients pulmonary status, or the like.

The compounds of this invention may be delivered by inhalation to achieve slow absorption and/or reduced systemical clearance thereof. Different inhalation devices typically provide similar pharmacokinetics when similar particle sizes and similar levels of lung deposition are compared.

The compounds of this invention may be delivered by any of a variety of inhalation devices known in the art for administration of a therapeutic agent by inhalation. These devices include metered dose inhalers, nebulizers, dry powder generators, sprayers, and the like. Preferably, the compounds of this are delivered by a dry powder inhaler or a sprayer. There are a several desirable features of an inhalation device for administering compounds of this invention. For example, delivery by the inhalation device is advantageously reliable, reproducible, and accurate. The inhalation device should deliver small particles or aerosols, e.g., less than about 10 μm, for example about 1-5 μm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

As those skilled in the art will recognize, the formulation of compounds of this invention, the quantity of the formulation delivered and the duration of administration of a single dose depend on the type of inhalation device employed. For some aerosol delivery systems, such as nebulizers, the frequency of administration and length of time for which the system is activated will depend mainly on the concentration of compounds in the aerosol. For example, shorter periods of administration can be used at higher concentrations of compounds in the nebulizer solution. Devices such as metered dose inhalers can produce higher aerosol concentrations, and can be operated for shorter periods to deliver the desired amount of the compounds. Devices such as powder inhalers deliver active agent until a given charge of agent is expelled from the device. In this type of inhaler, the amount of compounds of this invention in a given quantity of the powder determines the dose delivered in a single administration.

The particle size of compounds of this invention in the formulation delivered by the inhalation device is critical with respect to the ability of insulin to make it into the lungs, and preferably into the lower airways or alveoli. Preferably, the compounds of this invention is formulated so that at least about 10% of the compounds delivered is deposited in the lung, preferably about 10 to about 20%, or more. It is known that the maximum efficiency of pulmonary deposition for mouth breathing humans is obtained with particle sizes of about 2 μm to about 3 μm. When particle sizes are above about 5 μm, pulmonary deposition decreases substantially. Particle sizes below about 1 μm cause pulmonary deposition to decrease, and it becomes difficult to deliver particles with sufficient mass to be therapeutically effective. Thus, particles of the compounds delivered by inhalation have a particle size preferably less than about 10 μm, more preferably in the range of about 1 μm to about 5 μm. The formulation of the compounds is selected to yield the desired particle size in the chosen inhalation device.

Advantageously for administration as a dry powder an compound of this invention is prepared in a particulate form with a particle size of less than about 10 μm, preferably about 1 to about 5 μm. The preferred particle size is effective for delivery to the alveoli of the patients lung. Preferably, the dry powder is largely composed of particles produced so that a majority of the particles have a size in the desired range. Advantageously, at least about 50% of the dry powder is made of particles having a diameter less than about 10 μm. Such formulations can be achieved by spray drying, milling, or critical point condensation of a solution containing the compound of this invention and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of compounds of this invention for administration from a dry powder inhaler typically include a finely divided dry powder containing the derivative, but the powder can also include a bulking agent, carrier, excipient, another additive, or the like. Additives can be included in a dry powder formulation of compound, e.g., to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patients airways. The compound can be mixed with an additive at a molecular level or the solid formulation can include particles of the compound mixed with or coated on particles of the additive. Typical additives include mono-, di-, and polysaccharides; sugar alcohols and other polyols, such as, e.g., lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the compounds of this invention can be produced by forcing a suspension or solution of the compound through a nozzle under pressure. The nozzle size and configuration, the applied pressure, and the liquid feed rate can be chosen to achieve the desired output and particle size. An electrospray can be produced, e.g., by an electric field in connection with a capillary or nozzle feed. Advantageously, particles of insulin conjugate delivered by a sprayer have a particle size less than about 10 μm, preferably in the range of about 1 μm to about 5 μm.

Formulations of compounds of this invention suitable for use with a sprayer will typically include the compounds in an aqueous solution at a concentration of from about 1 mg to about 500 mg of the compound per ml of solution. Depending on the compound chosen and other factors known to the medical advisor, the upper limit may be lower, e.g., 450, 400, 350, 300, 250, 200, 150, 120, 100 or 50 mg of the compound per ml of solution. The formulation can include agents such as an excipient, a buffer, an isotonicity agent, a preservative, a surfactant, and, preferably, zinc. The formulation can also include an excipient or agent for stabilization of the compound, such as a buffer, a reducing agent, a bulk protein, or a carbohydrate. Bulk proteins useful in formulating insulin conjugates include albumin, protamine, or the like. Typical carbohydrates useful in formulating the compound include sucrose, mannitol, lactose, trehalose, glucose, cyclodextrin or the like. The compounds formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

Pharmaceutical compositions containing an compound of this invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump.

Injectable compositions of the compounds of this invention can be prepared using the conventional techniques of the pharmaceutical industry which involve dissolving and mixing the ingredients as appropriate to give the desired end product. Thus, according to one procedure, an compound is dissolved in an amount of water which is somewhat less than the final volume of the composition to be prepared. Zink, an isotonic agent, a preservative and/or a buffer is/are added as required and the pH value of the solution is adjusted—if necessary—using an acid, e.g., hydrochloric acid, or a base, e.g., aqueous sodium hydroxide as needed. Finally, the volume of the solution is adjusted with water to give the desired concentration of the ingredients.

In a further embodiment of this invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, acetic acid and other organic acids or their salts, or mixtures thereof. Each one of these specific buffers constitutes an alternative embodiment of this invention.

In a further embodiment of this invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)-1,2-propanediol) or mixtures thereof. In a further embodiment of this invention the preservative is present in a concentration from about 0.1 mg/ml to 20 mg/ml. In a further embodiment of this invention the preservative is present in a concentration from about 0.1 mg/ml to 5 mg/ml. In a further embodiment of this invention the preservative is present in a concentration from about 5 mg/ml to 10 mg/ml. In a further embodiment of this invention the preservative is present in a concentration from about 10 mg/ml to 20 mg/ml. Each one of these specific preservatives constitutes an alternative embodiment of this invention. The use of a preservative in pharmaceutical compositions is well-known to the skilled person. For convenience reference is made to Remington: *The Science and Practice of Pharmacy,* $19^{th}$ edition, 1995.

In a further embodiment of this invention, the formulation further comprises an isotonic agent which may be selected from the group consisting of a salt (e.g., sodium chloride), a sugar or sugar alcohol, an amino acid (for example, L-glycine, L-histidine, arginine, lysine, isoleucine, aspartic acid, tryptophan or threonine), an alditol (e.g. glycerol (glycerine), 1,2-propanediol (propyleneglycol), 1,3-propanediol or 1,3-butanediol), polyethyleneglycol (e.g., PEG400) or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a $C_4$-$C_8$ hydrocarbon having at least one —OH group and includes, e.g., mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of this invention. In one embodiment, the sugar or sugar alcohol concentration is between about 1 mg/ml and about 150 mg/ml. In a further embodiment of this invention the isotonic agent is present in a concentration from about 1 mg/ml to 50 mg/ml. In a further embodiment of this invention the isotonic agent is present in a concentration from about 1 mg/ml to 7 mg/ml. In a further embodiment of this invention the isotonic agent is present in a concentration from about 8 mg/ml to 24 mg/ml. In a further embodiment of this invention the isotonic agent is present in a concentration from about 25 mg/ml to 50 mg/ml. Each one of these specific isotonic agents constitutes an alternative embodiment of this invention. The use of an isotonic agent in pharmaceutical compositions is well-known to the skilled person. For convenience reference is made to Remington: *The Science and Practice of Pharmacy,* $19^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an compounds of this invention may, e.g., be prepared as described in European Patent No. 272,097.

Compositions containing compounds of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the compound of this invention be determined for each individual patient by those skilled in the art in a similar way as for known insulin compositions.

Preferred Features of this Invention

To sum up and supplement the statements herein, the features of this invention are as follows:

1. A compound of the general formula (III):

$$\text{Alb-M'-}Z_n\text{—}Y_o\text{-Ins} \qquad \text{(III)}$$

wherein

Ins represents insulin or an insulin analogue as defined herein from which, formally, a hydrogen atom has been removed from an amino group present in the C-terminal lysine residue in the A-chain;

M' represents the thiol reactive group designated M after reaction with a thiol group of Alb (albumin), M represents a Michael acceptor represented by a malimido group, a vinylsulfone or the like, a thiol reactive group represented by iodide, pyridyldisulfide, methoxy- or ethoxycarbonyldisulfide and o-nitro-phenyldisulphide;

Z is a covalent bond or represents a moiety of one of the following formula:

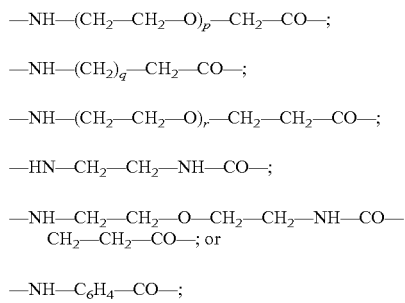

p is 0 (zero) or an integer in the range from 1 to 24;
q is 0 (zero) or an integer in the range from 1 to 24;
r is 0 (zero) or an integer in the range from 1 to 24;
—$C_6H_4$— is para-phenylene;
n represents an integer in the range from 1 to 10 or more preferably 1 or 2
Y has one of the meanings given for Z;
o is 0 to 10 or more preferably 0, 1 or 2; and
Alb represents albumin as defined herein.

2. A compound of the general formula (IIIa): Alb-M'-$(CH_2)_m$—CO—$Z_n$—$Y_o$—CO-Ins (IIIa) wherein M' is the thiol-reactive group (M) after reaction with a thiol-group of albumin, wherein M is a Michael acceptor represented by a malimido group, a vinylsulfone or the like, a thiol reactive group represented by iodide, pyridyldisulfide, methoxy- or ethoxycarbonyldisulfide and o-nitrophenyldisulphide; m is an integer in the range from 1 to 5; Z is chosen from the following six moieties: —NH—$(CH_2$—$CH_2$—X$)_p$—$CH_2$—CO—; —NH—$CH_2$—$CH_2$—O—$CH_2$—CO—; —HN—$CH_2$—$CH_2$—NH—; —NH—$CH_2$—$CH_2$—O—$CH_2$—$CH_2$—NH—CO—$CH_2$—$CH_2$—CO—; —NH—$CH_2$—$CH_2$—O—$CH_2$—$CH_2$—O—$CH_2$—CO—; and —NH—$C_6H_4$—CO—; X is —O— or —$CH_2$—; p is 0 or an integer in the range from 1 to 24; —$C_6H_4$— is para-phenylene; n is an integer in the range from 1 to 10 or more preferably 1 or 2; Y is defined as Z or a covalent bond; o is 0 or an integer in the range from 1 to 10 or more preferably 0 or 1; and Alb is albumin as defined herein, preferably linked through a free thiol group of a Cys residue.

3. A compound of the general formula III or IIIa wherein Z is chosen from the following moieties of the following formulae: —NH—$(CH_2$—$CH_2$—X$)_p$—$CH_2$—CO—; —NH—$CH_2$—$CH_2$—O—$CH_2$—CO—; —HN—$CH_2$—$CH_2$—NH—; —NH—$CH_2$—$CH_2$—O—$CH_2$—$CH_2$—NH—CO—$CH_2$—$CH_2$—CO—; —NH—$CH_2$—$CH_2$—O—$CH_2$—$CH_2$—O—$CH_2$—CO—; or —NH—$C_6H_4$—CO—; wherein X is —O— or —$CH_2$—; m is an integer in the range from 1 to 5, and Alb, M', n, Y, o, W and Ins are each as defined in clause 1.

4. A compound according to any one of the above clauses wherein Ins is an insulin analogue with a lysine residue in the C-terminal end of the A-chain, optionally with a lysine residue in the C-terminal end of a peptide residue or the lysine residue connected C-terminally to the A21 amino acid residue.

5. A compound according to the above clause wherein Ins is an insulin analogue with a lysine residue in C-terminal end of the A-chain, optionally with a lysine residue in the C-terminal end of an amino acid extension of the A-chain C-terminal.

6. A compound according to any one of the above clauses to the extent possible wherein the amino acid residue in position A22 of Ins is the C terminal amino acid residue and the A22 amino acid residue is K (Lys).

7. A compound according to any one of the above clauses to the extent possible wherein the amino acid residue in position A22 of Ins is the C terminal amino acid residue and the A22 amino acid residue is K (Lys) and A18 is L (Leu).

8. A compound according to any one of the above clauses to the extent possible wherein the amino acid residue in position A23 of Ins is the C terminal amino acid residue and the A23 amino acid residue is K (Lys).

9. A compound according to any one of the preceding clauses to the extent possible wherein the amino acid residue in position A22 is G.

10. A compound according to the preceding clauses wherein the amino acid residue in position B29 is R (Arg).

11. A compound according to the preceding clauses wherein the amino acid residue in position B30 is deleted 12. A compound according to any one of the above clauses to the extent possible, wherein Ins is A22K, B29R, desB30 human insulin; A22G, A23K, B29R, desB30 human insulin; A22G, A23G, A24K, B29R, desB30 human insulin; A22G, A23G, A24G, A25K, B29R, desB30 human insulin; or A21Q, A22-39G, A40K, B29R, desB30 human insulin.

13. A compound according to the above clause wherein the amino acid residue in position A21 of Ins is the C terminal amino acid residue and the A21 amino acid residue is K (Lys).

14. A compound according to the above clause wherein the amino acid residue in position A18 of Ins is L (Leu).

15. An insulin albumin conjugate according to the above clause wherein the amino acid residue in position A21 of Ins is the C terminal amino acid residue and the A21 amino acid residue is K (Lys) and A18 is L (Leu).

16. A compound according to any one of the above clauses to the extent possible wherein the amino acid residue in position A5 of Ins is L (Leu).

17. An insulin albumin conjugate according to any one of the above clauses wherein M' is

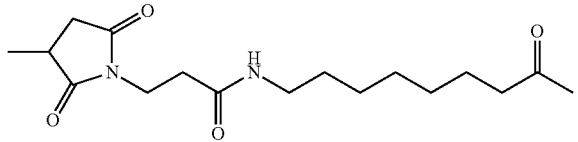 [SMILES: CC(=O)CCCCCCCNC(=O)CCN1C(=O)CC(C)C1=O]

18. A compound according to any one of the above clauses to the extent possible wherein m is 2.

19. A compound according to any one of the above clauses to the extent possible wherein t is 2.

20. An insulin albumin conjugate according to any one of the above clauses to the extent possible wherein M' is —$CH_2$—CO—.

21. A compound according to any one of the above clauses to the extent possible wherein Z is the moiety —NH—$CH_2$—$CH_2$—$CH_2$—$CH_2$—$CH_2$—$CH_2$—$CH_2$—CO—.

22. A compound according to any one of the above clauses to the extent possible wherein Z is the moiety —NH—$CH_2$—$CH_2$—$CH_2$—$CH_2$—$CH_2$—$CH_2$—$CH_2$—$CH_2$—$CH_2$—$CH_2$—CO—.

23. A compound according to any one of the above clauses to the extent possible wherein n is 1.
24. A compound according to any one of the above clauses to the extent possible wherein Y is a covalent bond
25. A compound according to any one of the above clauses to the extent possible wherein Y is NH—CH$_2$—CH$_2$—O—CH$_2$—CH$_2$—O—CH$_2$—CO—;
26. A compound according to any one of the above clauses to the extent possible wherein o is 2
27. A compound according to any one of the above clauses to the extent possible wherein Alb is human serum albumin or Albagen (human serum albumin with deletion of the N-terminal residue (Asp)).
28. A compound of the general formula II:

$$M\text{-}Z_n\text{—}Y_o\text{-}Ins \quad (II)$$

wherein M, Z, n, Y, o and Ins each are as defined herein, especially as defined in the clauses.
29. A compound according to any one of the preceding product clauses to the extent possible, which is any one of the compounds mentioned specifically in this specification such as in the specific examples, especially any one of the examples 1 et seq. below.
30. The use of a compound according to any one of the preceding product clauses to the extent possible for the preparation of a pharmaceutical composition for the treatment of diabetes.
31. The use of a compound according to any one of the preceding product clauses to the extent possible for the preparation of a pharmaceutical composition which can be administered subcutaneously for the treatment of diabetes.
32. The use of a compound according to any one of the preceding product clauses to the extent possible for the preparation of a pharmaceutical composition which can be administered subcutaneously for the treatment of diabetes and which gives a long acting effect.
33. The use of a compound according to any one of the preceding product clauses to the extent possible for the preparation of a pharmaceutical composition which can be administered pulmonary for the treatment of diabetes.
34. The use of a compound according to any one of the preceding product clauses to the extent possible for the preparation of a pharmaceutical composition which can be administered pulmonary for the treatment of diabetes and which gives a long acting effect.
35. The use of a compound according to any one of the preceding product clauses to the extent possible for the preparation of a powder pharmaceutical composition which can be administered pulmonary for the treatment of diabetes.
36. The use of a compound according to any one of the preceding product clauses to the extent possible for the preparation of a liquid pharmaceutical composition which can be administered pulmonary for the treatment of diabetes.
37. The use of a compound according to any one of the preceding product clauses to the extent possible for the preparation of a pharmaceutical composition which can be administered orally for the treatment of diabetes.
38. A method of treatment of diabetes, the method comprising administering to a subject in need thereof a therapeutically effective amount of a compound according to any one of the preceding product clauses.
39. A composition containing human insulin as well as a compound according to any one of the preceding clauses.
40. A composition containing insulin aspart as well as a compound according to any one of the preceding clauses.
41. A composition containing insulin Lispro as well as a compound according to any one of the preceding clauses.
42. A composition containing insulin Glulisine as well as a compound according to any one of the preceding clauses.
43. A pharmaceutical composition comprising a biologically active amount of the insulin analogue according to any one of the above clauses to the extent possible relating to insulin analogs and a pharmaceutically acceptable carrier.
44. A method for the treatment, prevention or alleviation of hyperglycemia, type 2 diabetes, impaired glucose tolerance, type 1 diabetes, obesity, syndrome X or dyslipidemia in a subject comprising administering to a subject an insulin analogue according to any one of the above clauses relating to insulin analogs or a pharmaceutical composition according to any one of the above clauses.
45. Use of a therapeutically effective amount of an insulin analogue according to any one of the above clauses to the extent possible relating to insulin analogs for the preparation of a pharmaceutical formulation for the treatment or prevention of hyperglycemia, type 2 diabetes, impaired glucose tolerance, type 1 diabetes, obesity, syndrome X or dyslipidemia.
46. A method of treatment of diabetes, the method comprising administering to a subject in need thereof a therapeutically effective amount of an insulin albumin conjugate according to any one of the preceding product clauses.

Combining one or more of the clauses described herein, optionally also with one or more of the claims below, results in further clauses and the present invention relates to all possible combinations of said clauses and claims.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

EXAMPLES

The following examples are offered by way of illustration, not by limitation.
General Methods
LCMS Method
A Waters Micromass ZQ mass spectrometer was used to identify the mass of the sample after elution from a Waters Alliance HT HPLC system.

Eluents:
A: 0.1% Trifluoro acetic acid in water
B: 0.1% Trifluoro acetic acid in acetonitrile
Column: Phenomenex, Jupiter C4 50×4.60 mm id 5 μm
Gradient: 10%-90% B over 7.5 min at 1.0 ml/min Example 1

A22K[N$^\epsilon$8-{3-(Albagen-Cys34-yl-2,5-dioxopyrrolidin-1-yl)propionylamino}octanoyl], B29R, desB30 Human Insulin

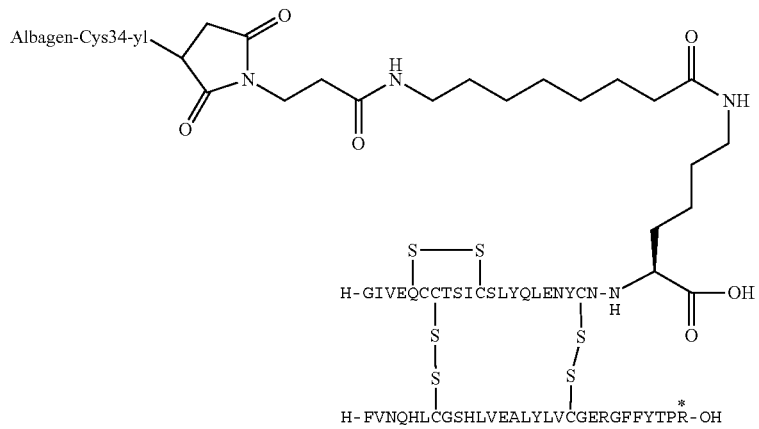

Step 1: A22K(N$^\epsilon$-8-[3-(2,5-Dioxo-2,5-dihydropyrrol-1-yl)propionylamino]octanoyl), B29R, desB30 Human Insulin A22K, B29R, desB30 Human insulin (WO 2007096431) (1.00 g) was dissolved in DMSO (80 ml) and triethylamine (0.50 ml). 8-[3-(2,5-Dioxo-2,5-dihydropyrrol-1-yl)propionylamino]octanoic acid 2,5-dioxopyrrolidin-1-yl ester (84 mg) dissolved in THF (8.35 ml) was added. After 165 min a few drops of TFA, A- and B-buffer (see below) was added to give 150 ml at pH 5-6.
Purification by preparative HPLC: C18, 3 cm column (Gemini), A-buffer 0.1% TFA in MiliQ water, B-buffer: 0.1% TFA in AcCN, flow 20 ml/min, gradient 20-40% B over 60 min.
Yield 117 mg, MALDI: 6152.89.

Step 2: A22K[N$^\epsilon$8-[3-(Albagen-Cys34-yl-2,5-dioxopyrrolidin-1-yl)propionylamino]octanoyl], B29R, desB30 Human Insulin Albagen (vial of 200 mg custom made by New Century Pharmaceuticals, Inc. recombinant not stabilized, freeze-dried from water) was dissolved in reaction buffer (0.15 M Na$_2$HPO$_4$ pH 6.5, 2% mannitol, 5 ml). A solution of A22K-(N$^\epsilon$-8-[3-(2,5-dioxo-2,5-dihydropyrrol-1-yl)propionylamino]octanoyl) B29R, desB30 human insulin (18.5 mg) in 10% acetic acid (0.50 ml) was added under precipitation. pH was adjusted to 7.0 with 1 N NaOH to give an almost clear reaction mixture. The mixture was stirred slowly at room temperature for 4-6 h. Ammonium sulphate (1 g) was added and the mixture was filtered through a Millex 0.22 μm filter. Purification was performed on an Äkta Purifier using a HIC-ISO (25 ml) column. A-buffer, 0.05 M Na$_2$HPO$_4$, 2 M ammonium sulphate, pH 7, 2% mannitol: B-buffer, 0.05 M Na$_2$HPO$_4$, pH 7, 2% mannitol. Gradient 0-100% B over 20 CV. Flow 10 ml/min. The fractions containing the conjugate were pooled and concentrated by centrifugation using Vivaspin 20, 30000 MWCO tubes at 3000 g. The concentrated product was desalted using a HiPrep 26/10 column and B-buffer. The collected fractions were concentrated once more by ultra filtration using Vivaspin 20, 30000 MWCO tubes at 3000 g. The product was stored in the buffer in the freezer. The concentration was determined by absorbance measurements using the extinction coefficient: 41479. LC-MS, M/z: 1960.0 (M+37), combined: 72478.

8-[3-(2,5-Dioxo-2,5-dihydropyrrol-1-yl)propionylamino]octanoic acid 2,5-dioxopyrrolidin-1-yl ester Step 1: 3-(2,5-Dioxo-2,5-dihydropyrrol-1-yl)propionic acid 2,5-dioxopyrrolidin-1-yl ester Malimidopropionic acid (500 mg) was dissolved in dry THF (15 ml). TSTU (790 mg) and DIPEA (0.62 ml) was added. The mixture was stirred at room temperature under nitrogen over night. The yellow thick suspension was concentrated. The residue was dissolved in DCM and extracted with 0.1 N HCl (2×) and brine (1×). The organic layer was dried (Na$_2$SO$_4$) and concentrated to give a white solid. LC-MS, M/z: 267.26 (M+1).

Step 2: 8-[3-(2,5-Dioxo-2,5-dihydropyrrol-1-yl)propionylamino]octanoic acid 3-(2,5-Dioxo-2,5-dihydropyrrol-1-yl)propionic acid 2,5-dioxopyrrolidin-1-yl ester (787 mg, crude) was dissolved in DMF (15 ml). 8-Aminooctanoic acid (350 mg) and DIPEA (0.45 ml) was added. The mixture was stirred under nitrogen at room temperature over night. The mixture was concentrated. The residue was dissolved in EtOAc and extracted with 0.1 N HCl (2×). The phase separation was not easy. The organic layer was washed with brine (2×), dried (Na$_2$SO$_4$) and concentrated to give a white solid. LC-MS, M/z: 311.34 (M+1).

Step 3: 8-[3-(2,5-Dioxo-2,5-dihydropyrrol-1-yl)propionylamino]octanoic acid 2,5-dioxopyrrolidin-1-yl ester To a solution of 8-[3-(2,5-dioxo-2,5-dihydropyrrol-1-yl)propionylamino]octanoic acid (917 mg, crude) in dry THF (15 ml) was added TSTU (1.07 mg) and DIPEA (0.65 ml). The mixture was stirred under nitrogen over night. The mixture was concentrated. To the residue was added EtOAc and the precipitate was filtered off. The filtrate was extracted with 0.1 N HCl (2×) and brine (1×), dried (Na$_2$SO$_4$) and concentrated to give an off-white solid. Overall yield 37% (444 mg). LC-MS, M/z: 408.39 (M+1).

Example 2

A22K[N$^\epsilon$-12-{2-(Albagen-Cys34-ylacetylamino)}dodecanoyl] B29R, desB30 Human Insulin

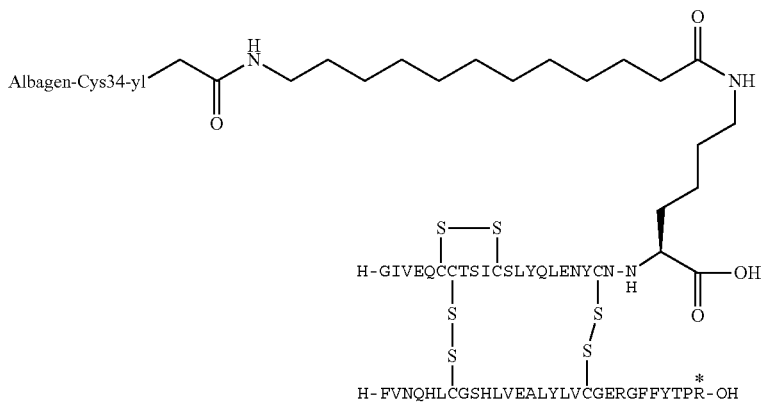

Step 1: A22K(N$^\epsilon$-12-(2-Iodoacetylamino)dodecanoyl), B29R, desB30 Human Insulin To a solution of A22K, B29R, desB30 Human insulin (WO 2007096431) (1.00 g) in 0.1 M sodium carbonate (20 ml) and ethanol (10 ml), pH 10.6, was added a solution of 12-(2-Iodoacetylamino)dodecanoic acid 2,5-dioxopyrrolidin-1-yl ester (99 mg) in THF (0.5 ml). pH of the reaction mixture was kept at 10.6. After gentle stirring for 30 min, water (50 ml) was added and pH was adjusted to 5.5 with 1 N HCl to give precipitation. The product was spinned down at 3000 g for 10 min. The supernatant was discarded and the solid product was purified by preparative HPLC: C18, 3 cm column (Gemini), A-buffer 0.1% TFA in MiliQ water, B-buffer: 0.1% TFA in AcCN, flow 25 ml/min, gradient 25-60% B over 45 min.

Yield 330 mg, MALDI: 6228.21.

Step 2: A22K[N$^\epsilon$-12{[2-Albagen-Cys34-ylacetylamino}dodecanoyl] B29R, desB30 Human Insulin Albagen (vial of 200 mg custom made by New Century Pharmaceuticals, Inc. recombinant not stabilized, freeze-dried from water) was dissolved in reaction buffer (0.15 M $Na_2HPO_4$ pH 7.0, 2% mannitol, 3 ml). A solution of A22K (N$^\epsilon$-12-(2-iodoacetylamino)dodecanoyl), B29R, desB30 human insulin (20 mg) in reaction buffer/acetonitrile 1:1 (2.0 ml) was added to give a solution. pH was 7.3. The mixture was stirred slowly at room temperature in dark over night. Ammonium sulphate (1 g) was added and the mixture was filtered through a Millex 0.22 μm filter. Purification was performed as described in Example 1. The product was stored in B-buffer in the freezer. The concentration was determined by absorbance measurements using the extinction coefficient: 41479. LC-MS, M/z: 1542.29 (M+47), combined: 72430.

12-(2-Iodoacetylamino)dodecanoic acid 2,5-dioxopyrrolidin-1-yl ester

Step 1: 12-(2-Iodoacetylamino)dodecanoic acid

Iodoacetic acid (1.00 g) was dissolved in dichloromethane and kept in the dark. TSTU (1.62 g) and DIPEA (1.03 ml) was added. After stirring for 45 min a suspension of 12-aminododecanocic acid (1.14 g) in NMP (10 ml) and DIPEA (1.03 ml) was added. After stirring for 4 h the mixture was pored into 0.5 N HCl (300 ml) and extracted with dichloromethane. The organic layer was washed with 0.1 N HCl, dried with magnesium sulphate and concentrated to give an oil. The residue was dissolved in a mixture of diethyl ether and ethyl acetate, washed with water, dried with magnesium sulphate and concentrated to give a solid. This solid was triturated in diethyl ether and filtered to give a powder. Yield 1.05 g, 50%. LC-MS, M/z: 384.2 (M+1).

Step 2: 12-(2-Iodoacetylamino)dodecanoic acid 2,5-dioxopyrrolidin-1-yl ester To a solution of 12-(2-Iodoacetylamino)dodecanoic acid (460 mg) in THF (10 ml) was added TSTU (415 mg) and DIPEA (0.315 ml). After stirring at room temperature for 2 h, the mixture was pored in to 0.5 N HCl (200 ml) and was extracted with ethyl acetate (2×200 ml). The combined organic layers was washed with 0.1 N HCl and brine, dried with magnesium sulphate and concentrated. The residue was used without further purification. Yield, 99% (575 mg). LC-MS, M/z: 481.2 (M+1).

Example 3

A22K[N$^\epsilon$-{2-[2-(2-{2-[2-(12-{2-Albagen-Cys-34-ylacetylamino}dodecanoylamino)ethoxy]ethoxy}acetylamino)ethoxy]ethoxy}acetyl] B29R, desB30 Human Insulin

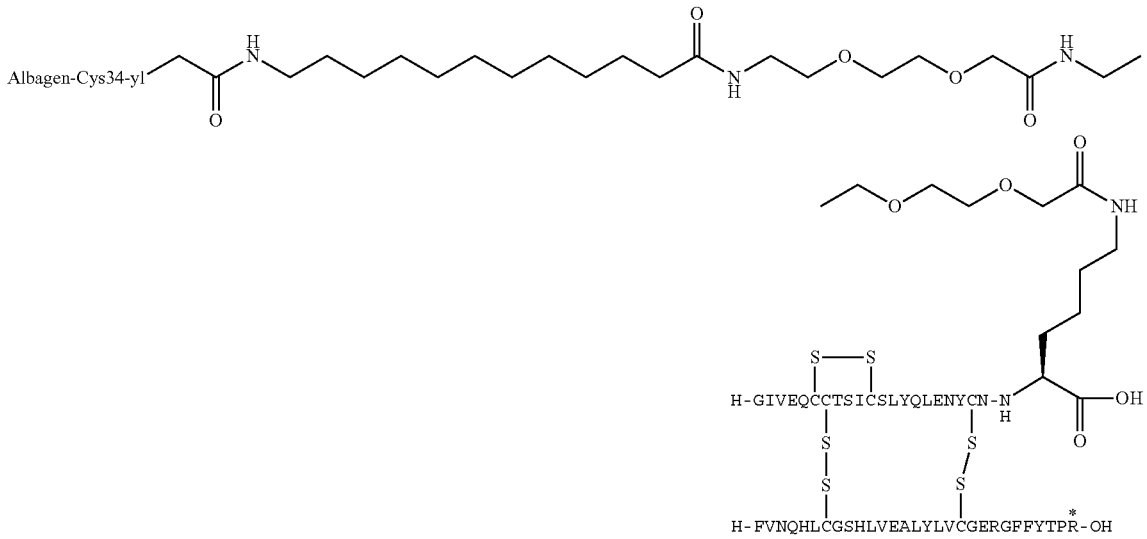

Step 1: A22K[N$^\epsilon$-{2-[2-(2-{2-[2-(12-{2-Iodoacetylamino}dodecanoylamino)ethoxy]ethoxy}acetylamino)-ethoxy]ethoxy}acetyl] B29R, desB30 Human Insulin To a solution of A22K, B29R, desB30 human insulin (WO 2007096431) (0.800 g) in 0.1 M sodium carbonate (16 ml) at pH 10.5, was added a solution of (2-{2-[2-(2-{2-[12-(2-Iodoacetylamino)dodecanoylamino]ethoxy}ethoxy)acetylamino]ethoxy}ethoxy)acetic acid 2,5-dioxopyrrolidin-1-yl ester (105 mg) in acetonitrile/ethanol 1:1 (10 ml). pH of the reaction mixture was kept at 10.6. After gentle stirring for 30 min, water (50 ml) was added and pH was adjusted to 5.5 with 1 N HCl to give precipitation. The product was spinned down at 3000 g for 10 min. The supernatant was discarded and the solid product was purified by preparative HPLC: C18, 3 cm column (Gemini), A-buffer 0.1% TFA in MiliQ water, B-buffer: 0.1% TFA in AcCN, flow 20 ml/min, gradient 5-80% B over 60 min.

Yield 280 mg, LC-MS, M/z: 1630.23 (M+4).

Step 2: A22K[N$^\epsilon$-{2-[2-(2-{2-[2-(12-{2-Albagen-Cys-34-ylacetylamino}dodecanoylamino)ethoxy]-ethoxy}acetylamino)ethoxy]ethoxy}acetyl] B29R, desB30 Human Insulin Albagen (vial of 200 mg custom made by New Century Pharmaceuticals, Inc. recombinant not stabilized, freeze-dried from water) was dissolved in reaction buffer (0.15 M Na$_2$HPO$_4$ pH 7.0, 2% mannitol, 3 ml). A solution of A22K [N$^\epsilon$-[2-(2-{2-[2-(2-{2-[12-({2-Iodoacetylamino}dodecanoylamino)ethoxy}-ethoxy)acetylamino]ethoxy}ethoxy)acetyl] B29R, desB30 human insulin (20 mg) in reaction buffer/acetonitrile 1:1 (2.0 ml) was added to give a solution. pH was 7.3. The mixture was stirred slowly at room temperature in dark over night. Ammonium sulphate (1 g) was added and the mixture was filtered through a Millex 0.22 μm filter. Purification was performed as described in Example 1. The product was stored in B-buffer in the freezer. The concentration was determined by absorbance measurements using the extinction coefficient: 41479. LC-MS, M/z: 1774.71 (M+31), 1732 (M+32), 1548 (M+47).

(2-{2-[2-(2-{2-[12-(2-Iodoacetylamino)dodecanoylamino]ethoxy}ethoxy)acetylamino]ethoxy}ethoxy)-acetic acid 2,5-dioxopyrrolidin-1-yl

Step 1: (2-{2-[2-(2-{2-[12-(2-Iodoacetylamino)dodecanoylamino]ethoxy}ethoxy)acetylamino]ethoxy}-ethoxy)acetic acid To a solution of [2-(2-{2-[2-(2-aminoethoxy)ethoxy]acetylamino}ethoxy)ethoxy]acetic acid (194 mg) in 0.1 M sodium carbonate was added acetonitrile (5 ml) followed by a solution of 12-(2-Iodoacetylamino)dodecanoic acid 2,5-dioxopyrrolidin-1-yl ester (260 mg) in acetonitrile (6 ml). After stirring for 45 min, pH was adjusted to 4 with 1 N HCl and the mixture was purified by preparative HPLC: C18, 3 cm column (Gemini), A-buffer 0.1% TFA in MiliQ water, B-buffer: 0.1% TFA in AcCN, flow 20 ml/min, gradient 10-80% B over 30 min. Product containing fractions were pooled and concentrated to give the title compound in 49% yield (180 m). LC-MS, M/z: 674.3 (M+1).

Step 2: (2-{2-[2-(2-{2-[12-(2-Iodoacetylamino)dodecanoylamino]ethoxy}ethoxy)acetylamino]ethoxy}-ethoxy)acetic acid 2,5-dioxopyrrolidin-1-yl To a solution of (2-{2-[2-(2-{2-[12-(2-Iodoacetylamino)dodecanoylamino]ethoxy}ethoxy)acetylamino]-ethoxy}ethoxy)acetic acid (50 mg) in ethanol (1.5 ml) was added TSTU (24 mg) and DIPEA (0.020 ml). After stirring at room temperature over night, the mixture was used directly for acylation of insulin derivatives, without work-up and purification.

Example 4

A18L, A22K[Nε-{2-[2-(2-{2-[2-(12-{2-Albagen-Cys-34-yl-acetylamino}dodecanoylamino)ethoxy]ethoxy}-acetylamino)ethoxy]ethoxy}acetyl] B29R, desB30 Human Insulin

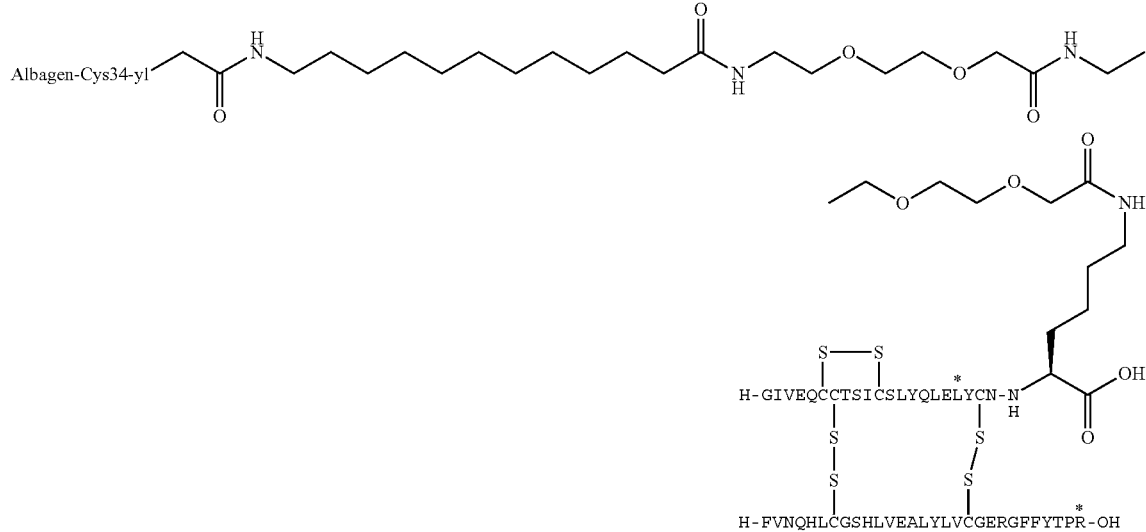

Step 1: A18L, A22K[Nε-{2-[2-(2-{2-[2-(12-(2-Iodoacetylamino}dodecanoylamino)ethoxy]ethoxy}acetylamino)ethoxy]ethoxy}acetyl] B29R, desB30 Human Insulin To a solution of A18L, A22K, B29R, desB30 human insulin (0.300 g) in 0.1 M Sodium carbonate (4 ml) and ethanol (3 ml) at pH 10.7, was added a solution of (2-{2-[2-(2-{2-[12-(2-iodoacetylamino)-dodecanoylamino]ethoxy}ethoxy)acetylamino]ethoxy}ethoxy)acetic acid 2,5-dioxopyrrolidin-1-yl ester (55 mg) in ethanol (1.5 ml). pH of the reaction mixture was kept at 10.7. After gentle stirring for 60 min, water (40 ml) was added and pH was adjusted to 5.5 with 1 N HCl to give precipitation. The product was spinned down at 3000 g for 10 min. The supernatant was discarded and the solid product was purified by preparative HPLC: C18, 3 cm column (Gemini), A-buffer 0.1% TFA in MiliQ water, B-buffer: 0.1% TFA in AcCN, flow 20 ml/min, gradient 10-70% B over 45 min.

Yield 72 mg, LC-MS, M/z: 1304.6 (M+5).

Step 2: A18L, A22K[Nε-{2-[2-(2-{2-[2-(12-{2-Albagen-Cys-34-yl-acetylamino}dodecanoylamino)-ethoxy]ethoxy}acetylamino)ethoxy]ethoxy}acetyl] B29R, desB30 Human Insulin Albagen (vial of 200 mg custom made by New Century Pharmaceuticals, Inc. recombinant not stabilized, freeze-dried from water) was dissolved in reaction buffer (0.15 M Na₂HPO₄ pH 7.0, 2% mannitol, 3 ml). A solution of A18L, A22K[Nε-[2-(2-{2-[2-(2-{2-[12-({2-Iodoacetylamino}dodecanoylamino)-ethoxy}ethoxy)acetylamino]ethoxy}ethoxy)acetyl] B29R, desB30 human insulin (18.3 mg) in reaction buffer/acetonitrile 1:1 (2.0 ml) was added to give a solution. pH was raised to 7.4 with 1 N NaOH. The mixture was stirred slowly at room temperature in dark over night. Ammonium sulphate (1 g) was added and the mixture was filtered through a Millex 0.22 µm filter. Purification was performed as described in Example 1. The product was stored in B-buffer in the freezer. The concentration was determined by absorbance measurements using the extinction coefficient: 41479. LC-MS, M/z: 72716.18

The albumin-insulin conjugate of the invention in following examples may be prepared similarly

Example 5

A18L, A22K[Nε-12-{2-(Albagen-Cys34-yl)acetylamino}dodecanoyl] B29R, desB30 Human Insulin

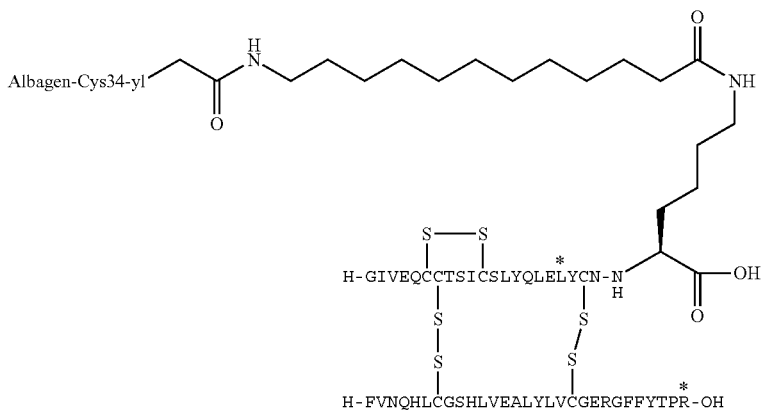

Example 6
A5L, A22K[N$^\epsilon$-12-{2-(Albagen-Cys34-yl)acetylamino}dodecanoyl] B29R, desB30 Human Insulin
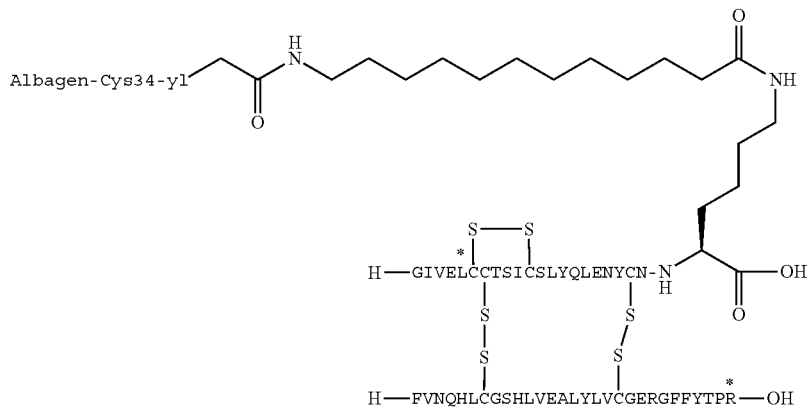
Example 7
A18L, A22K[N$^\epsilon$-12-{2-(Human serum albumin-Cys34-yl)acetylamino}dodecanoyl] B29R, desB30 Human Insulin
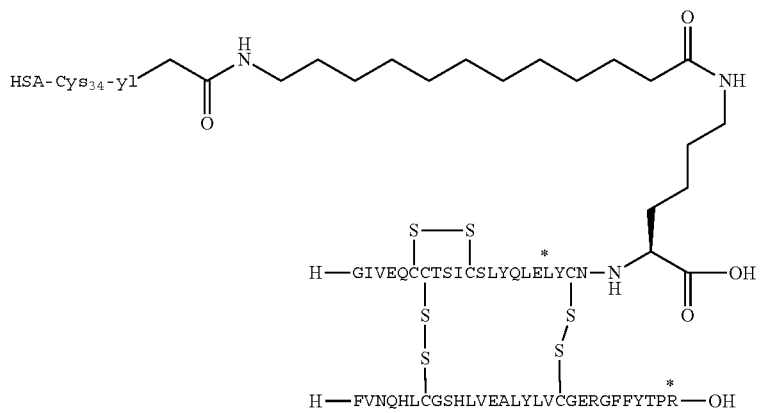
Example 8
A22K[N$^\epsilon$-12-{2-(Human serum albumin-Cys34-yl)acetylamino}dodecanoyl] B29R, desB30 Human Insulin
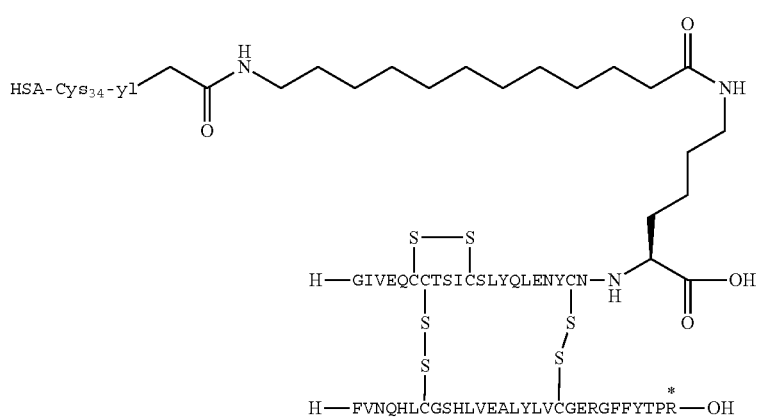

Example 9
A5L, A22K[Nε-12-{2-(Human serum albumin-Cys34-ylacetylamino)}dodecanoyl] B29R, desB30 Human Insulin
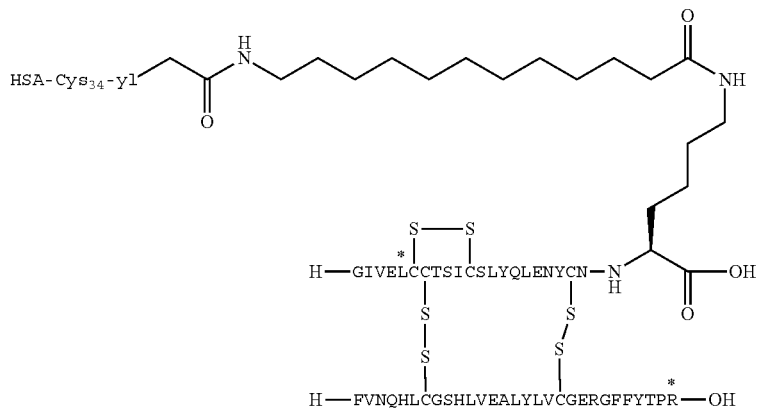
Example 10
A18L, A22K[Nε8-{3-(Albagen-Cys34-yl-2,5-dioxopyrrolidin-1-yl)propionylamino}octanoyl], B29R, desB30 Human Insulin
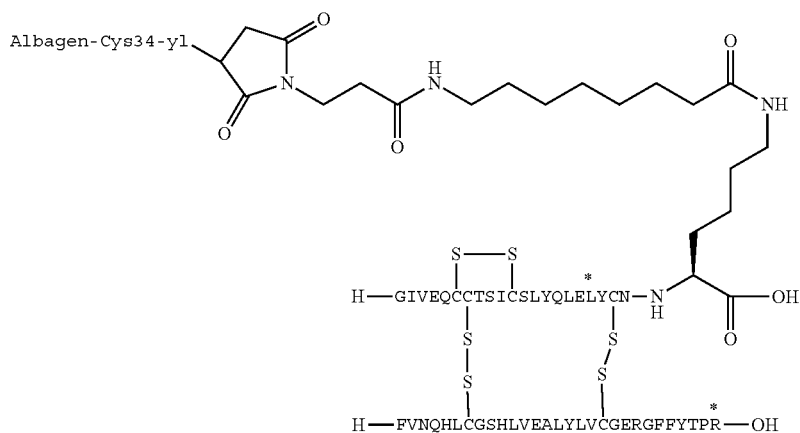
Example 11
A5L, A22K[Nε8-{3-(Albagen-Cys34-yl-2,5-dioxopyrrolidin-1-yl)propionylamino}octanoyl], B29R, desB30 Human Insulin
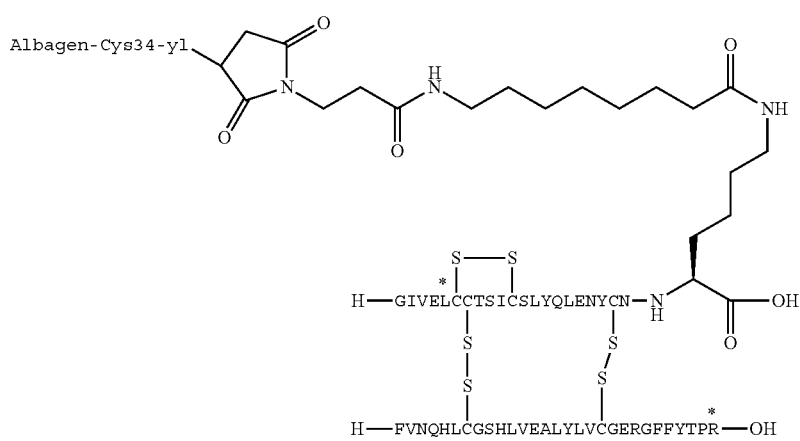

Example 12
A18L, A22K[Nᵋ8-{3-(Human serum albumin-Cys34-yl-2,5-dioxopyrrolidin-1-yl)propionylamino}octanoyl], B29R, desB30 Human Insulin
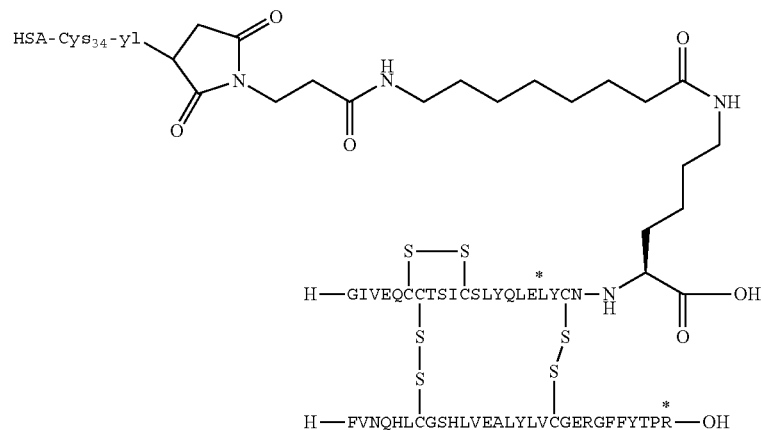
Example 13
A22K[Nᵋ8-{3-(Human serum albumin-Cys3-yl-2,5-dioxopyrrolidin-1-yl)propionylamino}octanoyl], B29R, desB30 Human Insulin
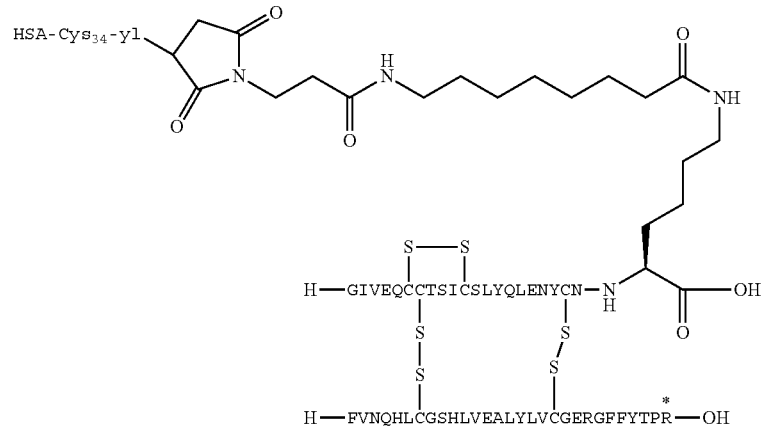
Example 14
A5L, A22K[Nᵋ8-{3-(Human serum albumin-Cys34-yl-2,5-dioxopyrrolidin-1-yl)propionylamino}octanoyl] B29R, desB30 Human Insulin
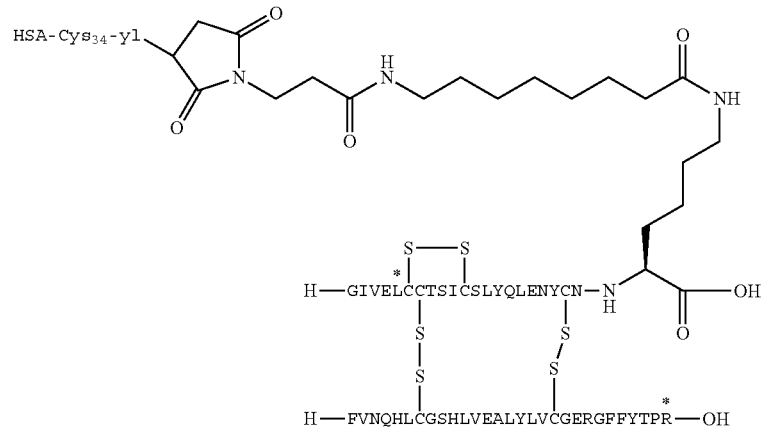

Example 15

A5L, A22K[Nᵉ-[2-(2-{2-[2-(2-{2-[12-(2-{Albagen-Cys34-yl}acetylamino)dodecanoylamino]ethoxy}-ethoxy)acetylamino]ethoxy}ethoxy)acetyl]] B29R, desB30 Human Insulin

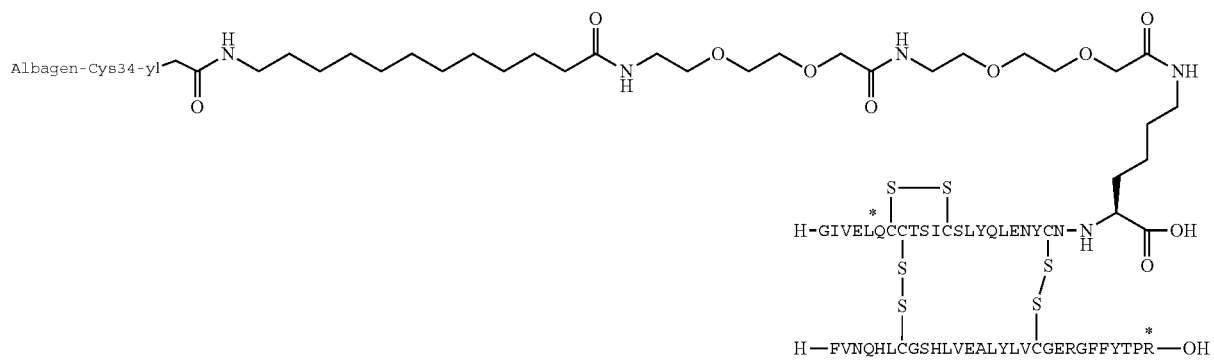

Example 16

A22K[Nᵉ-[2-(2-{2-[2-(2-{2-[12-(2-{Human serum albumin-Cys34-yl}acetylamino)dodecanoylamino]-ethoxy}ethoxy)acetylamino]ethoxy}ethoxy)acetyl]] B29R, desB30 Human Insulin

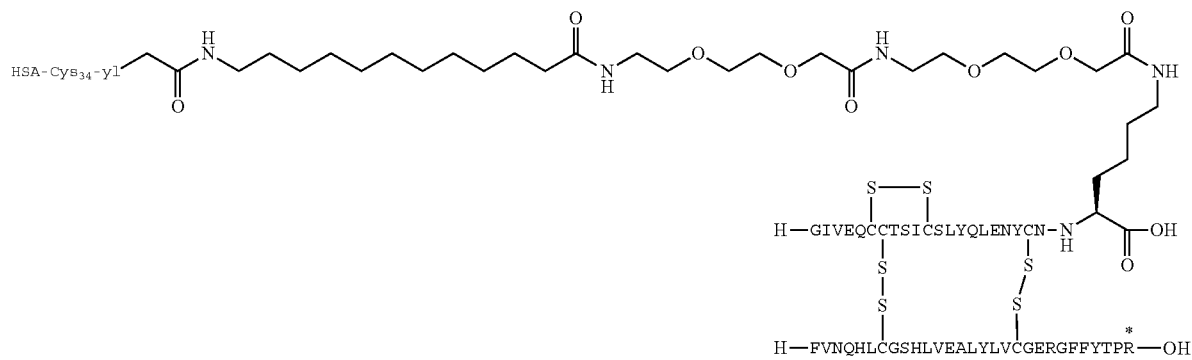

Example 17

A18L, A22K[Nᵉ-[2-(2-{2-[2-(2-{2-[12-(2-{Human serum albumin-Cys34-yl}acetylamino)dodecanoylamino]ethoxy}ethoxy)acetylamino]ethoxy}ethoxy)acetyl]] B29R, desB30 Human Insulin

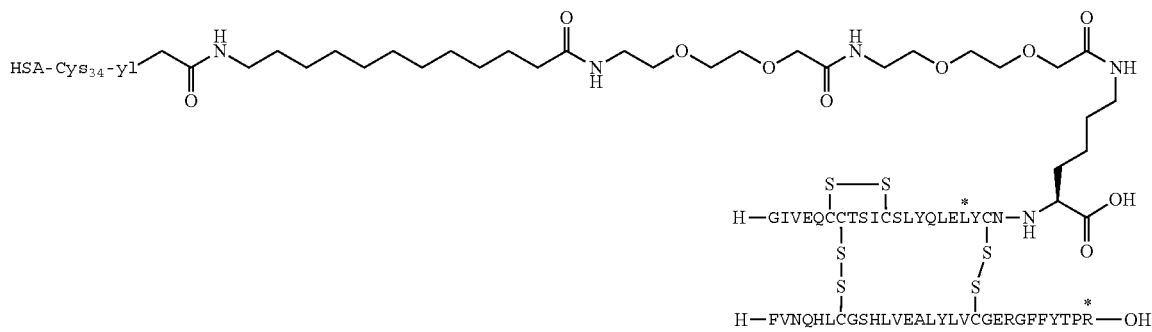

Example 18
A5L, A22K[Nε-[2-(2-{2-[2-(2-{2-[12-(2-{Human serum albumin-Cys34-yl}acetylamino)dodecanoylamino]ethoxy}ethoxy)acetylamino]ethoxy}ethoxy)acetyl]] B29R, desB30 Human Insulin
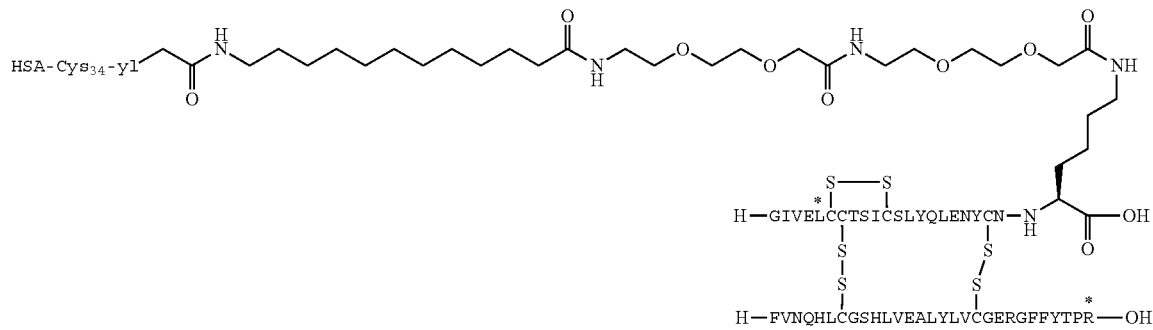
Example 19
A22K[Nε-10-{2-(Albagen-Cys34-yl)acetylamino}decanoyl] B29R, desB30 Human Insulin
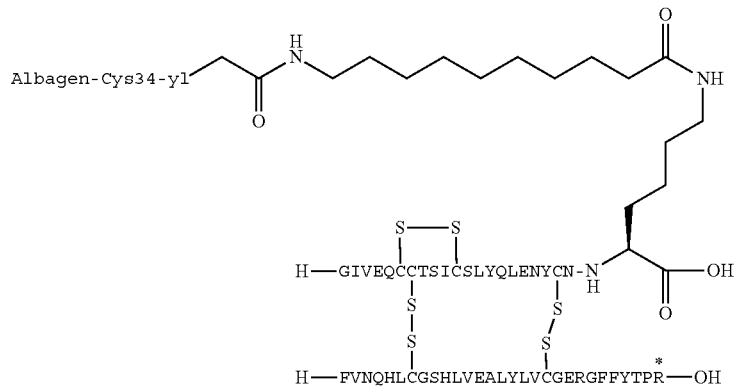
Example 20
A18L, A22K[Nε-10-{2-(Albagen-Cys34-yl)acetylamino}decanoyl] B29R, desB30 Human Insulin
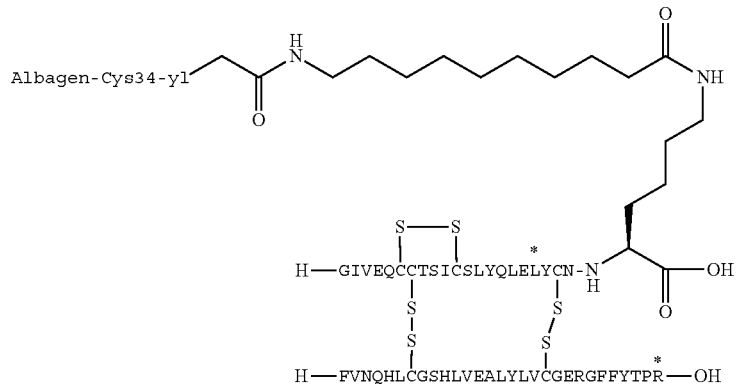

Example 21

A22K[Nε-10-{2-(Human serum albumin-Cys34-yl)acetylamino}decanoyl] B29R, desB30 Human Insulin

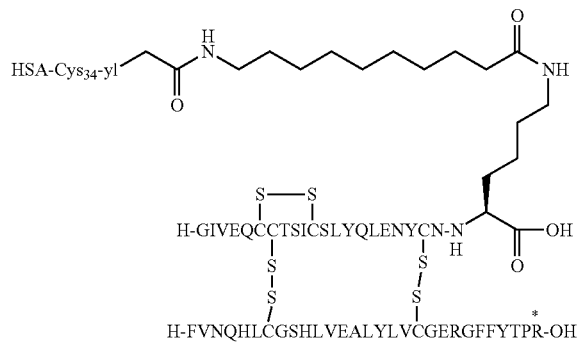

Example 22

A18L, A22K[Nε-10-{2-(Human serum albumin-Cys34-yl)acetylamino}decanoyl] B29R, desB30 Human Insulin

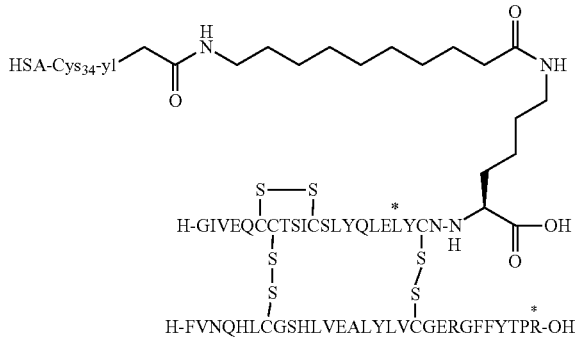

Example 23

A22K[Nε-10-{3-(Albagen-Cys34-yl-2,5-dioxopyrrolidin-1-yl)propionylamino}decanoyl], B29R, desB30 Human Insulin

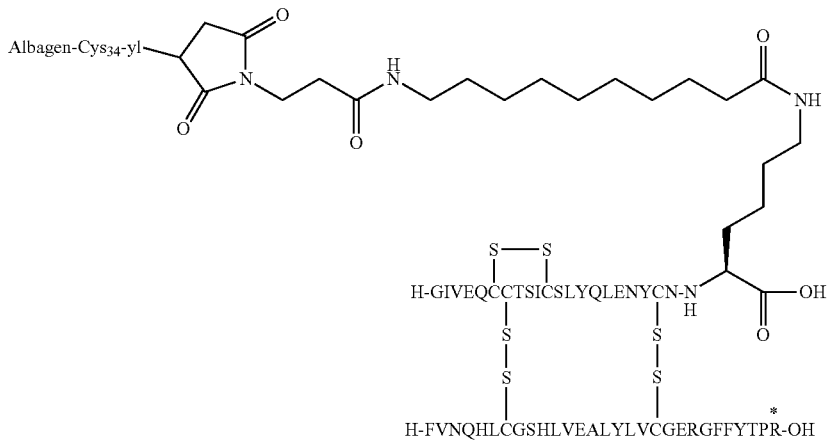

Example 24

A18L, A22K[Nε-10-{3-(Albagen-Cys34-yl-2,5-dioxopyrrolidin-1-yl)propionylamino}decanoyl], B29R, desB30 Human Insulin

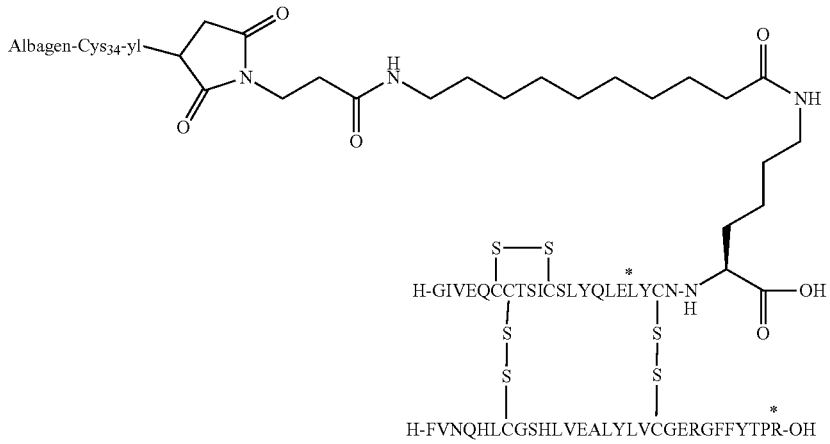

Example 25
A22K[N$^\epsilon$-10-{3-(Human serum albumin-Cys34-yl-2,5-dioxopyrrolidin-1-yl)propionylamino}decanoyl], B29R, desB30 Human Insulin
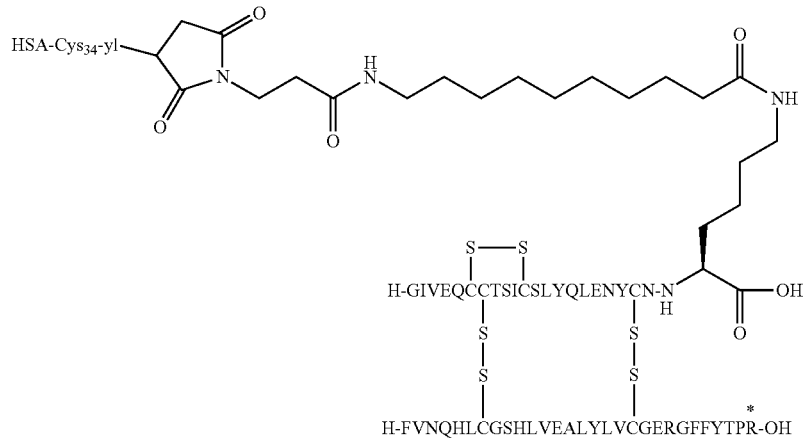
Example 26
A18L, A22K[N$^\epsilon$-10-{3-(Human serum albumin-Cys34-yl-2,5-dioxopyrrolidin-1-yl)propionylamino}-decanoyl], B29R, desB30 Human Insulin
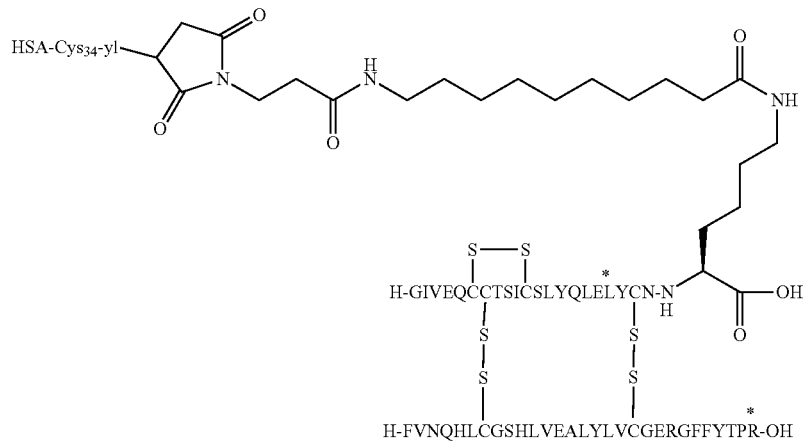
Example 27
A22K[N$^\epsilon$-16-{2-(Albagen-Cys34-yl)acetylamino}hexadecanoyl] B29R, desB30 Human Insulin
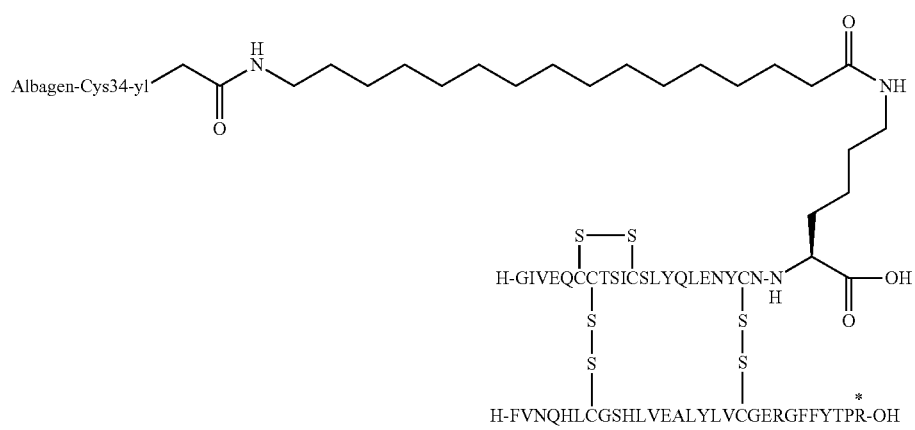

Example 28
A18L, A22K[N$^\varepsilon$-16-{2-(Albagen-Cys34-yl)acetylamino}hexadecanoyl] B29R, desB30 Human Insulin
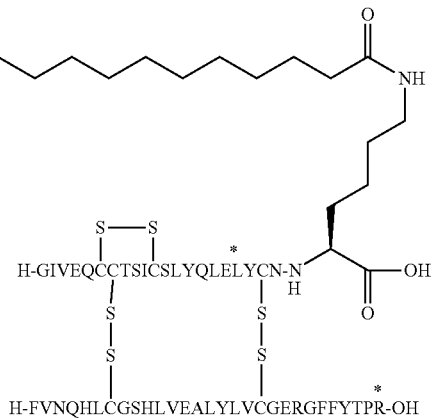
Example 29
A22K[N$^\varepsilon$-16-{2-(Human serum albumin-Cys34-yl)acetylamino}hexadecanoyl] B29R, desB30 Human Insulin
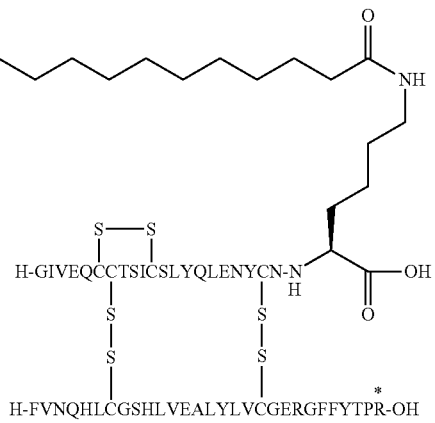
Example 30
A18L, A22K[N$^\varepsilon$-16-{2-(Human serum albumin-Cys34-yl)acetylamino}hexadecanoyl] B29R, desB30 Human Insulin
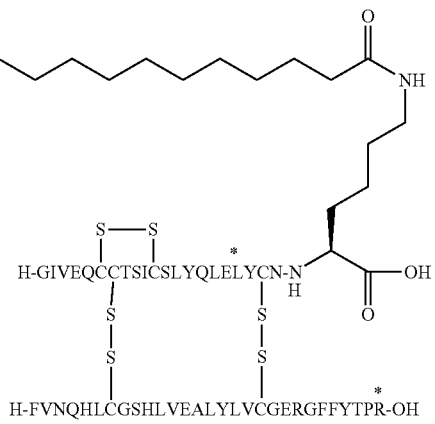

Example 31
A22K[Nε-16-{3-(Albagen-Cys34-yl-2,5-dioxopyrrolidin-1-yl)propionylamino}hexadecanoyl], B29R, desB30 Human Insulin
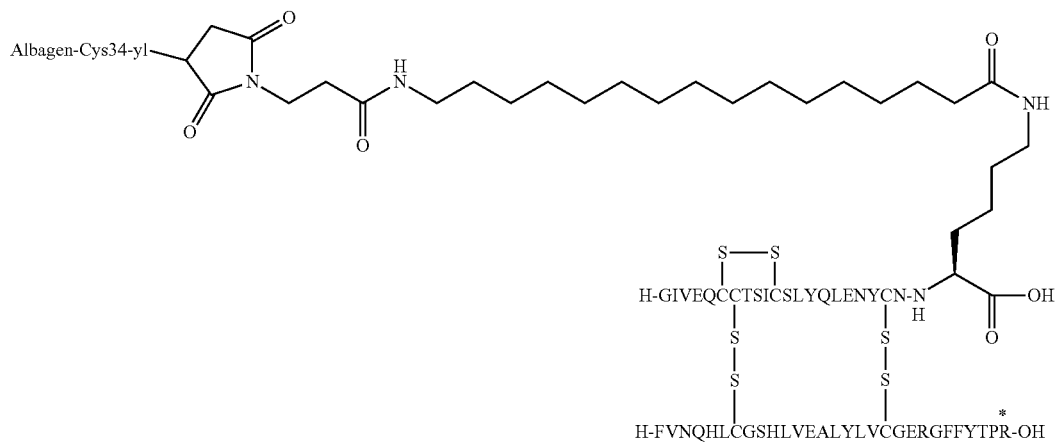
Example 32
A18L, A22K[Nε-16-{3-(Albagen-Cys34-yl-2,5-dioxopyrrolidin-1-yl)propionylamino}hexadecanoyl], B29R, desB30 Human Insulin
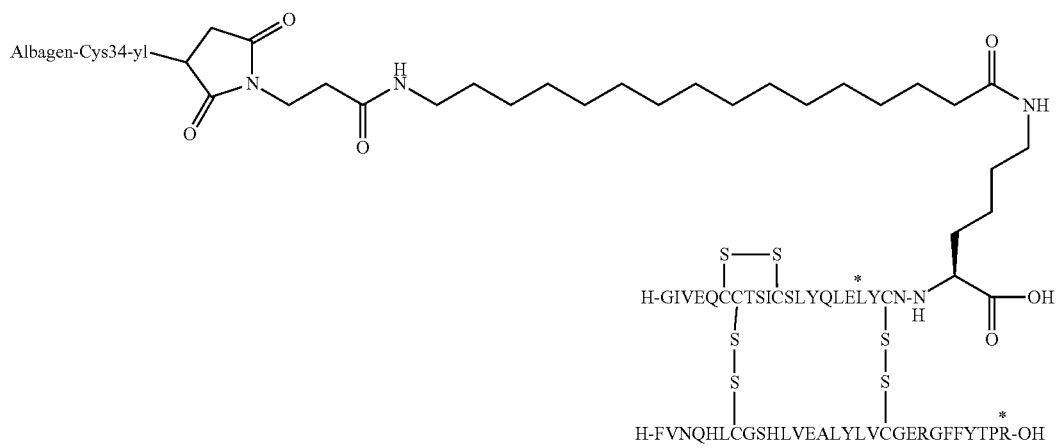

Example 33
A22K[Nε-16-{3-(Human serum albumin-Cys34-yl-2,5-dioxopyrrolidin-1-yl)propionylamino}hexadecanoyl], B29R, desB30 Human Insulin
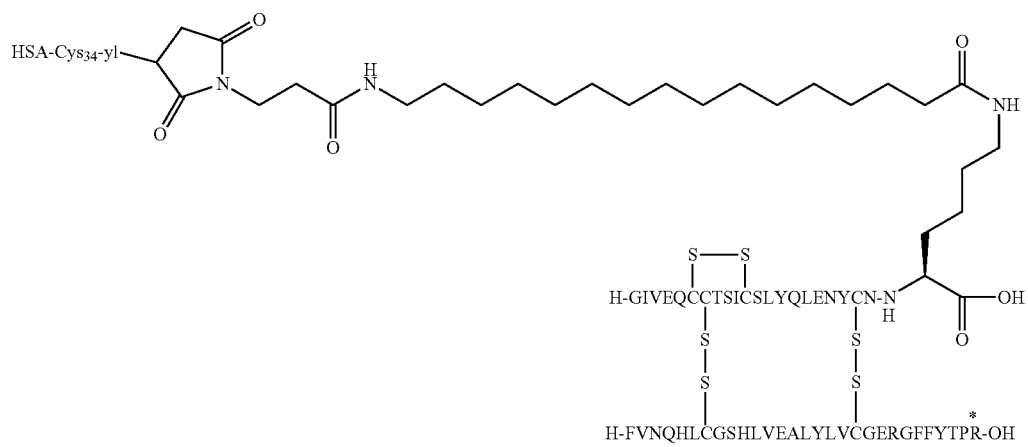
Example 34
A18L, A22K[Nε-16-{3-(Human serum albumin-Cys34-yl-2,5-dioxopyrrolidin-1-yl)propionylamino}hexadecanoyl], B29R, desB30 Human Insulin
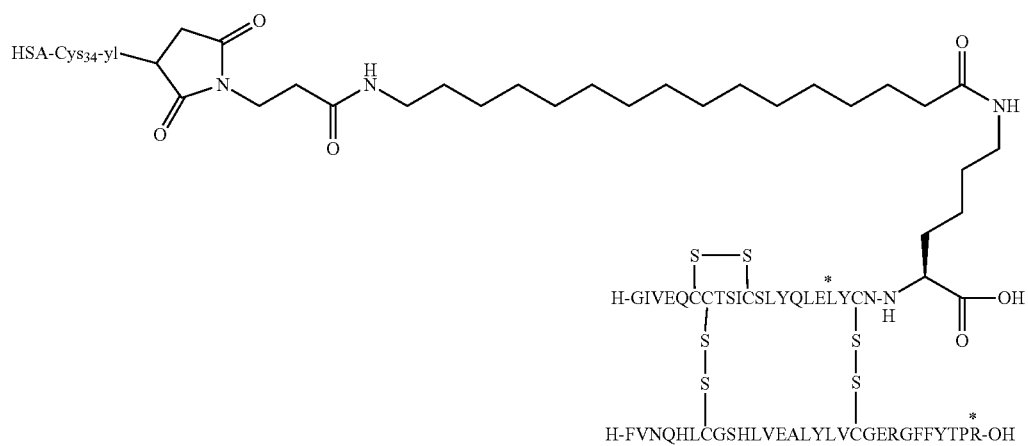

Example 35
A22K[Nε-[2-(2-{2-[2-(2-{2-M 0-(2-{Albagen-Cys34-yl}acetylamino)decanoylamino]ethoxy}ethoxy)acetylamino]ethoxy}ethoxy)acetyl]] B29R, desB30 Human Insulin
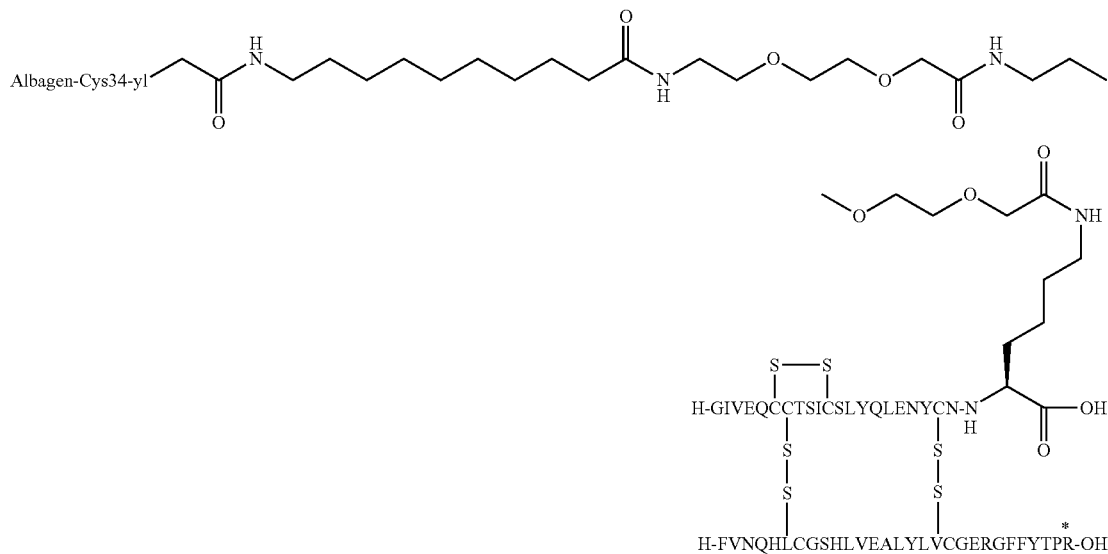
Example 36
A18L, A22K[Nε-[2-(2-{2-[2-(2-{2-M 0-(2-{Albagen-Cys34-yl}acetylamino)decanoylamino)]ethoxy}-ethoxy)acetylamino]ethoxy}ethoxy)acetyl]] B29R, desB30 Human Insulin
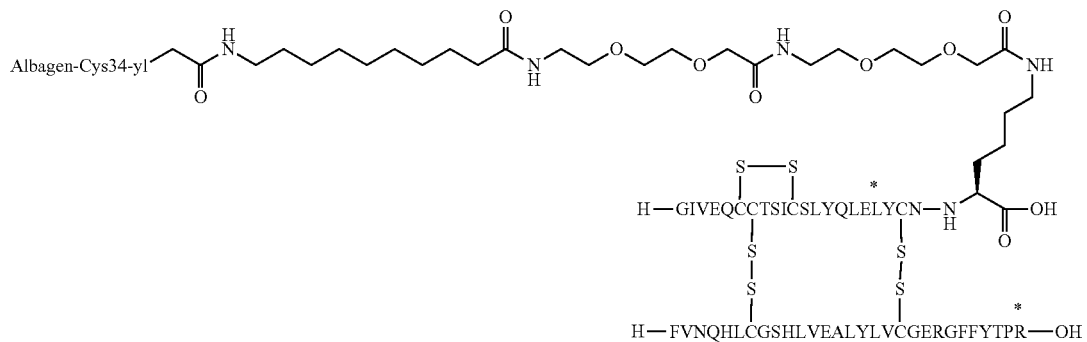

Example 37

A22K[Nε-[2-(2-{2-[2-(2-{2-[10-(2-{Human serum albumin-Cys34-yl}acetylamino)decanoylamino]-ethoxy}ethoxy)acetylamino]ethoxy}ethoxy)acetyl]] B29R, desB30 Human Insulin

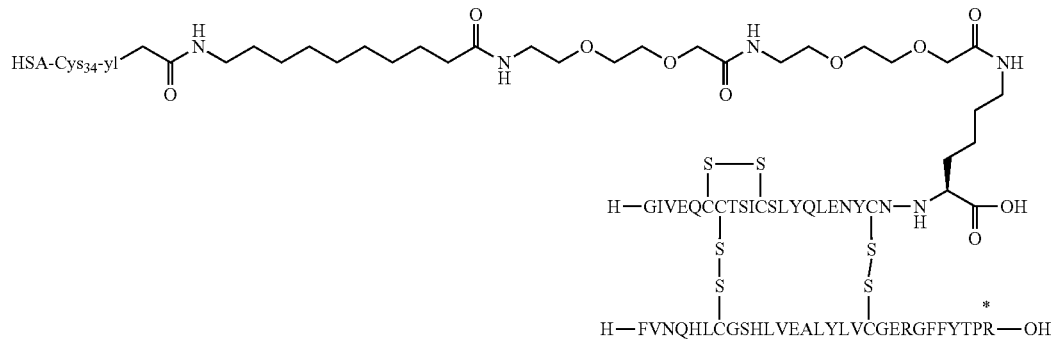

Example 38

A18L, A22K[Nε-[2-(2-{2-[2-(2-{2-[10-(2-{Human serum albumin-Cys34-yl}acetylamino)decanoylamino]-ethoxy}ethoxy)acetylamino]ethoxy}ethoxy)acetyl]] B29R, desB30 Human Insulin

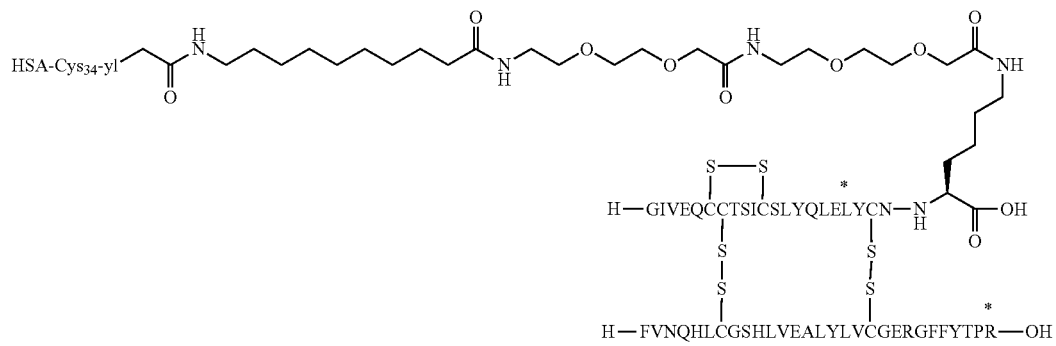

Example 39

A22K[Nε-[2-(2-{2-[2-(2-{2-[16-(2-{Albagen-Cys34-yl}acetylamino)hexadecanoylamino)]ethoxy}ethoxy)-acetylamino]ethoxy}ethoxy)acetyl]] B29R, desB30 Human Insulin

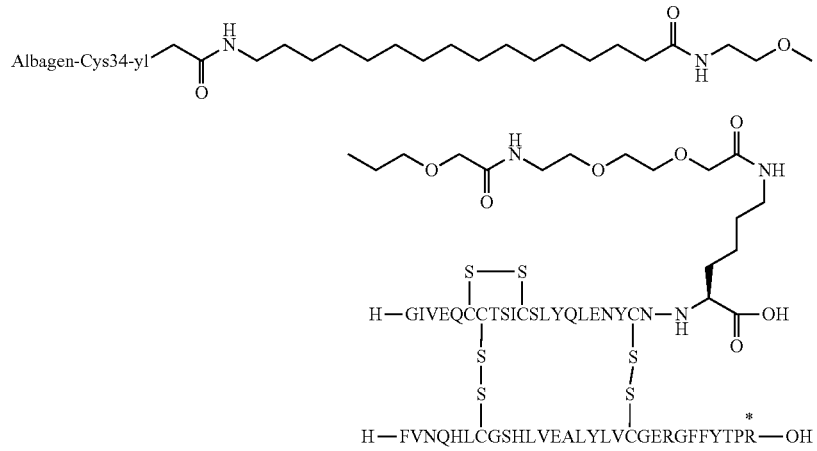

Example 40

A18L, A22K[Nᵉ-[2-(2-{2-[2-(2-{2-[16-(2-{Albagen-Cys34-yl}acetylamino)hexadecanoylamino)]ethoxy}-ethoxy)acetylamino]ethoxy}ethoxy)acetyl]] B29R, desB30 Human Insulin

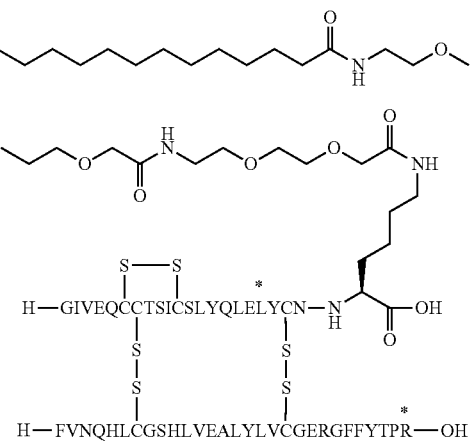

Example 41

A22K[Nᵉ-[2-(2-{2-[2-(2-{2-[16-(2-{Human serum albumin-Cys34-yl}acetylamino)hexadecanoylamino]-ethoxy}ethoxy)acetylamino]ethoxy}ethoxy)acetyl]] B29R, desB30 Human Insulin

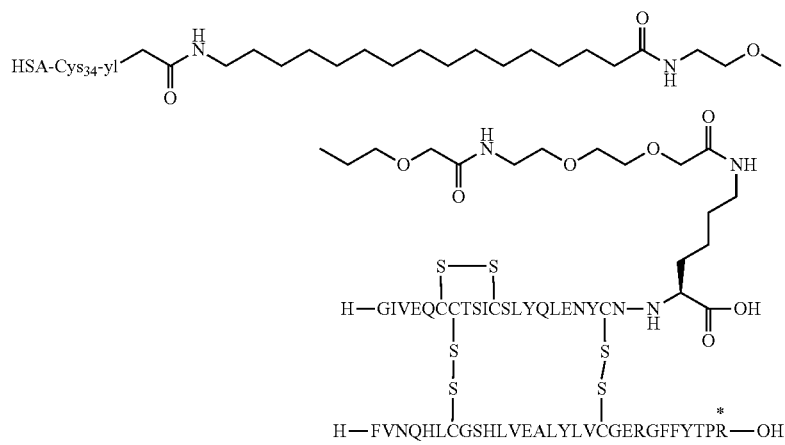

Example 42

A18L, A22K[Nᵉ-[2-(2-{2-[2-(2-{2-[16-(2-{Human serum albumin-Cys34-yl}acetylamino)hexadecanoylamino]ethoxy}ethoxy)acetylamino]ethoxy}ethoxy)acetyl] B29R, desB30 Human Insulin

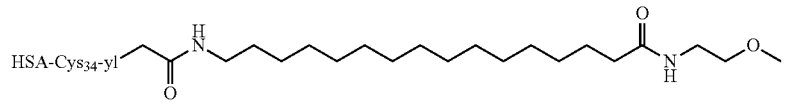

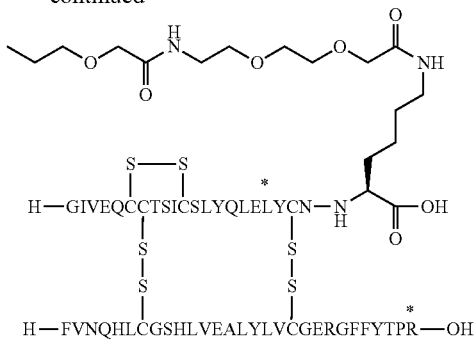
Example 43
A22K[Nε-[2-(2-{2-[2-(2-{2-[10-(3-{(Albagen-Cys34-yl)2,5-dioxopyrrolidin-1-yl}propionylamino)decanoylamino)]ethoxy}ethoxy)acetylamino]ethoxy}ethoxy)acetyl]] B29R, desB30 Human Insulin
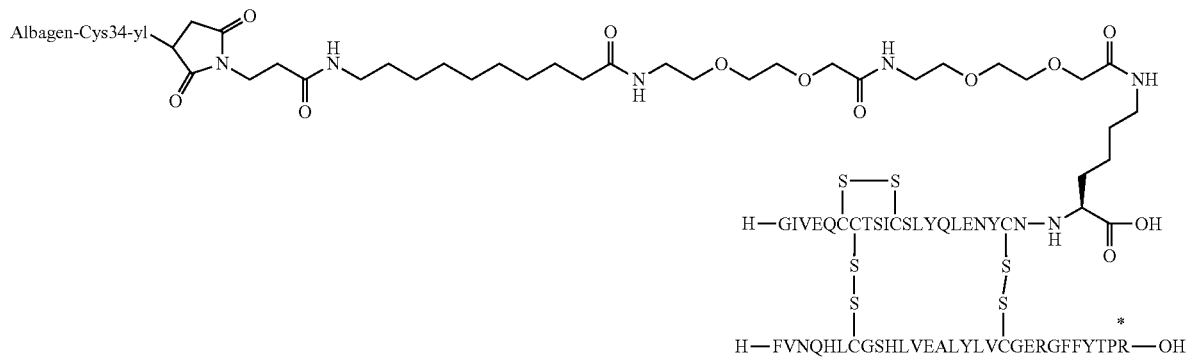
Example 44
18L, A22K[Nε-[2-(2-{2-[2-(2-{2-[10-(3-{(Albagen-Cys34-yl)2,5-dioxopyrrolidin-1-yl}propionylamino)-decanoylamino]ethoxy}ethoxy)acetylamino]ethoxy}ethoxy)acetyl]] B29R, desB30 Human Insulin
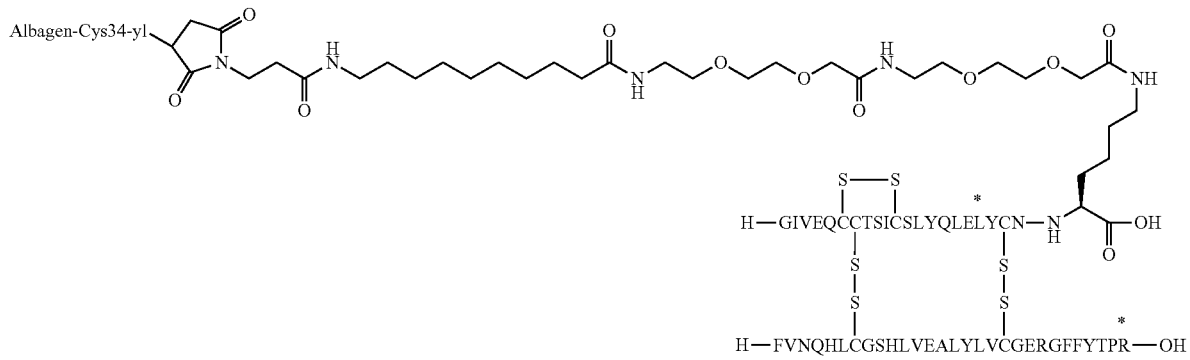

Example 45

A22K[Nε-[2-(2-{2-[2-(2-{2-[10-(3-{(Human serum albumin-Cys34-yl)2,5-dioxopyrrolidin-1-yl}propionylamino)decanoylamino]ethoxy}ethoxy)acetylamino]ethoxy}ethoxy)acetyl]] B29R, desB30 Human Insulin

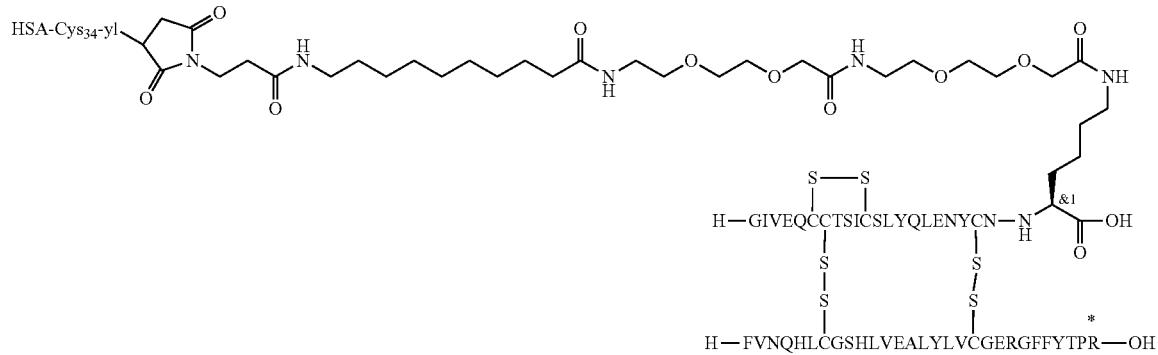

Example 46

18L, A22K[Nε-[2-(2-{2-[2-(2-{2-[10-(3-{(Human serum albumin-Cys35-yl)2,5-dioxopyrrolidin-1-yl}-propionylamino)decanoylamino]ethoxy}ethoxy)acetylamino]ethoxy}ethoxy)acetyl]] B29R, desB30 Human Insulin

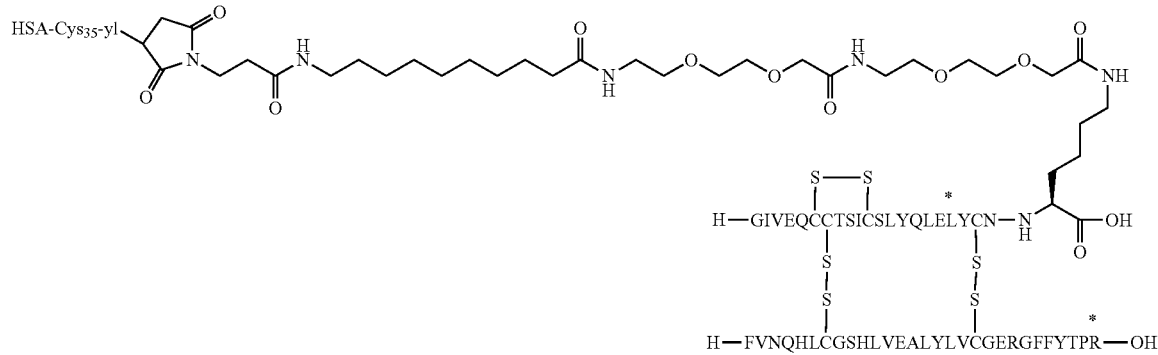

Example 47

A22K[Nε-[2-(2-{2-[2-(2-{2-[16-(3-{(Albagen-Cys34-yl)2,5-dioxopyrrolidin-1-yl}propionylamino})hexadecanoylamino]ethoxy}ethoxy)acetylamino]ethoxy}ethoxy)acetyl]] B29R, desB30 Human Insulin

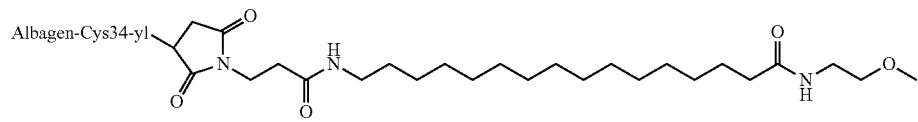

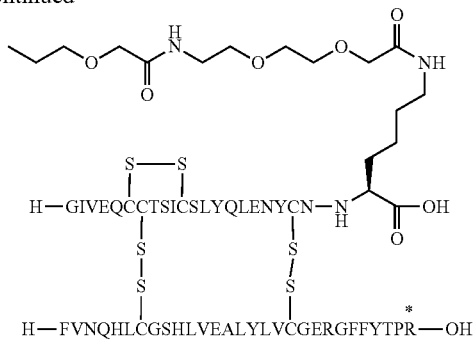
Example 48
18L, A22K[N$^\epsilon$-[2-(2-{2-[2-(2-{2-[16-(3-{(Albagen-Cys34-yl)2,5-dioxopyrrolidin-1-yl)propionylamino}-hexadecanoylamino)ethoxy}ethoxy)acetylamino]ethoxy}ethoxy)acetyl] B29R, desB30 Human Insulin
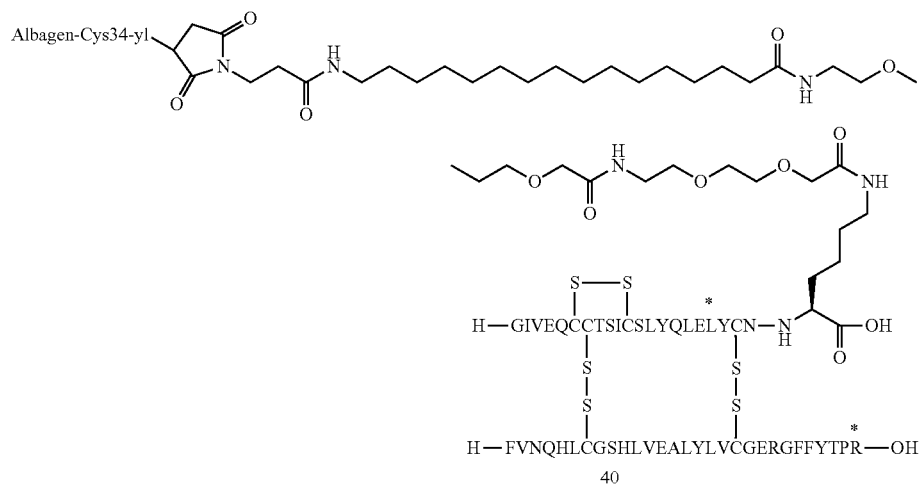
Example 49
A22K[N$^\epsilon$-[2-(2-{2-[2-(2-{2-[16-(3-{(Human serum albumin-Cys34-yl-2,5-dioxopyrrolidin-1-yl}propionylamino)hexadecanoylamino]ethoxy}ethoxy)acetylamino]ethoxy}ethoxy)acetyl]] B29R, desB30 human Insulin
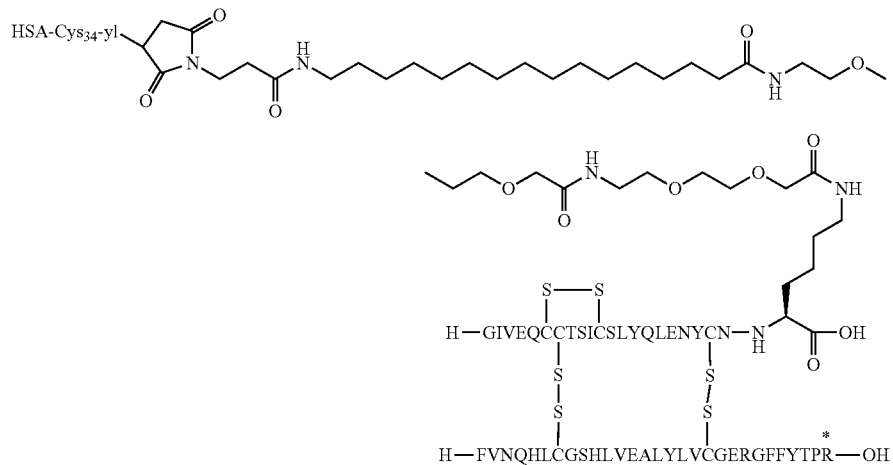

Example 50

18L, A22K[N$^\epsilon$-[2-(2-{2-[2-(2-{2-[16-(3-{(Human serum albumin-Cys34)yl-2,5-dioxopyrrolidin-1-yl}-propionylamino]hexadecanoylamino)ethoxy}ethoxy) acetylamino]ethoxy}ethoxy)acetyl]] B29R, desB30 Human Insulin

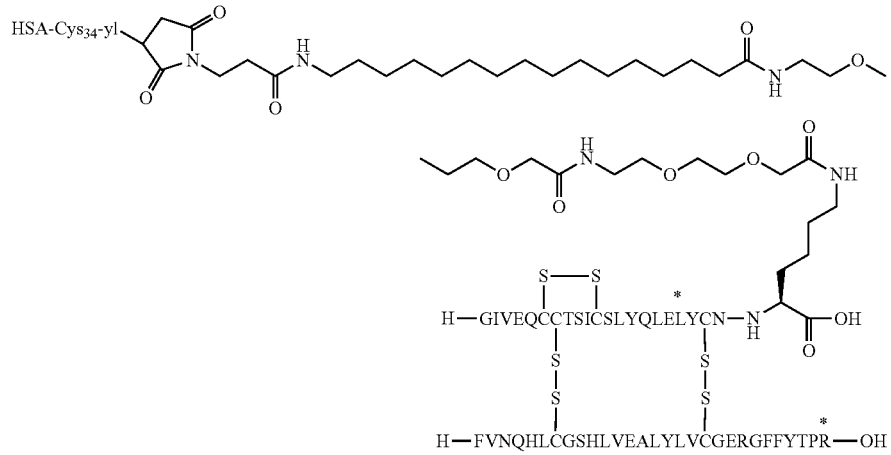

Example 51

S.c Administration of the Insulin Albagen Conjugate of Example 1 to ZDF Rats 16 male 16 weeks old feed ZDF rats (approx. 400 g) were divided into 2 groups. Food was removed when the experiment was started. One group was dosed with vehicle, the other group was dosed with the insulin conjugate of example 1, 87.3 nmol/kg at the time t=0. Blood samples were taken from the tail vein at t=30-, 60-, 90-, 120-, 180- and 240 minutes and at t=5-, 6-, 7-, 8-, 9- and 10 hours.

Example 52

Insulin-stimulated Intracellular Signaling in Insulin Sensitive Tissues in Normal Mice 21 male nonfasted NMRI mice (30-40 g) were divided into 7 groups: a basal group, 3 groups for human insulin (HI) treatment and 3 groups for treatment with the insulin albumin conjugate of example 1. Food was removed when the experiment was started. A blood sample for glucose measurement was taken from all mice before dosing. The basal group (untreated) was then sacrificed (by cervical dislocation) and tissues were removed to determine basal values. The other mice were dosed intravenously with HI (6 nmol/kg) or the insulin HSA conjugate of example 1 (9.9 nmol/kg). Similar blood glucose lowering was achieved in both groups. After each of the time points 5, 15 and 120 minutes, a tail tip blood sample was taken from one HI treated group and one Example 1 treated group, whereafter these animals were sacrificed and tissues removed. Insulin receptor phosphorylation molecules were measured in liver, lower leg muscles and epididymal fat by BioSource ELISA.

Example 53

Insulin Receptor Binding of the Insulin Albumin Conjugates of this Invention

The affinity of the insulin albumin conjugates of this invention for the human insulin receptor is determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 µl of a 1:5000 diluted purified recombinant human insulin receptor (either with or without exon 11), an amount of a stock solution of A14Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl reagent mix is then added to each well in the Packard Optiplate and a dilution series of the insulin derivative is made in the Optiplate from appropriate samples. The samples are then incubated for 16 hours while gently shaken. The phases are the then separated by centrifugation for 1 min and the plates counted in a Topcounter. The binding data were fitted using the nonlinear regression algorithm in the GraphPad Prism 2.01 (GraphPad Software, San Diego, Calif.).

Insulin receptor affinities of two known insulins and four selected insulins of the invention:

| Example No. | IR-A affinity (0% HSA) | Parent insulin (all desB30 human insulins) |
|---|---|---|
|  | 100% | desB30 human insulin (not conjugated) |
|  | 102% | A22K, B29R (not conjugated) |
| 1 | 13.0% | A22K, B29R |
| 2 | 13.6% | A22K, B29R |
| 3 | 20.0% | A22K, B29R |
| 4 | 44.1% | A18L, A22K, B29R |

Sequence Lists

In the examples, the following A chains with the following deviations from human insulin are given as ID SEQ Nos. 1-3, respectively: A5L, A22K; A18L, A22K; and A22K, and the following B chain with the following deviations from human insulin is given as ID SEQ No. 4: B29R, desB30.

What is claimed is:

1. A compound of $$M\text{-}Z_n\text{—}Y_o\text{-Ins} \quad \text{formula II:}$$

$$\text{Alb-}M'\text{-}Z_n\text{—}Y_o\text{-Ins}; \quad \text{formula III:}$$

wherein Ins represents insulin or a human insulin analogue;
 wherein the human insulin analogue has a lysine residue at the C-terminal end of the A-chain (A22K), or at the C-terminal end of an extension of the A-chain; wherein the extension, compared to the A21 amino acid residue, consists of a single amino acid residue being lysine, or a lysine residue at the C-terminal end of an extension consisting of 2-5 amino acid residues; and
 up to six of the amino acids residues in position A1-A21 and B1-B30, as compared to human insulin, has been deleted or substituted by another amino acid residue;

M' represents the thiol reactive group designated M after reaction with a thiol group of Alb (albumin);

M represents a Michael acceptor represented by a malimido group, a vinylsulfone or the like, a thiol reactive group represented by iodide, pyridyldisulfide, methoxy- or ethoxycarbonyldisulfide and o-nitrophenyldisulphide;

wherein M and M' are bound, via the linker $Z_n$—$Y_o$, to the epsilon-amino group of the C-terminal lysine residue in the A-chain, from which epsilon-amino group a hydrogen atom has been removed;

Z is a covalent bond or is selected from —NH—CH$_2$—CH$_2$—O)$_p$—CH$_2$—CO—; —NH—(CH$_2$)$_q$—CH$_2$—CO—; —NH—(CH$_2$—CH$_2$—O)$_r$—CH$_2$—CH$_2$—CO—; —HN—CH$_2$—CH$_2$—NH—CO—; —NH—CH$_2$—CH$_2$—O—CH$_2$—CH$_2$—NH—CO—CH$_2$—CH$_2$—CO—; and —NH—C$_6$H$_4$—CO—; wherein p is 0 or an integer in the range from 1 to 24;
q is 0 or an integer in the range from 1 to 24;
r is 0 or an integer in the range from 1 to 24; and
—C$_6$H$_4$— is para-phenylene;

Y is a covalent bond or is selected from —NH—CH$_2$—CH$_2$—O)$_p$—CH$_2$—CO—; —NH—(CH$_2$)$_q$—CH$_2$—CO—; —NH—(CH$_2$—CH$_2$—O)$_r$—CH$_2$—CH$_2$—CO—; —HN—CH$_2$—CH$_2$—NH—CO—; —NH—CH$_2$—CH$_2$—O—CH$_2$—CH$_2$—NH—CO—CH$_2$—CH$_2$—CO—; and —NH—C$_6$H$_4$—CO—; wherein p is 0 or an integer in the range from 1 to 24;
q is 0 or an integer in the range from 1 to 24;
r is 0 or an integer in the range from 1 to 24; and
—C$_6$H$_4$— is para-phenylene;
n represents an integer in the range from 1 to 10
o is an integer in the range from 0 to 10; and
Alb is selected from the group consisting of ALBAGEN™ and human serum albumin.

2. A compound according to claim 1, wherein the compound is selected from the group consisting of A22K[N$^\epsilon$8-{3-(ALBAGEN™-Cys34-yl-2,5-dioxopyrrolidin-1-yl)propionylamino}octanoyl],B29R, desB30 human insulin;

A22K [N$^\epsilon$-12-{2-(ALBAGEN™-Cys-34-ylacetylamino)}dodecanoyl]B29R, desB30 human insulin;

A22K[N$^\epsilon$-{2-[2-(2-{2-[2-(12-{2-ALBAGEN™-Cys-34-ylacetylamino}dodecanoylamino)ethoxy]ethoxy}acetylamino)ethoxy]ethoxy}acetyl] B29R, desB30human insulin;

A18L, A22K[N$^{\epsilon-}${2-[2-(2-{2-[2-(12{2 -ALBAGEN™-Cys-34-yl-acetylamino}-dodecanoylamino)ethoxy]ethoxy}acetylamino)ethoxyl]ethoxy}acetyl] B29R, desB30 human insulin;

A18L, A22K[N$^\epsilon$-12-{2-(ALBAGEN™-Cys34-yl)acetylamino}dodecanoyl] B29R, desB30 human insulin;

A5L, A22K[N$^\epsilon$-12-{2-(ALBAGEN™-Cys34-yl)acetylamino}dodecanoyl] B29R, desB30 human insulin;

A18L,A22K[N$^\epsilon$-12-{2-(human serum albumin-Cys34-yl)acetylamino}dodecanoyl] B29R, desB30 human insulin;

A22K[N$^\epsilon$-12-{2-(human serum albumin-Cys34-yl)acetylamino}dodecanoyl] B29R, desB30 human insulin;

A5L, A22K[N$^\epsilon$-12-{2-(human serum albumin-Cys34-ylacetylamino)}dodecanoyl] B29R, desB30 human insulin;

A18L, A22K[N$^\epsilon$8-{3-(ALBAGEN™-Cys34-yl-2,5-dioxopyrrolidin-1-yl)propionylamino}octanoyl], B29R, desB30 human insulin;

A5L, A22K[N$^\epsilon$8-{3-(ALBAGEN™-Cys34-yl-2,5-dioxopyrrolidin-1-yl)propionylamino}octanoyl], B29R, desB30 human insulin;

A18L, A22K[N$^\epsilon$8-{3-(human serum albumin-Cys34-yl-2,5-dioxopyrrolidin-1-yl)-propionylamino}octanoyl], B29R, desB30 human insulin;

A22K[N$^\epsilon$8-{3-(human serum albumin-Cys34-yl-2,5-dioxopyrrolidin-1-yl)propionylamino}octanoyl], B29R, desB30human insulin;

A5L, A22K[N$^\epsilon$8-{3-(human serum albumin-Cys34-yl-2,5-dioxopyrrolidin-1-yl)propionylamino}octanoyl], B29R, desB30 human insulin;

A5L, A22K N$^\epsilon$-[2-(2-{2-[2-(2-{2-[12-(2-{ALBAGEN™-Cys34-yl}acetylamino)-dodecanoylamino]ethoxy}ethoxy)acetylamino]ethoxy}ethoxy)acetyl]] B29R, desB30 human insulin;

A22K [N$^\epsilon$-[2-(2-{2-[2-(2-{2-[12-(2-{human serum albumin-Cys34-yl}acetylamino)dodecanoylamino]ethoxy}ethoxy)acetylamino]ethoxy}ethoxy)acetyl]] B29R, desB30 human insulin;

A18L, A22K[N$^\epsilon$-[2-(2-{2-[2-(2-{2-[12-(2{human serum albumin-Cys34-yl}acetylamino)dodecanoylamino]ethoxy}ethoxy)acetylamino]ethoxy}ethoxy)acethyl]] B29R, desB30 human insulin;

A5L, A22K[N$^\epsilon$-[2-(2-{2-[2-(2-{2-[12-(2-{human serum albumin-Cys34-yl}acetylamino)dodecanoylamino]ethoxy}ethoxy)acetylamino]ethoxy}ethoxy)acethyl]] B29R, desB30 human insulin;

A22K[N$^\epsilon$-10-{2-(ALBAGEN™-Cys34-yl)acetylamino}dodecanoyl] B29R, desB30 human insulin;

A18L, A22K[N$^\epsilon$-10-{2-(ALBAGEN™-Cys34-yl)acetylamino}dodecanoyl] B29R, desB30 human insulin; A22K[N$^\epsilon$-10-{2-(human serum albumin-Cys34-yl)acetylamino}dodecanoyl] B29R, desB30 human insulin;

A18L,A22K[N$^\epsilon$-10-{2-(human serum albumin-Cys34-yl)acetylamino}dodecanoyl] B29R, desB30 human insulin;

A22K [N$^\epsilon$-10-{3-(ALBAGEN™-Cys34-yl-2,5-dioxopyrrolidin-1-yl)-propionylamino}decanoyl], B29R, desB30 human insulin;

A18L, A22K[N$^\epsilon$-10-{3-(ALBAGEN™-Cys34-yl-2,5-dioxopyrrolidin-1-yl)-propionylamino}decanoyl], B29R, desB30 human insulin;

A22K[N$^{\epsilon-}$10-{3-(human serum albumin-Cys34-yl-2,5-dioxopyrrolidin-1-yl)-propionylamino}decanoyl], B29R, desB30 human insulin;

A18L,A22K[N$^\epsilon$-10-{3-(human serum albumin-Cys34-yl-2,5-dioxopyrrolidin-1-yl)-propionylamino}decanoyl], B29R, desB30 human insulin;

A22K[N$^\epsilon$-16-{2-(ALBAGEN™-Cys34-yl)acetylamino}hexadecanoyl] B29R, desB30 human insulin;

A18L, A22K[N$^\epsilon$-16-{2-(ALBAGEN™-Cys34-yl)acetylamino}hexadecanoyl] B29R, desB30 human insulin;

A22K[N$^\epsilon$-16-{2-(human serum albumin-Cys34-yl)acetylamino}hexadecanoyl]B29R, desB30 human insulin;

A18L,A22K[N$^\epsilon$-16-{2-(human serum albumin-Cys34-yl)acetylamino}hexadecanoyl] B29R, desB30 human insulin;

A22K[N^ε-16-{3-(ALBAGEN™-Cys34-yl-2,5-dioxopyrrolidin-1-yl)propionylamino}-hexadecanoyl], B29R, desB30 human insulin;

A18L, A22K[N^ε-16-{3-(ALBAGEN™-Cys34-yl-2,5-dioxopyrrolidin-1-yl)propionylamino}hexadecanoyl], B29R, desB30 human insulin;

A22K[N^ε-16-{3-(human serum albumin-Cys34-yl-2,5-dioxopyrrolidin-1-yl)propionylamino}hexadecanoyl], B29R, desB30 human insulin;

A18L, A22K[N^ε-16-{3-(human serum albumin-Cys34-yl-2,5-dioxopyrrolidin-1-yl)propionylamino}hexadecanoyl], B29R, desB30 human insulin;

A22K[N^ε-[2-(2-{2-[2-(2-{2-[10-(2-{ALBAGEN198-Cys34-yl}acetylamino)decanoylamino]ethoxy}ethoxy)acetylamino]ethoxy}ethoxy)acetyl]] B29R, desB30 human insulin;

A18L, A22K[N^ε-[2-(2-{2-[2-(2-{2-[10-(2{ALBAGEN™-Cys34-yl}-acetylamino)decanoylamino)]ethoxy}ethoxy)acetylamino]ethoxy}ethoxy)acetyl]] B29R, desB30 human insulin;

A22K[N^ε-[2-(2-{2-[2-(2-{2-[10-(2-{human serum albumin-Cys34-yl}acetylamino)-decanoylamino]ethoxy}ethoxy)acetylamino]ethoxy}ethoxy)acetyl]] B29R, desB30 human insulin;

A18L, A22K[N^ε-[2-(2-{2-[2-(2-{2-[10-(2{human serum albumin-Cys34-yl}acetylamino)decanoylamino]ethoxy}ethoxy)acetylamino]ethoxy}ethoxy)acetyl]] B29R, desB30 human insulin;

A22K[N^ε-[2-(2-{2-[2-(2-{2-[16-(2-{ALBAGEN™-Cys34-yl}acetylamino)hexadecanoylamino)]ethoxy}ethoxy)acetylamino]ethoxy}ethoxy)acetyl]] B29R, desB30 human insulin;

A18L, A22K[N^ε-[2-(2-{2-[2-(2-{2-[16-(2{ALBAGEN™-Cys34-yl}acetylamino)hexadecanoylamino)]ethoxy}ethoxy)acetylamino]ethoxy}ethoxy)acetyl]] B29R, desB30 human insulin;

A22K[N^ε-[2-(2-{2-[2-(2-{2-[16-(2-{human serum albumin-Cys34-yl}acetylamino)hexadecanoylamino]ethoxy}ethoxy)acetylamino]ethoxy}ethoxy)acetyl]] B29R, desB30 human insulin;

A18L, A22K[N^ε-[2-(2-{2-[2-(2-{2-[16-(2-{human serum albumin-Cys34-yl}acetylamino)hexadecanoylamino]ethoxy}ethoxy)acetylamino]ethoxy}ethoxy)acetyl]) B29R, desB30 human insulin;

A22K[N^ε-[2-(2-{2-[2-(2-{2-[10-(3-{(ALBAGEN™-Cys34-yl)2,5-dioxopyrrolidin-1-yl}propionylamino)decanoylamino)]ethoxy}ethoxy)acetylamino]ethoxy}ethoxy)acetyl]] B29R, desB30 human insulin;

A18L, A22K[N^ε-[2-(2-{2-[2-(2-{2-[10-(3-{(ALBAGEN™-Cys34-yl)-2,5-dioxopyrrolidin-1-yl}propionylamino)decanoylamino]ethoxy}ethoxy)acetylamino]ethoxy}ethoxy)acetyl]] B29R, desB30 human insulin;

A22K[N^ε-[2-(2-{2-[2-(2-{2-[10-(3-{(human serum albumin-Cys34-yl)2,5-dioxopyrrolidin-1-yl}propionylamino)decanoylamino]ethoxy}ethoxy)acetylamino]-ethoxy}ethoxy)acetyl]] B29R, desB30 human insulin;

A18L, A22K[N^ε-[2-(2-{2-[2-(2-{2-[10-(3-{(human serum albumin-Cys35-yl)2,5-dioxopyrrolidin-1-yl}propionylamino)decanoylamino]ethoxy}-ethoxy)acetylamino]ethoxy}ethoxy)acetyl]] B29R, desB30 human insulin;

A22K[N^ε-[2-(2-{2-[2-(2-{2-[16-(3-{(ALBAGEN™-Cys34-yl)2,5-dioxopyrrolidin-1-yl}propionylamino})hexadecanoylamino]ethoxy}-ethoxy)acetylamino]ethoxy}ethoxy)acetyl]] B29R, desB30 human insulin;

A18L, A22K[N^ε-[2-(2-{2-[2-(2-{2-[16-(3-{(ALBAGEN™-Cys34-yl)2,5-dioxopyrrolidin-1-yl)propionylamino}hexadecanoylamino)-ethoxy}ethoxy)acetylamino]ethoxy}ethoxy)acetyl]] B29R, desB30 human insulin;

A22K[N^ε-[2-(2-{2-[2-(2-{2-[16-(3-{(human serum albumin-Cys34-yl)2,5-dioxopyrrolidin-1-yl}propionylamino)hexadecanoylamino]ethoxy}ethoxy)acetylamino]-ethoxy}ethoxy)acetyl]] B29R, desB30 human insulin; and A18L, A22K[N^ε-[2-(2-{2-[2-(2-{2-[16-(3-{(human serum albumin-Cys34)yl-2,5-dioxopyrrolidin-1-yl}propionylamino]hexadecanoylamino)ethoxy}ethoxy)acetylamino]ethoxy}ethoxy)acetyl]] B29R, desB30 human insulin.

3. A compound according to claim 1 wherein the group designated Ins is selected from the group consisting of A5L, A22K, B29R, desB30 human insulin; A18L, A22K, B29R, desB30 human insulin and A22K, B29R, desB30 human insulin from which a hydrogen has been removed from the epsilon amino group present in the Lys(A22) amino acid residue.

4. A compound according to claim 1 wherein the group designated M' is selected from the group consisting of

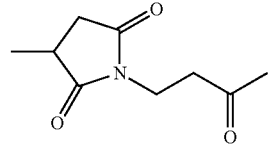

and —CH$_2$—CO—(i.e. methylecarbonyl).

5. A compound according to claim 1 wherein the group designated Z$_n$ is selected from the group consisting of —NH—CH$_2$—CH$_2$—CH$_2$—CH$_2$—CH$_2$—CH$_2$—CH$_2$—CO—; —NH—CH$_2$—CH$_2$—CH$_2$—CH$_2$—CH$_2$—CH$_2$—CH$_2$—CH$_2$—CH$_2$—CH$_2$—CO—; —NH—CH$_2$—CH$_2$—CH$_2$—CH$_2$—CH$_2$—CH$_2$—CH$_2$—CH$_2$—CH$_2$—CO— and —NH—CH$_2$—CH$_2$—CH$_2$—CH$_2$—CH$_2$—CH$_2$—CH$_2$—CH$_2$—CH$_2$—CH$_2$—CH$_2$—CH$_2$—CH$_2$—CO—.

6. A compound according to claim 1 wherein the group designated Z$_n$ or Y$_o$ is —NH—CH$_2$—CH$_2$—O—CH$_2$—CH$_2$—O—CH$_2$—CO—.

7. A compound according to claim 1 wherein the moiety designated -M'-Z$_n$—Y$_o$— is selected from the group consisting of: —CH$_2$—CO—NH—CH$_2$—CH$_2$—CH$_2$—CH$_2$—CH$_2$—CH$_2$—CH$_2$—CH$_2$—CH$_2$—CH$_2$—CH$_2$—CH$_2$—CO—; —CH$_2$—CO—NH—CH$_2$—CH$_2$—CH$_2$—CH$_2$—CH$_2$—CH$_2$—CH$_2$—CH$_2$—CH$_2$—CH$_2$—CO—NH—CH$_2$—CH$_2$—O—CH$_2$—CH$_2$—O—CH$_2$—CO—NH—CH$_2$—CH$_2$—O—CH$_2$—CH$_2$—O—CH$_2$—CO—; —CH$_2$—CO—NH—CH$_2$—CH$_2$—CH$_2$—CH$_2$—CH$_2$—CH$_2$—CH$_2$—CH$_2$—CH$_2$—CO—; —CH$_2$—CO—NH—CH$_2$—CH$_2$—CH$_2$—CH$_2$—CH$_2$—CH$_2$—CH$_2$—CH$_2$—CH$_2$—CH$_2$—CH$_2$—CO—; —CH$_2$—CO—NH—CH$_2$—CH$_2$—CH$_2$—CH$_2$—CH$_2$—CH$_2$—CH$_2$—CH$_2$—CH$_2$—CO—NH—CH$_2$—CH$_2$—O—CH$_2$—CH$_2$—O—CH$_2$—CO—NH—CH$_2$—CH$_2$—O—CH$_2$—CH$_2$—O—CH$_2$—CO—; —CH$_2$—CO—NH—CH$_2$—CH$_2$—CH$_2$—CH$_2$—CH$_2$—CH$_2$—CH$_2$—CH$_2$—CH$_2$—CH$_2$—CO—NH—CH$_2$—CH$_2$—O—CH$_2$—CH$_2$—O—CH$_2$—CO—NH—CH$_2$—CH$_2$—O—CH$_2$—CH$_2$—O—CH$_2$—CO—;

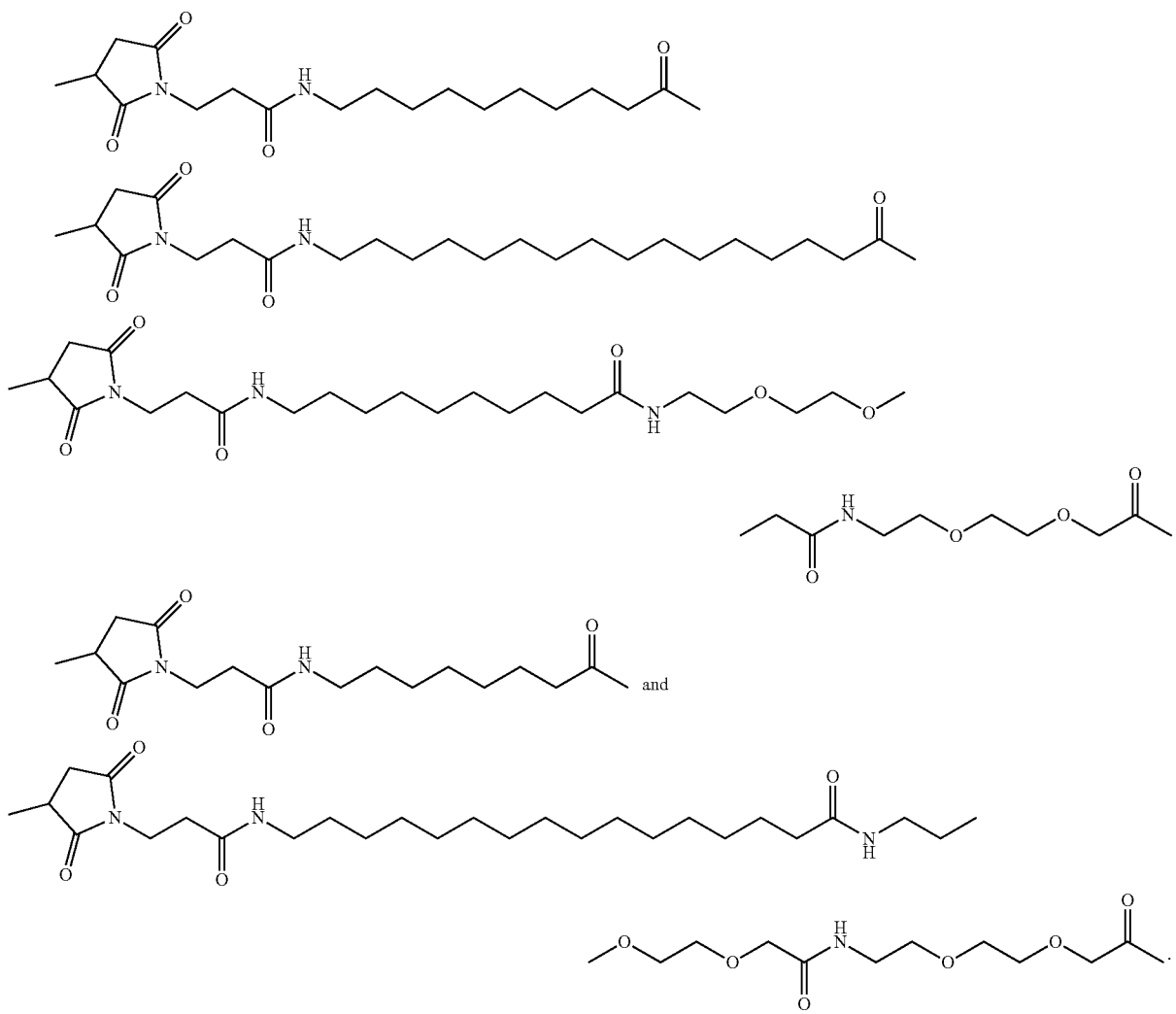

8. A pharmaceutical composition comprising a compound according to claim 1 and a pharmaceutically acceptable carrier.

9. A method of treating hyperglycemia, type 2 diabetes, impaired glucose tolerance, type 1 diabetes, obesity, syndrome X or dyslipidemia in a subject in need thereof comprising administering a pharmaceutically effective amount of a compound according to claim 1.

10. A method of treating hyperglycemia, type 2 diabetes, impaired glucose tolerance, type 1 diabetes, obesity, syndrome X or dyslipidemia in a subject in need thereof comprising administering a pharmaceutically effective amount of a pharmaceutical composition according to claim 8.

11. A method for treating diabetes in a subject in need thereof comprising administering a pharmaceutically effective amount of a compound according to claim 1.

12. A method for treating diabetes in a subject in need thereof comprising administering a pharmaceutically effective amount of a pharmaceutical composition according to claim 8.

* * * * *

UNITED STATES PATENT AND TRADEMARK OFFICE
CERTIFICATE OF CORRECTION

PATENT NO. : 9,242,011 B2
APPLICATION NO. : 12/935438
DATED : January 26, 2016
INVENTOR(S) : Tina M. Tagmose et al.

It is certified that error appears in the above-identified patent and that said Letters Patent is hereby corrected as shown below:

In the Specification:

At column 83, line 26, amend as follows:

EXAMPLE 46

A18L, A22K[$N^\varepsilon$-[2-(2-{2-[2-(2-{2-[10-(3-{(Human serum albumin-Cys34-yl)2,5-dioxopyrrolidin-1-yl}propionyl-amino)decanoylamino]ethoxy}ethoxy)acetylamino]ethoxy}ethoxy)acetyl]] B29R, desB30 human insulin In the Claims:

At column 93, claim number 2, line number 15, amend as follows:

A22K[Nε-[2-(2-{2-[2-(2-{2-[10-(2-{ALBAGEN™-Cys34-yl}acetylamino)decanoylamino]ethoxy}¬ethoxy)¬acetyl¬amino]¬ethoxy}¬ethoxy)¬acetyl]] B29R, desB30 human insulin;

At column 93, claim number 2, line number 62, amend as follows:

A18L, A22K[Nε-[2-(2-{2-[2-(2-{2-[10-(3-{(human serum albumin-Cys34-yl)2,5-dioxopyrrolidin-1-yl}¬propionyl¬amino)¬decanoyl¬¬amino]¬ethoxy}¬ethoxy)acetylamino]ethoxy}ethoxy)acetyl]] B29R, desB30 human insulin;

Signed and Sealed this
Fifth Day of July, 2016

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 22
<212> TYPE: PRT
<213> ORGANISM: Artificial Sequence
<220> FEATURE:
<223> OTHER INFORMATION: Modified A chain

<400> SEQUENCE: 1

Gly Ile Val Glu Leu Cys Cys Thr Ser Ile Cys Ser Leu Tyr Gln Leu
1               5                   10                  15

Glu Asn Tyr Cys Asn Lys
            20

<210> SEQ ID NO 2
<211> LENGTH: 22
<212> TYPE: PRT
<213> ORGANISM: Artificial Sequence
<220> FEATURE:
<223> OTHER INFORMATION: Modified A chain

<400> SEQUENCE: 2

Gly Ile Val Glu Gln Cys Cys Thr Ser Ile Cys Ser Leu Tyr Gln Leu
1               5                   10                  15

Glu Leu Tyr Cys Asn Lys
            20

<210> SEQ ID NO 3
<211> LENGTH: 22
<212> TYPE: PRT
<213> ORGANISM: Artificial Sequence
<220> FEATURE:
<223> OTHER INFORMATION: Modified A chain

<400> SEQUENCE: 3

Ile Val Glu Gln Cys Cys Thr Ser Ile Cys Ser Leu Tyr Gln Leu
1               5                   10                  15

Glu Asn Tyr Cys Asn Lys
            20

<210> SEQ ID NO 4
<211> LENGTH: 29
<212> TYPE: PRT
<213> ORGANISM: Artificial Sequence
<220> FEATURE:
<223> OTHER INFORMATION: Modified B chain

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Arg
            20                  25
```